(12) United States Patent
Ciccone et al.

(10) Patent No.: US 12,233,232 B2
(45) Date of Patent: Feb. 25, 2025

(54) GENDERLESS ASEPTIC CONNECTOR

(71) Applicant: WilMarc Holdings, LLC, Fort Collins, CO (US)

(72) Inventors: Paul C. Ciccone, Wellington, CO (US); William A. Coulson, Cheyenne, WY (US); Marcia Coulson, Cheyenne, WY (US)

(73) Assignee: WilMarc Holdings, LLC, Fort Collins, CO (US)

( * ) Notice: Subject to any disclaimer, the term of this patent is extended or adjusted under 35 U.S.C. 154(b) by 0 days.

(21) Appl. No.: 18/645,975

(22) Filed: Apr. 25, 2024

(65) Prior Publication Data
US 2024/0358992 A1    Oct. 31, 2024

Related U.S. Application Data

(60) Provisional application No. 63/461,638, filed on Apr. 25, 2023.

(51) Int. Cl.
  *A61M 39/24*   (2006.01)
  *A61M 39/10*   (2006.01)
  A61M 39/22   (2006.01)

(52) U.S. Cl.
  CPC ........ *A61M 39/24* (2013.01); *A61M 39/1011* (2013.01); *A61M 2039/226* (2013.01);
  (Continued)

(58) Field of Classification Search
  CPC .................. A61M 39/00; A61M 39/06; A61M 39/0606; A61M 39/0613; A61M 39/10;
  (Continued)

(56) References Cited

U.S. PATENT DOCUMENTS

| 964,310 A | 7/1910 | Perazio |
| 2,208,286 A | 7/1940 | Berger |
| (Continued) | | |

FOREIGN PATENT DOCUMENTS

| CA | 021 656 | 11/1977 |
| CA | 1084551 | 8/1980 |
| (Continued) | | |

OTHER PUBLICATIONS

Eldon James. Introducing SeriesLock™ the Spring-Free Flow Path Quick Disconnect Coupler (with video). Website, https://www.eldonjames.com/serieslock-quick-disconnect-coupler/, originally downloaded Jun. 6, 2018, 5 pages.
(Continued)

*Primary Examiner* — Joel M Attey
*Assistant Examiner* — Alexandra Lalonde
(74) *Attorney, Agent, or Firm* — Craig R. Miles; CR MILES P.C.

(57) ABSTRACT

Disclosed herein are embodiments of a connector system for releasably connecting together tubes, whereby the connector system includes a first coupler including a first coupler passageway disposed within the first coupler, and a first coupler elastically deformable valve operable to seal the first coupler passageway from an external environment. The connector system further includes a second coupler including a second coupler passageway disposed within the second coupler, and a second coupler elastically deformable valve operable to seal the second coupler passageway from the external environment. The first coupler and the second coupler can be substantially identical; thus, the first coupler and the second coupler can be genderless, as opposed to a connector system comprising a male coupler and a female coupler. The connector system can further include a first coupler valve operable to interrupt the fluid flow through the
(Continued)

first coupler passageway, and a second coupler valve operable to interrupt fluid flow through the second coupler passageway.

20 Claims, 30 Drawing Sheets

(52) U.S. Cl.
CPC .............. *A61M 2039/2426* (2013.01); *A61M 2039/246* (2013.01); *A61M 2205/581* (2013.01); *A61M 2207/00* (2013.01)

(58) Field of Classification Search
CPC .......... A61M 39/1011; A61M 39/0693; A61M 39/105; A61M 39/1055; A61M 39/14; A61M 39/16; A61M 39/165; A61M 39/18; A61M 39/20; A61M 39/22; A61M 39/221; A61M 39/24; A61M 39/26; A61M 2039/0009; A61M 2039/0018; A61M 2039/0027; A61M 2039/0036; A61M 2039/0063; A61M 2039/0072; A61M 2039/009; A61M 2039/062; A61M 2039/0626; A61M 2039/0633; A61M 2039/064; A61M 2039/0646; A61M 2039/0653; A61M 2039/066; A61M 2039/0666; A61M 2039/0673; A61M 2039/068; A61M 2039/0686; A61M 2039/1016; A61M 2039/1022; A61M 2039/1027; A61M 2039/1033; A61M 2039/1038; A61M 2039/1061; A61M 2039/1066; A61M 2039/1072; A61M 2039/1077; A61M 2039/1083; A61M 2039/1088; A61M 2039/2426; A61M 2039/2433; A61M 2039/244; A61M 2039/2446; A61M 2039/2493; A61M 2039/261; A61M 2039/262; A61M 2039/263; A61M 2039/265; A61M 2039/267; A61M 2039/268; A61M 2039/1044; A61M 2039/226; A61M 2039/246; A61M 2205/581; A61M 2205/0205; A61M 2205/0216; A61M 2207/00

See application file for complete search history.

(56) References Cited

U.S. PATENT DOCUMENTS

| | | | |
|---|---|---|---|
| 2,218,318 A | 10/1940 | Pfauser |
| 2,263,293 A | 11/1941 | Ewald |
| 2,304,390 A | 12/1942 | Wolfram |
| 2,451,218 A | 10/1948 | Hengst |
| 2,456,045 A | 12/1948 | Brock |
| 2,545,796 A | 3/1951 | Scheiwer |
| 2,648,548 A | 8/1953 | Scheiwer |
| 2,777,716 A | 1/1957 | Gray |
| 2,805,089 A | 9/1957 | Hansen |
| 2,854,259 A | 9/1958 | Clark |
| 2,951,713 A | 9/1960 | Hoffstrom |
| 3,291,152 A | 12/1966 | Comer |
| 3,460,801 A | 8/1969 | Norton |
| 3,592,231 A | 7/1971 | Lamb |
| 3,719,194 A | 3/1973 | Anderson et al. |
| 3,847,413 A | 11/1974 | Gurley et al. |
| 3,916,929 A | 11/1975 | Brown |
| 4,019,512 A | 4/1977 | Tenczar |
| 4,187,846 A | 2/1980 | Lolachi et al. |
| 4,220,174 A | 9/1980 | Spitz |
| 4,415,085 A | 11/1983 | Clarke et al. |
| 4,436,125 A | 3/1984 | Blenkush |
| 4,500,118 A | 2/1985 | Blenkush |
| 4,541,457 A | 9/1985 | Blenkush |
| 4,543,993 A | 10/1985 | Calvin et al. |
| 4,576,359 A | 3/1986 | Oetiker |
| 4,625,761 A | 12/1986 | Uchida et al. |
| 4,630,847 A | 12/1986 | Blenkush |
| 4,676,778 A | 6/1987 | Nelson, Jr. |
| 4,703,957 A | 11/1987 | Blenkush |
| 4,703,958 A | 11/1987 | Fremy |
| 4,733,692 A | 3/1988 | Kotake et al. |
| 4,819,692 A | 4/1989 | Olson et al. |
| 4,877,145 A | 10/1989 | Manner |
| 4,903,995 A | 2/1990 | Blenkush et al. |
| 4,934,655 A | 6/1990 | Blenkush et al. |
| 4,946,200 A | 8/1990 | Blenkush et al. |
| 4,953,592 A | 9/1990 | Takahashi et al. |
| 5,009,252 A | 4/1991 | Faughn |
| 5,033,777 A | 7/1991 | Blenkush |
| 5,052,725 A | 10/1991 | Meyer et al. |
| 5,076,615 A | 12/1991 | Sampson |
| 5,104,158 A | 4/1992 | Meyer et al. |
| 5,137,527 A | 8/1992 | Miller et al. |
| 5,165,733 A | 11/1992 | Sampson |
| 5,178,303 A | 1/1993 | Blenkush et al. |
| D339,417 S | 9/1993 | Sampson et al. |
| 5,259,894 A | 11/1993 | Sampson |
| 5,295,339 A | 3/1994 | Manner |
| 5,316,041 A | 5/1994 | Ramacier, Jr. et al. |
| 5,353,836 A | 10/1994 | deCler et al. |
| 5,390,702 A | 2/1995 | Smith, III |
| D357,307 S | 4/1995 | Ramacier, Jr. et al. |
| 5,460,413 A | 10/1995 | Sampson |
| 5,494,074 A | 2/1996 | Ramacier, Jr. et al. |
| 5,529,085 A | 6/1996 | Richards et al. |
| D372,093 S | 7/1996 | Sampson et al. |
| 5,546,985 A | 8/1996 | Bartholomew |
| D375,160 S | 10/1996 | Sampson et al. |
| 5,564,752 A | 10/1996 | Sampson |
| 5,639,064 A | 6/1997 | deCler et al. |
| D384,731 S | 10/1997 | Ramacier, Jr. et al. |
| 5,695,221 A | 12/1997 | Sunderhaus |
| D388,876 S | 1/1998 | Sampson |
| 5,704,106 A | 1/1998 | Sampson et al. |
| 5,799,987 A | 9/1998 | Sampson |
| 5,820,614 A | 10/1998 | Erskine et al. |
| 5,826,610 A | 10/1998 | Bodhaine |
| 5,837,180 A | 11/1998 | Linder et al. |
| 5,845,943 A | 12/1998 | Ramacier, Jr. et al. |
| 5,848,811 A | 12/1998 | Sampson |
| 5,848,997 A | 12/1998 | Erskine et al. |
| 5,869,803 A | 2/1999 | Noguchi et al. |
| 5,911,403 A | 6/1999 | deCler et al. |
| 5,937,885 A | 8/1999 | Sampson |
| 5,938,244 A | 8/1999 | Meyer |
| 5,975,489 A | 11/1999 | deCler et al. |
| 6,024,124 A | 2/2000 | Braun et al. |
| 6,050,297 A | 4/2000 | Ostrowski et al. |
| 6,082,401 A | 7/2000 | Braun et al. |
| 6,095,191 A | 8/2000 | Smith, III |
| 6,146,374 A | 11/2000 | Erskine et al. |
| 6,161,578 A | 12/2000 | Braun et al. |
| 6,206,040 B1 | 3/2001 | Smith, III |
| 6,231,089 B1 | 5/2001 | deCler et al. |
| 6,382,593 B1 | 5/2002 | deCler et al. |
| 6,412,829 B1 | 7/2002 | Persson |
| 6,511,100 B1 | 1/2003 | Le Clinche |
| 6,557,824 B1 | 5/2003 | Jenski, Jr. et al. |
| 6,581,907 B1 | 6/2003 | Kuwabara et al. |
| 6,607,097 B2 | 8/2003 | Savage et al. |
| 6,626,419 B2 | 9/2003 | deCler et al. |
| 6,649,829 B2 | 11/2003 | Garber et al. |
| 6,705,591 B2 | 3/2004 | deCler |
| 6,848,602 B2 | 2/2005 | deCler et al. |
| 6,871,669 B2 | 3/2005 | Meyer et al. |
| D503,778 S | 4/2005 | Wicks |
| 6,886,803 B2 | 5/2005 | Mikiya et al. |
| 6,897,374 B2 | 5/2005 | Garber et al. |
| 6,902,144 B2 | 6/2005 | deCler |

(56) References Cited

U.S. PATENT DOCUMENTS

| | | |
|---|---|---|
| 6,916,007 B2 | 7/2005 | deCler et al. |
| 6,962,275 B2 | 11/2005 | deCler et al. |
| 6,978,800 B2 | 12/2005 | deCler et al. |
| 7,080,665 B2 | 7/2006 | Whall |
| 7,147,627 B2 | 12/2006 | Kim et al. |
| 7,163,022 B2 | 1/2007 | Whall |
| 7,316,424 B2 | 1/2008 | Kardeis et al. |
| 7,384,783 B2 | 6/2008 | Kunas et al. |
| 7,394,375 B2 | 7/2008 | Johnson |
| 7,434,842 B2 | 10/2008 | Schmidt |
| 7,448,653 B2 | 11/2008 | Jensen et al. |
| 7,469,472 B2 | 12/2008 | deCler et al. |
| 7,488,446 B2 | 2/2009 | Meyer et al. |
| 7,514,025 B2 | 4/2009 | Hofmann et al. |
| 7,544,191 B2 | 6/2009 | Peluso et al. |
| 7,546,857 B2 | 6/2009 | Chadbourne et al. |
| 7,547,047 B2 | 6/2009 | deCler et al. |
| 7,562,906 B2 | 7/2009 | Schmidt |
| D602,128 S | 10/2009 | Williams et al. |
| 7,631,660 B2 | 12/2009 | deCler et al. |
| 7,647,954 B2 | 1/2010 | Garber et al. |
| D612,019 S | 3/2010 | Williams et al. |
| D612,021 S | 3/2010 | Schmidt |
| 7,695,020 B2 | 4/2010 | Schmidt |
| 7,708,025 B2 | 5/2010 | Johnson |
| 7,722,583 B2 | 5/2010 | Kim et al. |
| 7,757,974 B2 | 7/2010 | Hofmann et al. |
| 7,770,939 B2 | 8/2010 | Jensen et al. |
| 7,806,139 B2 | 10/2010 | Packham et al. |
| 7,828,336 B2 | 11/2010 | Gammons |
| 7,841,357 B2 | 11/2010 | Rankin |
| D629,894 S | 12/2010 | Lombardi, III et al. |
| D630,320 S | 1/2011 | Lombardi, III et al. |
| 7,875,346 B2 | 1/2011 | Hofmann et al. |
| 7,878,553 B2 | 2/2011 | Wicks et al. |
| D634,840 S | 3/2011 | Lombardi, III et al. |
| 7,901,934 B2 | 3/2011 | Kunas et al. |
| 7,921,875 B2 | 4/2011 | Moriiki et al. |
| 7,950,700 B2 | 5/2011 | Willemstyn et al. |
| D639,398 S | 6/2011 | Wilhelm |
| 7,954,374 B2 | 6/2011 | Rankin |
| 7,954,515 B2 | 6/2011 | Gerst |
| D642,244 S | 7/2011 | Wilhelm |
| 7,976,072 B2 | 7/2011 | Parrish |
| D645,547 S | 9/2011 | Lombardi et al. |
| 8,016,816 B2 | 9/2011 | Gregory |
| D649,240 S | 11/2011 | Lewis et al. |
| D649,938 S | 12/2011 | Erickson et al. |
| D649,939 S | 12/2011 | Erickson et al. |
| D650,478 S | 12/2011 | Lewis |
| 8,075,540 B2 | 12/2011 | von Dyck et al. |
| D652,510 S | 1/2012 | Lombardi, III et al. |
| D652,511 S | 1/2012 | Lombardi, III et al. |
| D654,573 S | 2/2012 | Lombardi et al. |
| 8,113,546 B2 | 2/2012 | Jensen et al. |
| D655,393 S | 3/2012 | Whitaker |
| 8,162,242 B2 | 4/2012 | Hofmann et al. |
| 8,187,867 B2 | 5/2012 | Kunas et al. |
| D663,022 S | 7/2012 | Lombardi, III et al. |
| 8,235,426 B2 | 8/2012 | Pisula, Jr. et al. |
| 8,256,803 B2 | 9/2012 | Takahashi |
| 8,323,255 B2 | 12/2012 | Martino et al. |
| 8,388,873 B2 | 3/2013 | Hofmann et al. |
| 8,397,756 B2 | 3/2013 | Packham et al. |
| 8,448,994 B2 | 5/2013 | Pisula, Jr. et al. |
| RE44,310 E | 6/2013 | Chadbourne et al. |
| 8,491,016 B2 | 7/2013 | Williams et al. |
| 8,596,688 B2 | 12/2013 | Pisula, Jr. et al. |
| D698,440 S | 1/2014 | Lombardi, III et al. |
| 8,623,640 B2 | 1/2014 | Kunas et al. |
| D699,841 S | 2/2014 | Lombardi, III et al. |
| 8,684,035 B2 | 4/2014 | Bernhard |
| 8,795,256 B1 * | 8/2014 | Smith ............... A61M 39/26 |
| | | 604/249 |
| D712,537 S | 9/2014 | Lombardi et al. |
| 8,897,756 B2 | 11/2014 | Skog et al. |
| 8,926,577 B2 | 1/2015 | Nishtala et al. |
| 8,945,091 B2 | 2/2015 | Williams et al. |
| D724,703 S | 3/2015 | Downs |
| 9,027,968 B2 | 5/2015 | Gerst |
| 9,046,205 B2 | 6/2015 | Whitaker et al. |
| 9,157,560 B2 | 10/2015 | Rehder et al. |
| 9,266,257 B2 | 2/2016 | Hofmann et al. |
| 9,279,530 B2 | 3/2016 | Schmidt |
| 9,327,893 B2 | 5/2016 | Steele et al. |
| 9,364,653 B2 | 6/2016 | Williams et al. |
| 9,371,921 B2 | 6/2016 | Whitaker |
| D761,395 S | 7/2016 | Plackner et al. |
| 9,388,929 B2 | 7/2016 | Lewis et al. |
| D762,826 S | 8/2016 | Plackner et al. |
| 9,463,110 B2 | 10/2016 | Nishtala et al. |
| 9,464,741 B2 | 10/2016 | Lewis et al. |
| 9,498,800 B2 | 11/2016 | Hofmann et al. |
| 9,506,590 B2 | 11/2016 | Wilhelm et al. |
| 9,540,606 B2 | 1/2017 | Kunas et al. |
| 9,770,581 B2 | 9/2017 | Gerst et al. |
| 9,879,808 B2 | 1/2018 | Williams et al. |
| 9,901,729 B2 | 2/2018 | Vigna et al. |
| 10,173,046 B2 | 1/2019 | Ciccone et al. |
| 10,213,592 B2 | 2/2019 | Gerst et al. |
| 10,293,150 B2 | 5/2019 | Ciccone et al. |
| 10,307,583 B2 | 6/2019 | Williams et al. |
| 10,350,401 B2 | 7/2019 | Ciccone et al. |
| 10,486,880 B2 | 11/2019 | Franca et al. |
| 10,583,281 B2 | 3/2020 | Ciccone et al. |
| 10,632,297 B2 | 4/2020 | Gerst et al. |
| 10,640,741 B2 | 5/2020 | Kunas et al. |
| 10,675,454 B2 | 6/2020 | Vigna et al. |
| 10,871,250 B2 | 12/2020 | Williams et al. |
| 11,357,963 B2 | 6/2022 | Williams et al. |
| 11,591,556 B2 | 2/2023 | Kunas et al. |
| 2001/0035220 A1 | 11/2001 | Russell |
| 2002/0011730 A1 | 1/2002 | Stickan |
| 2002/0014608 A1 | 2/2002 | deCler et al. |
| 2002/0024216 A1 | 2/2002 | Rose et al. |
| 2002/0063427 A1 | 5/2002 | Schiemann et al. |
| 2002/0074533 A1 | 6/2002 | DeCler et al. |
| 2002/0101076 A1 | 8/2002 | Barrier |
| 2002/0129858 A1 | 9/2002 | Meyer et al. |
| 2002/0170731 A1 | 11/2002 | Garber et al. |
| 2002/0190453 A1 | 12/2002 | Wilhelm et al. |
| 2003/0042734 A1 | 3/2003 | Kuwabara |
| 2003/0062498 A1 | 4/2003 | DeCler et al. |
| 2003/0062501 A1 | 4/2003 | DeCler |
| 2003/0196703 A1 | 10/2003 | DeCler et al. |
| 2004/0016900 A1 | 1/2004 | Kouda |
| 2004/0079423 A1 | 4/2004 | Mikiya et al. |
| 2004/0130438 A1 | 7/2004 | Garber |
| 2004/0169368 A1 | 9/2004 | Garber et al. |
| 2004/0173769 A1 | 9/2004 | DeCler |
| 2004/0222180 A1 | 11/2004 | Wicks et al. |
| 2004/0232175 A1 | 11/2004 | DeCler et al. |
| 2005/0001425 A1 | 1/2005 | DeCler et al. |
| 2005/0012330 A1 | 1/2005 | Schmidt |
| 2005/0057042 A1 | 3/2005 | Wicks |
| 2005/0076964 A1 | 4/2005 | Whall |
| 2005/0082828 A1 | 4/2005 | Wicks et al. |
| 2005/0084410 A1 | 4/2005 | Meyer et al. |
| 2005/0127117 A1 | 6/2005 | deCler et al. |
| 2005/0211934 A1 | 9/2005 | Garber et al. |
| 2005/0237241 A1 | 10/2005 | Garber et al. |
| 2005/0247371 A1 | 11/2005 | Chadbourne et al. |
| 2006/0048849 A1 | 3/2006 | DeCler |
| 2006/0076419 A1 | 4/2006 | Johnson |
| 2006/0138704 A1 | 6/2006 | DeCler et al. |
| 2006/0186233 A1 | 8/2006 | Holm et al. |
| 2006/0196556 A1 | 9/2006 | Johnson |
| 2006/0207345 A1 | 9/2006 | Rankin |
| 2006/0231137 A1 | 10/2006 | Whall |
| 2007/0001452 A1 | 1/2007 | Friel |
| 2007/0025811 A1 | 2/2007 | Wilhelm |
| 2007/0102051 A1 | 5/2007 | Zeiber et al. |
| 2007/0169825 A1 | 7/2007 | Packham et al. |
| 2007/0209716 A1 | 9/2007 | Rankin |

(56) References Cited

U.S. PATENT DOCUMENTS

| | | |
|---|---|---|
| 2007/0259246 A1 | 11/2007 | Jang et al. |
| 2008/0001395 A1 | 1/2008 | Kouda |
| 2008/0011785 A1 | 1/2008 | Braun et al. |
| 2008/0061553 A1 | 3/2008 | Schmidt |
| 2008/0067807 A1 | 3/2008 | DeCler et al. |
| 2008/0191069 A1 | 8/2008 | Hofmann et al. |
| 2008/0277924 A1 | 11/2008 | Jensen et al. |
| 2009/0021007 A1 | 1/2009 | Le Bars et al. |
| 2009/0030387 A1 | 1/2009 | Kim et al. |
| 2009/0051161 A1 | 2/2009 | Ekstrom |
| 2009/0167018 A1 | 7/2009 | Lien |
| 2009/0188575 A1 | 7/2009 | Williams et al. |
| 2009/0256355 A1 | 10/2009 | Wicks et al. |
| 2009/0261582 A1 | 10/2009 | Gaudin |
| 2009/0284007 A1 | 11/2009 | Schmidt |
| 2010/0001516 A1 | 1/2010 | Pisula, Jr. et al. |
| 2010/0006157 A1 | 1/2010 | Gerst |
| 2010/0006162 A1 | 1/2010 | Rankin |
| 2010/0019487 A1 | 1/2010 | deCler et al. |
| 2010/0043988 A1 | 2/2010 | Hofmann et al. |
| 2010/0127492 A1 | 5/2010 | Poder et al. |
| 2010/0155979 A1 | 6/2010 | Hofmann et al. |
| 2010/0230950 A1 | 9/2010 | Williams et al. |
| 2010/0295295 A1 | 11/2010 | Schmidt |
| 2010/0301599 A1 | 12/2010 | Jensen et al. |
| 2011/0012340 A1 | 1/2011 | Packham et al. |
| 2011/0062701 A1 | 3/2011 | Downs et al. |
| 2011/0121035 A1 | 5/2011 | Greter et al. |
| 2011/0127767 A1 | 6/2011 | Wicks et al. |
| 2011/0204621 A1 | 8/2011 | Whitaker et al. |
| 2011/0204622 A1 | 8/2011 | Lewis et al. |
| 2011/0210541 A1 | 9/2011 | Lewis et al. |
| 2011/0240158 A1 | 10/2011 | Py |
| 2011/0295236 A1 | 12/2011 | Gregory |
| 2012/0031515 A1 | 2/2012 | Whitaker |
| 2012/0068457 A1 | 3/2012 | Pisula, Jr. et al. |
| 2012/0161051 A1 | 6/2012 | Williams et al. |
| 2012/0179052 A1 | 7/2012 | Wilhelm et al. |
| 2012/0259237 A1 | 10/2012 | Axelrod |
| 2013/0030387 A1 | 1/2013 | Williams et al. |
| 2013/0092271 A1 | 4/2013 | Downs et al. |
| 2013/0099489 A1 | 4/2013 | Williams et al. |
| 2013/0207380 A1 | 8/2013 | Williams et al. |
| 2013/0245531 A1 | 9/2013 | Brandl et al. |
| 2013/0289517 A1 | 10/2013 | Williams et al. |
| 2013/0320668 A1 | 12/2013 | Cheon et al. |
| 2013/0333767 A1 | 12/2013 | Schmidt |
| 2014/0060675 A1 | 3/2014 | Wilhelm et al. |
| 2014/0117664 A1 | 5/2014 | Ekstrom |
| 2014/0260554 A1 | 9/2014 | Rankin |
| 2014/0261819 A1 | 9/2014 | Vranish |
| 2015/0028586 A1 | 1/2015 | Gerst et al. |
| 2015/0076815 A1 | 3/2015 | Lombardi, III et al. |
| 2015/0090915 A1 | 4/2015 | Vranish |
| 2015/0135502 A1 | 5/2015 | Rankin et al. |
| 2015/0231369 A1 | 8/2015 | Gray et al. |
| 2015/0260325 A1 | 9/2015 | Quick |
| 2015/0276111 A1 | 10/2015 | Ira et al. |
| 2016/0018037 A1 | 1/2016 | Nichols et al. |
| 2016/0033068 A1 | 2/2016 | Wilhelm |
| 2016/0046130 A1 | 2/2016 | Burdge et al. |
| 2016/0047503 A1 | 2/2016 | Ballard et al. |
| 2016/0102791 A1 | 4/2016 | Johnson et al. |
| 2016/0208971 A1 | 7/2016 | Lewis et al. |
| 2016/0208972 A1 | 7/2016 | Lewis et al. |
| 2016/0243348 A1 | 8/2016 | Williams et al. |
| 2016/0305574 A1 | 10/2016 | Burdge |
| 2017/0009919 A1 | 1/2017 | Lewis et al. |
| 2017/0020711 A1 | 1/2017 | Nishtala et al. |
| 2017/0203089 A1 | 7/2017 | Ciccone et al. |
| 2018/0243546 A1* | 8/2018 | Leuthardt .......... A61M 39/1011 |
| 2018/0304066 A1 | 10/2018 | Ciccone et al. |
| 2019/0078714 A1 | 3/2019 | Brugger et al. |
| 2019/0138032 A1 | 5/2019 | Shevgoor |
| 2019/0269901 A1 | 9/2019 | Ciccone et al. |
| 2020/0188651 A1 | 6/2020 | Ciccone et al. |
| 2021/0095802 A1 | 4/2021 | Andrews et al. |
| 2022/0252194 A1 | 8/2022 | Benson |
| 2022/0305249 A1 | 9/2022 | Nichols et al. |
| 2023/0003324 A1 | 1/2023 | Ciccone et al. |
| 2024/0044428 A1* | 2/2024 | Le Quere ................ F16L 29/00 |

FOREIGN PATENT DOCUMENTS

| | | |
|---|---|---|
| CA | 844 802 | 2/2013 |
| FR | 960 425 | 12/2011 |
| JP | 6214465 | 4/1987 |
| JP | 2011-075055 | 4/2011 |
| WO | 01/10362 | 2/2001 |
| WO | 2014/178861 | 11/2014 |
| WO | WO 2022/129413 A1 | 6/2022 |

OTHER PUBLICATIONS

Nordson Medical. Shop Fluid Management Products. Website, https://www.nordsonmedical.com, originally downloaded Jun. 29, 2020, 3 pages.

PCT International Patent Application No. PCT/US18/21467, International Search Report and Written Opinion of the International Searching Authority dated Jun. 1, 2018, 9 pages.

PCT International Patent Application No. PCT/US2017/014189, filed Jan. 19, 2017.

PCT International Patent Application No. PCT/US2017/014189, International Search Report and Written Opinion of the International Searching Authority, mailed May 23, 2017, 13 pages total.

European Patent Application No. 16000568.2, Office Action dated Apr. 1, 2019, 7 pages.

European Patent Application No. 17741950.4, Extended European Search Report dated Sep. 9, 2019, 8 pages.

U.S. Appl. No. 62/280,354, filed Jan. 19, 2016.

U.S. Appl. No. 62/299,499, filed Feb. 24, 2016.

U.S. Appl. No. 62/468,800, filed Mar. 8, 2017.

U.S. Appl. No. 15/410,636, filed Jan. 19, 2017.

U.S. Appl. No. 15/410,636, Office Action mailed Aug. 18, 2017.

U.S. Appl. No. 15/410,636, Office Action mailed Sep. 22, 2017.

U.S. Appl. No. 15/410,636, Office Action mailed Jan. 25, 2018.

U.S. Appl. No. 15/447,033, filed Mar. 1, 2017.

U.S. Appl. No. 15/912,280, filed Mar. 5, 2018.

U.S. Appl. No. 15/912,280, Office Action mailed Dec. 17, 2018.

U.S. Appl. No. 15/912,280, Office Action mailed Apr. 23, 2019.

U.S. Appl. No. 16/024,414, Office Action mailed Dec. 18, 2019.

U.S. Appl. No. 16/024,414, Office Action mailed Jul. 24, 2020.

U.S. Appl. No. 16/503,757, Office Action mailed Aug. 15, 2019.

PCT International Patent Application No. PCT/US24/26237, International Search Report and Written Opinion of the International Searching Authority dated Aug. 14, 2024, 10 pages.

CPC. AseptiQuik® Sterile Connectors. Website, https://www.cpcworldwide.com/Biopharma/AseptiQuik?gad_source=1&gclid=Cj0KCQjw_gexBhCoARIsAFgBleuFzYyKVkpbsUva0O2xF4kC0jrOGt-QnRzmwhN41UGB1C4Nn5eBbToAszaEALw_wcB, originally downloaded Jul. 1, 2024, 4 pages.

Milliporesigma. Connectors, Tubing and Crimping. Website, https://www.emdmillipore.com/US/en/products/biopharmaceutical-manufacturing/downstream-processing/single-use-manufacturing/connectors-crimping-tubing/adOb.qB.O.IAAAFDezF4saSR,nav, originally downloaded Nov. 20, 2024, 1 page.

Saint-Gobain. Pure-Fit® SC Sterile Connectors. Website, https://www.biopharm.saint-gobain.com/components/connection-flow-control/pure-fit-sc-sterile-connectors, originally downloaded Jul. 1, 2024, 5 pages.

CPC. Aseptiquik® G Series Connectors. Specification List. Website, https://www.cpcworldwide.com, originally downloaded Mar. 28, 2023, 2 pages.

Youtube. CPC Aseptiquik G Assembly. Video, https://www.youtube.com/watch?v=XEFy0cQ6cJg, published in Year: 2017, originally downloaded Apr. 24, 2023.

(56) References Cited

OTHER PUBLICATIONS

Youtube. Kleenpak® Presto Sterile Connector (Pall Biotech). Video, https://www.youtube.com/watch?v=8LktNhZQras, published in Year: 2018, originally downloaded Apr. 24, 2023.
PCT International Patent Application No. PCT/US22/35669, International Search Report and Written Opinion of the International Searching Authority dated Oct. 20, 2022, 11 pages.
Canadian Patent Application No. 3,156,502, Office Action mailed Sep. 11, 2024, 4 pages.
European Patent Application No. 17741950.4, Office Action dated Jul. 30, 2020, 5 pages.
European Patent Application No. 18763491.0, Extended European Search Report dated Dec. 16, 2020, 13 pages.
Japanese Patent Application No. 2018/537509, Official Action mailed Apr. 2, 2020, 7 pages (with English translation).
U.S. Appl. No. 16/415,640, Office Action mailed Apr. 27, 2020.
U.S. Appl. No. 16/415,640, Office Action mailed Jan. 12, 2021.
U.S. Appl. No. 16/415,640, Office Action mailed Jul. 20, 2021.
U.S. Appl. No. 16/024,414, Office Action mailed Feb. 2, 2021.
U.S. Appl. No. 16/024,414, Office Action mailed Aug. 31, 2021.
U.S. Appl. No. 16/811,223, Office Action mailed Jul. 22, 2021.
U.S. Appl. No. 16/802,412, Office Action mailed Oct. 27, 2020.

\* cited by examiner

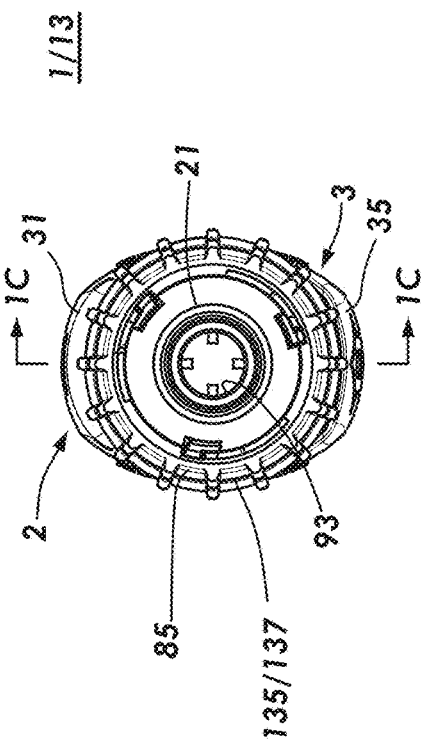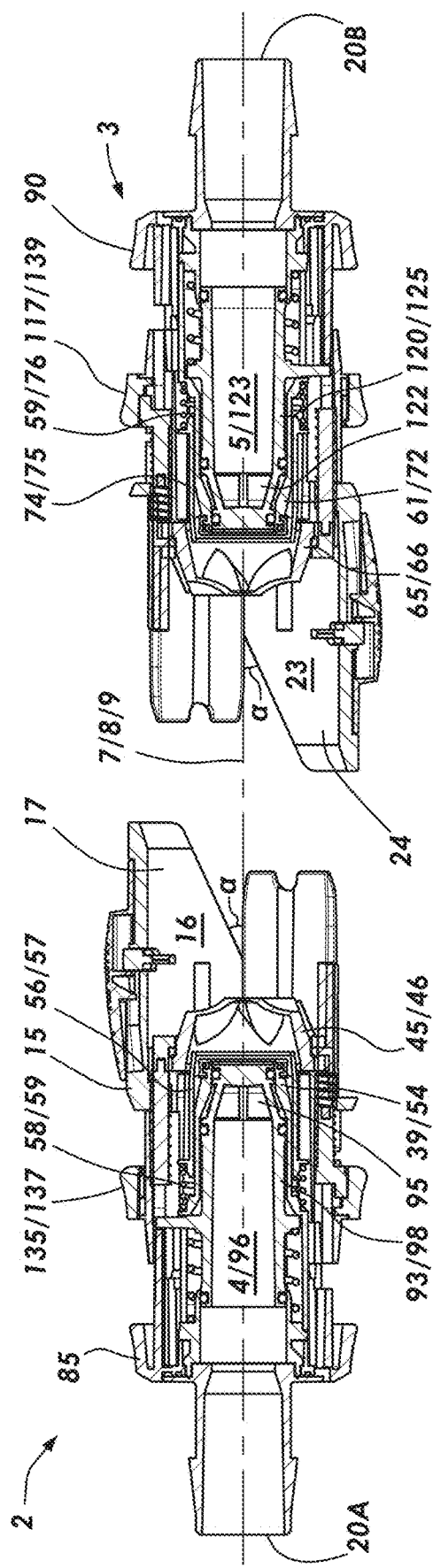
FIG. 1B
FIG. 1C

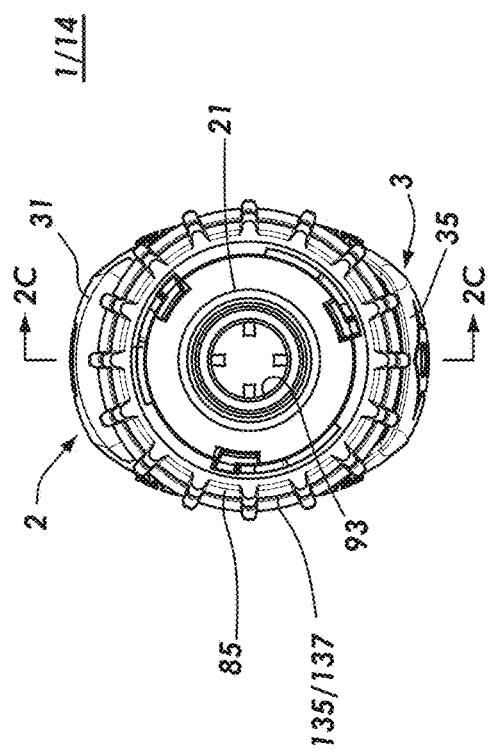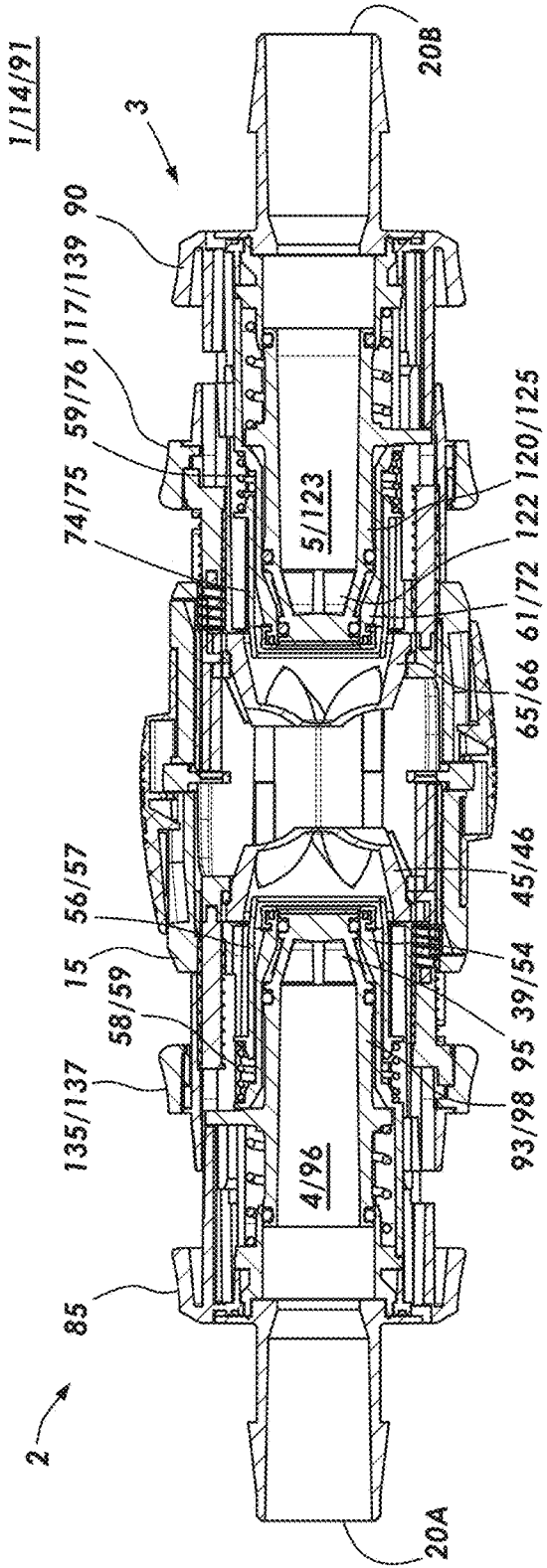

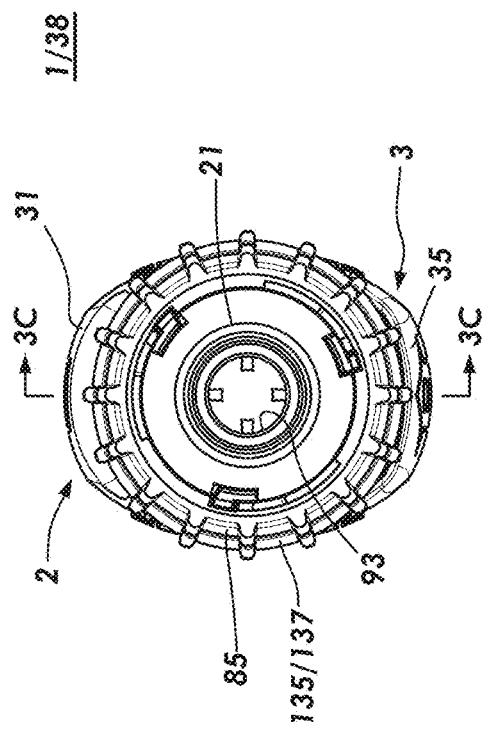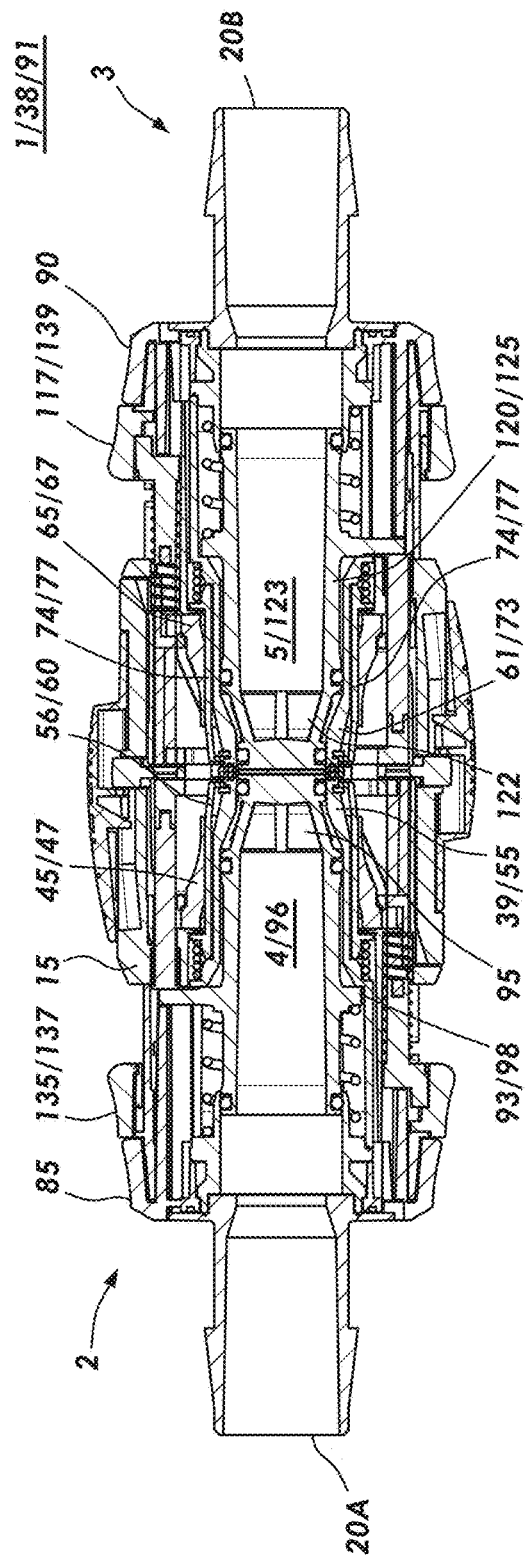

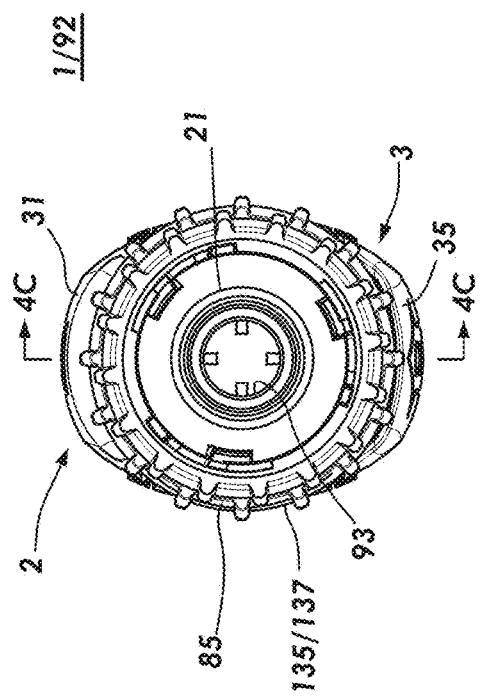
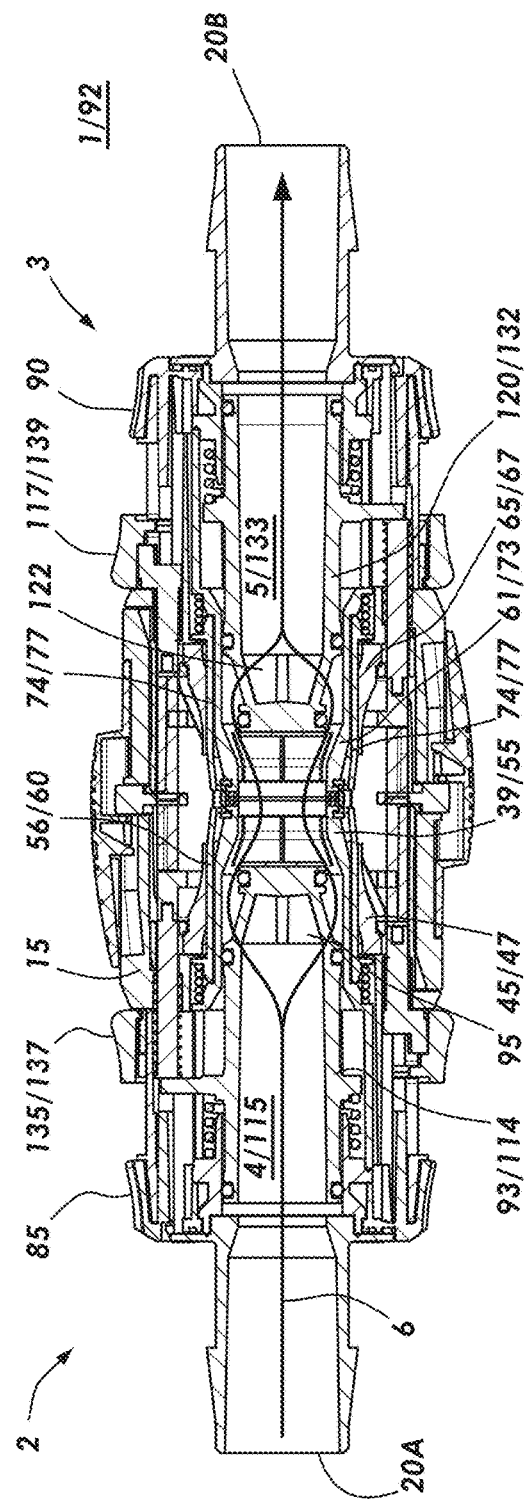
FIG. 4B
FIG. 4C

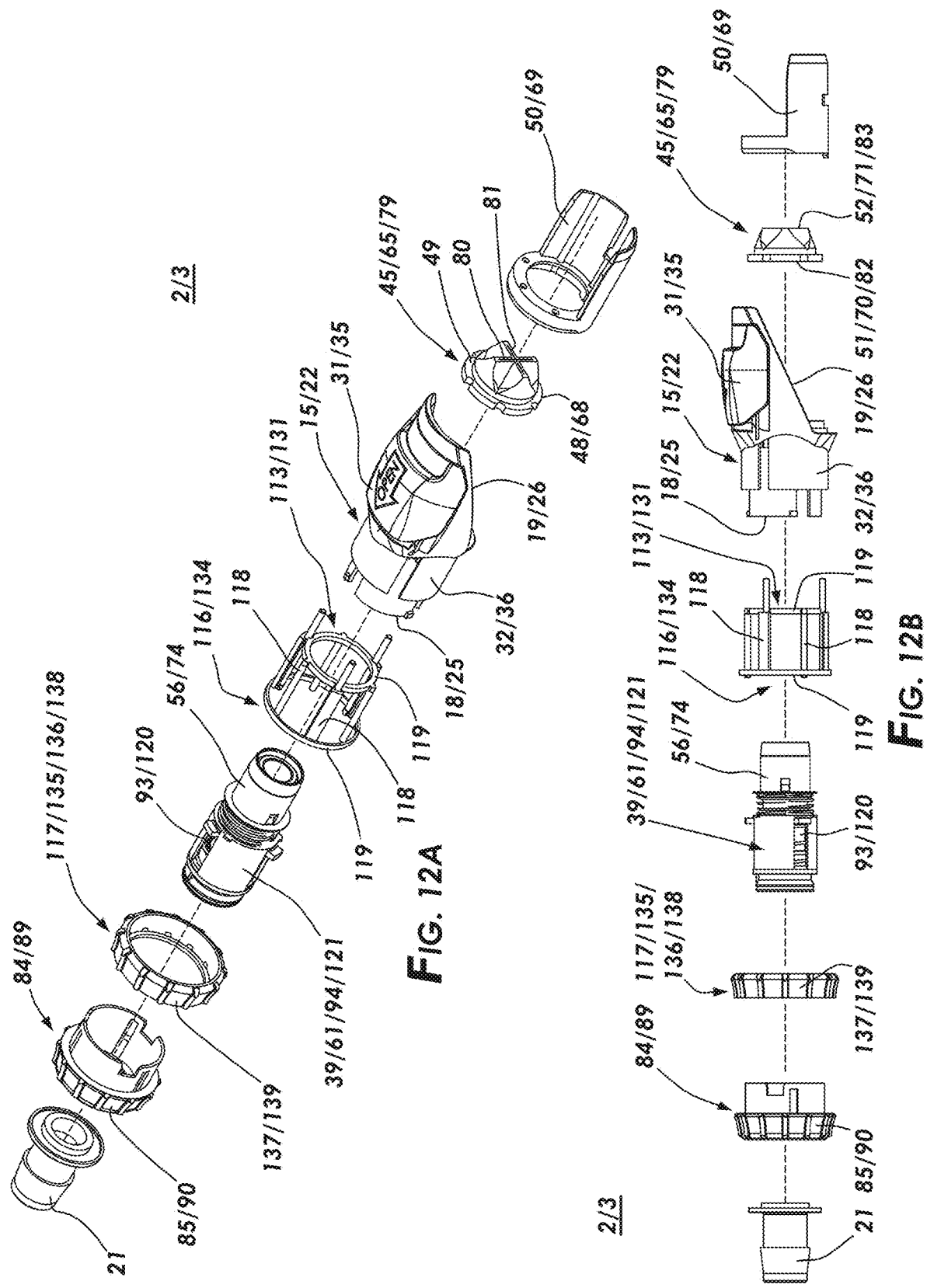

GENDERLESS ASEPTIC CONNECTOR

This United States Non-Provisional Patent Application claims the benefit of U.S. Provisional Patent Application No. 63/461,638, filed Apr. 25, 2023, hereby incorporated by reference herein.

I. SUMMARY OF THE INVENTION

A broad object of a particular embodiment of the invention can be to provide a connector system for releasably connecting together tubes, for example medical tubing, and methods of making and using such a connector system, whereby the connector system includes a first coupler including a first coupler passageway disposed therein, and a first coupler elastically deformable valve operable to seal the first coupler passageway from the external environment. The connector system further includes a second coupler including a second coupler passageway disposed therein, and a second coupler elastically deformable valve operable to seal the second coupler passageway from the external environment.

The first and second couplers can be substantially identical; thus, the couplers can be genderless, as opposed to a connector system comprising male and female couplers.

The connector system can further include a first coupler valve operable to interrupt fluid flow through the first coupler passageway, and a second coupler valve operable to interrupt fluid flow through the second coupler passageway. When in their default valve closed positions, a closed fluid flow path condition can be provided, thus precluding fluid flow through the connector system.

The connector system can further include a first coupler driver operable to forcibly urge the first coupler valve toward a first coupler valve open position which provides a first coupler passageway open condition that permits fluid to flow through the first coupler passageway, and a second coupler driver operable to forcibly urge the second coupler valve toward a second coupler valve open position which provides a second coupler passageway open condition that permits fluid to flow through the second coupler passageway. When in their passageway open conditions, an open fluid flow path condition can be provided which permits fluid to flow through the connector system.

Naturally, further objects of the invention are disclosed throughout other areas of the specification, drawings, and claims.

II. A BRIEF DESCRIPTION OF THE DRAWINGS

FIG. 1B is an end view of the particular embodiment of the connector system shown in FIG. 1A.

FIG. 1C is a cross-sectional view of the connector system shown in FIG. 1B.

FIG. 2B is an end view of the particular embodiment of the connector system shown in FIG. 2A.

FIG. 2C is a cross-sectional view of the connector system shown in FIG. 2B.

FIG. 3B is an end view of the particular embodiment of the connector system shown in FIG. 3A.

FIG. 3C is a cross-sectional view of the connector system shown in FIG. 3B.

FIG. 4B is an end view of the particular embodiment of the connector system shown in FIG. 4A.

FIG. 4C is a cross-sectional view of the connector system shown in FIG. 4B.

Figure 8A:
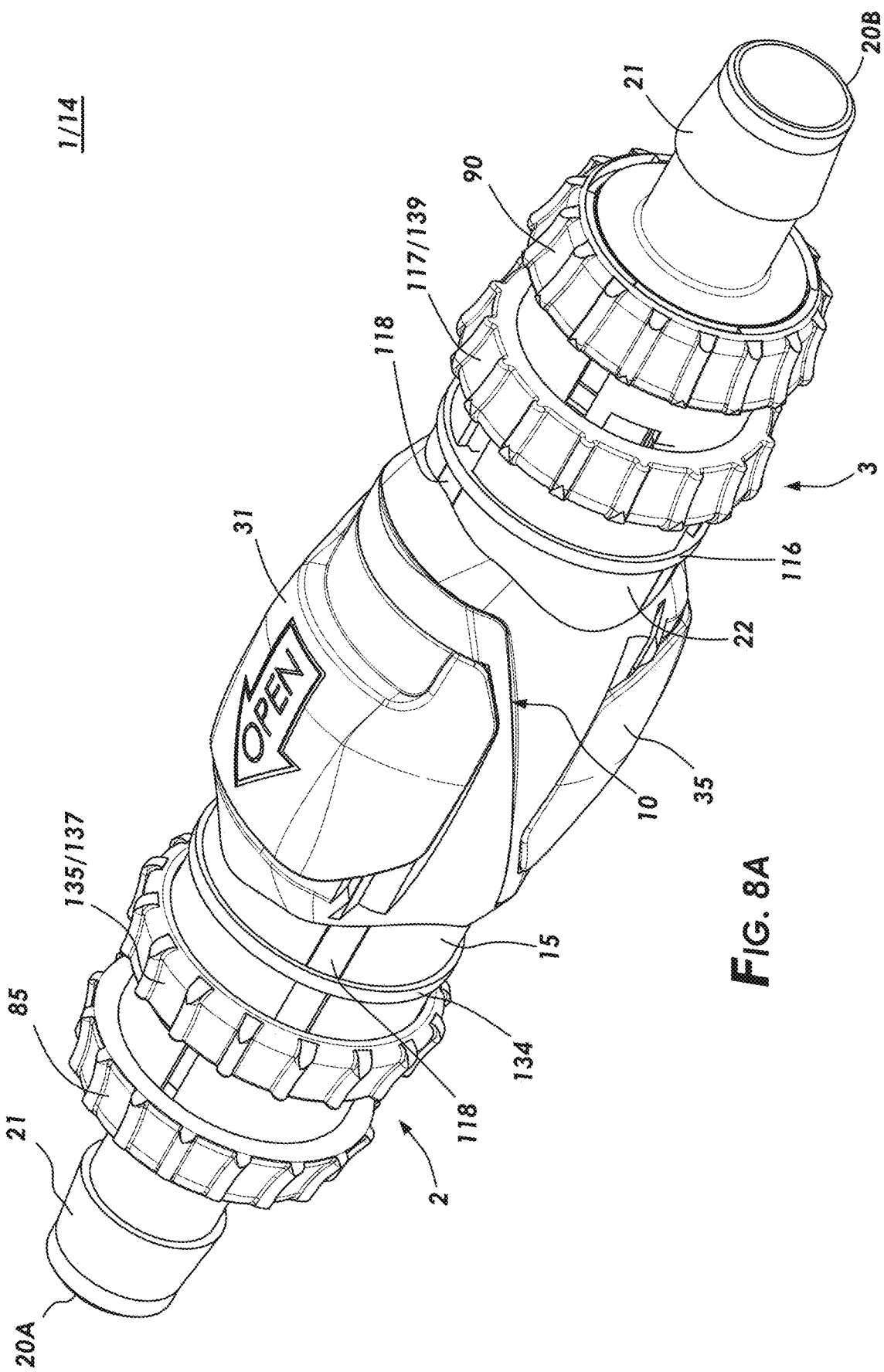
FIG. 8A is a perspective view of the particular embodiment of the connector system shown in FIGS. 7A through 7E, but whereby the first and second couplers are releasably connected to achieve a coupler connected condition.
Figure 8B:
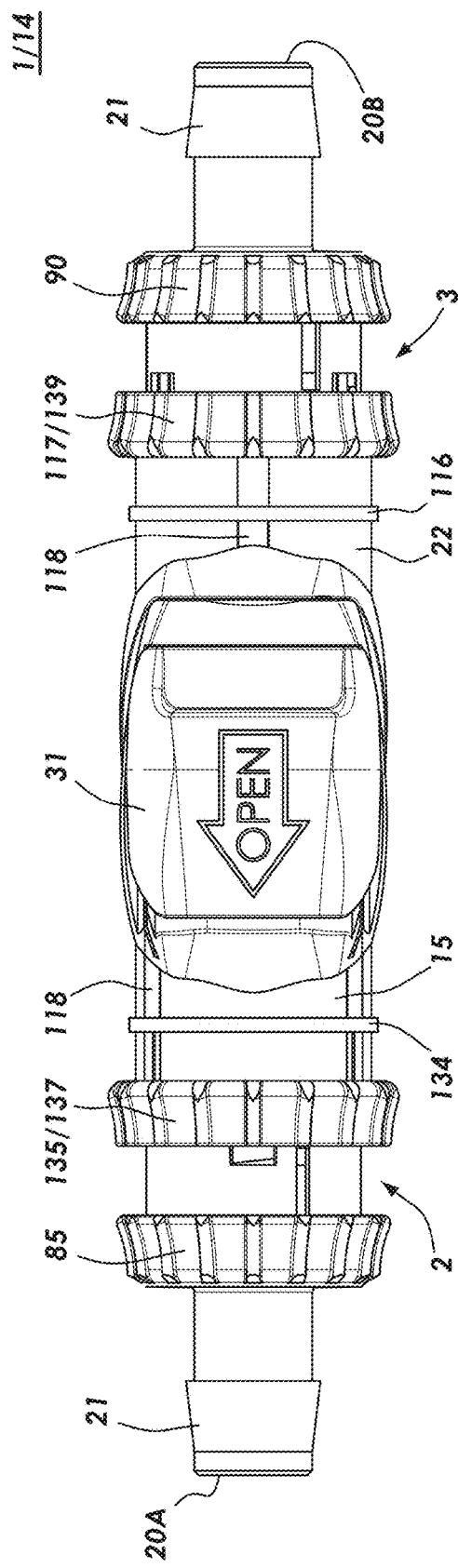
FIG. 8B is a top view of the particular embodiment of the connector system shown in FIG. 8A.
Figure 8C:
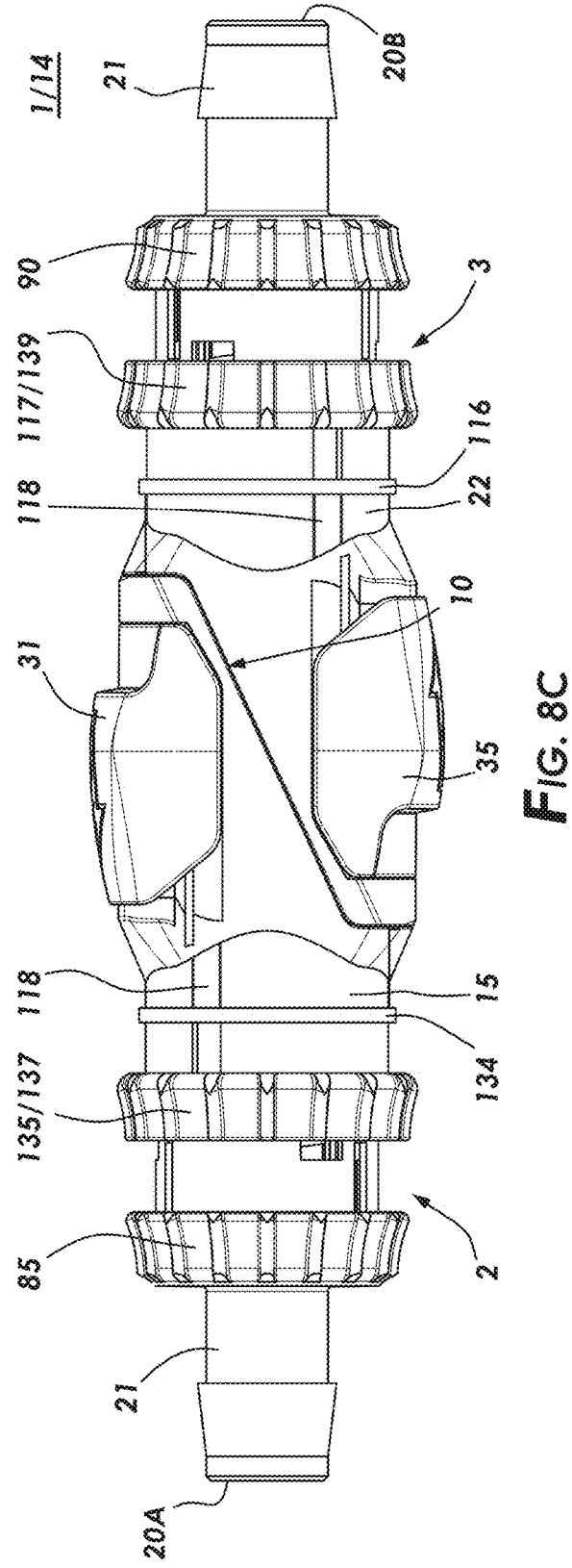
FIG. 8C is a side view of the particular embodiment of the connector system shown in FIG. 8A.
Figure 8D:
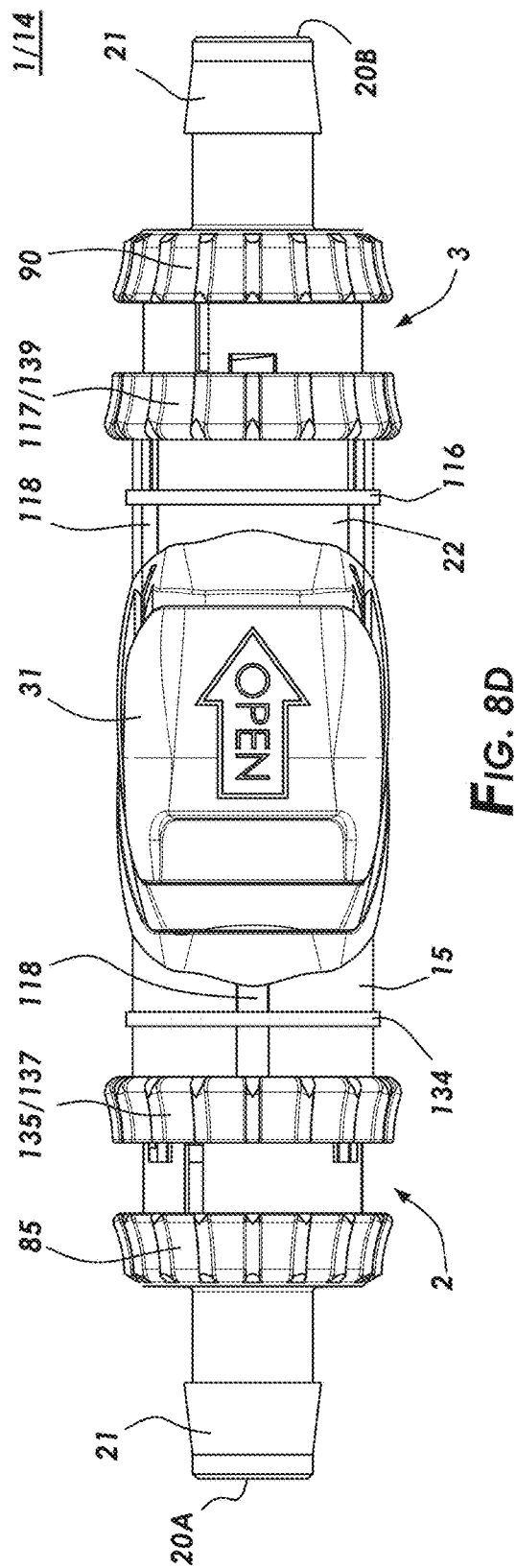
FIG. 8D is a bottom view of the particular embodiment of the connector system shown in FIG. 8A.
Figure 8E:
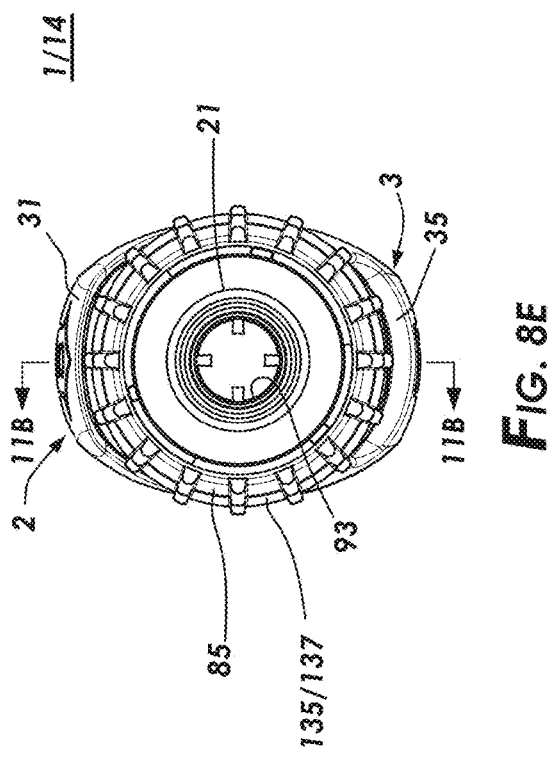
FIG. 8E is an end view of the particular embodiment of the connector system shown in FIG. 8A.
Figure 9A:
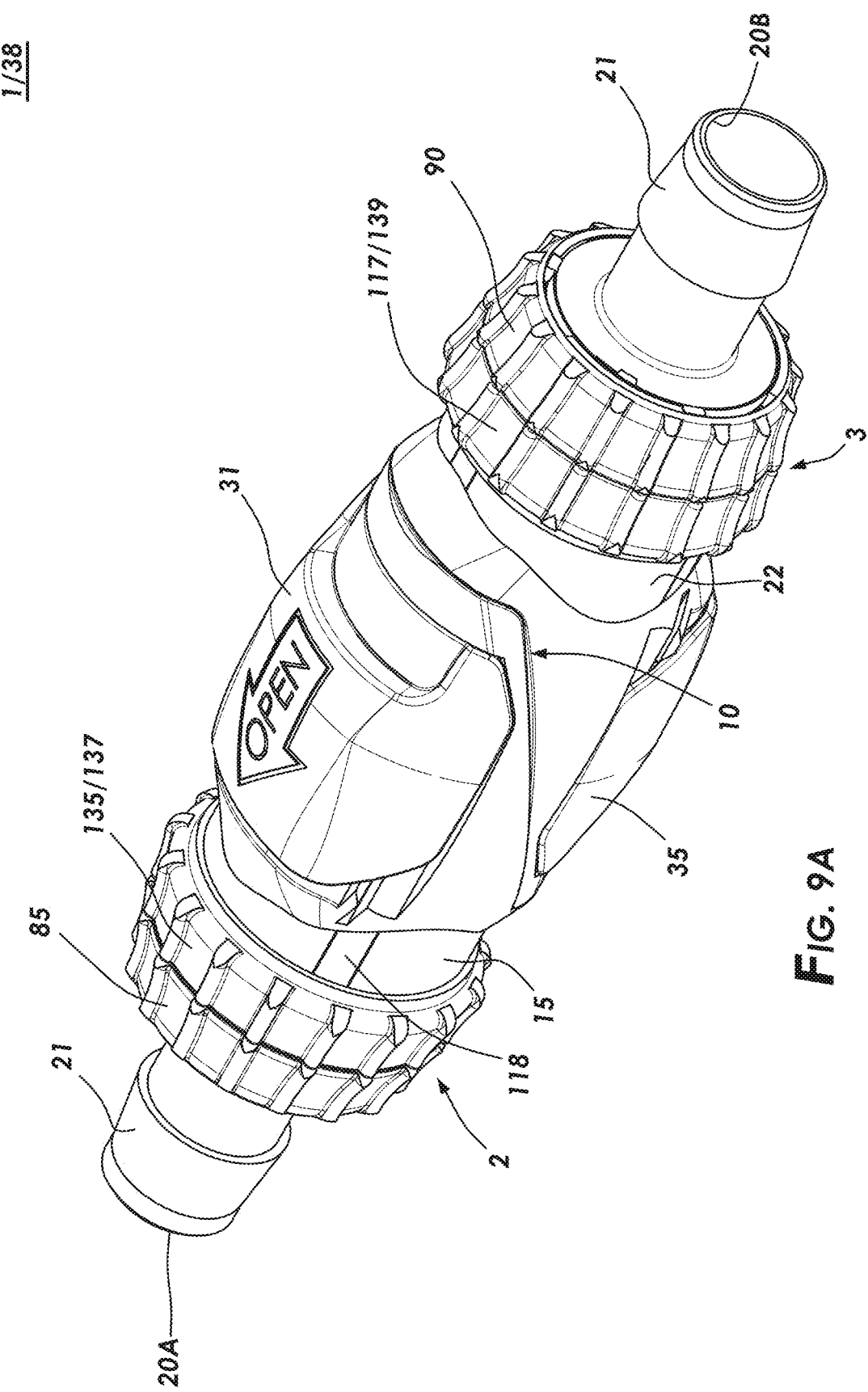

FIG. 9A is a perspective view of the particular embodiment of the connector system shown in FIGS. 8A through 8E, but whereby a first passageway of the first coupler is sealably engaged with a second passageway of the second coupler to provide a passageway connected condition; the first and second passageways are interrupted by respective valves, consequently resulting in a closed fluid flow path condition.

Figure 9B:
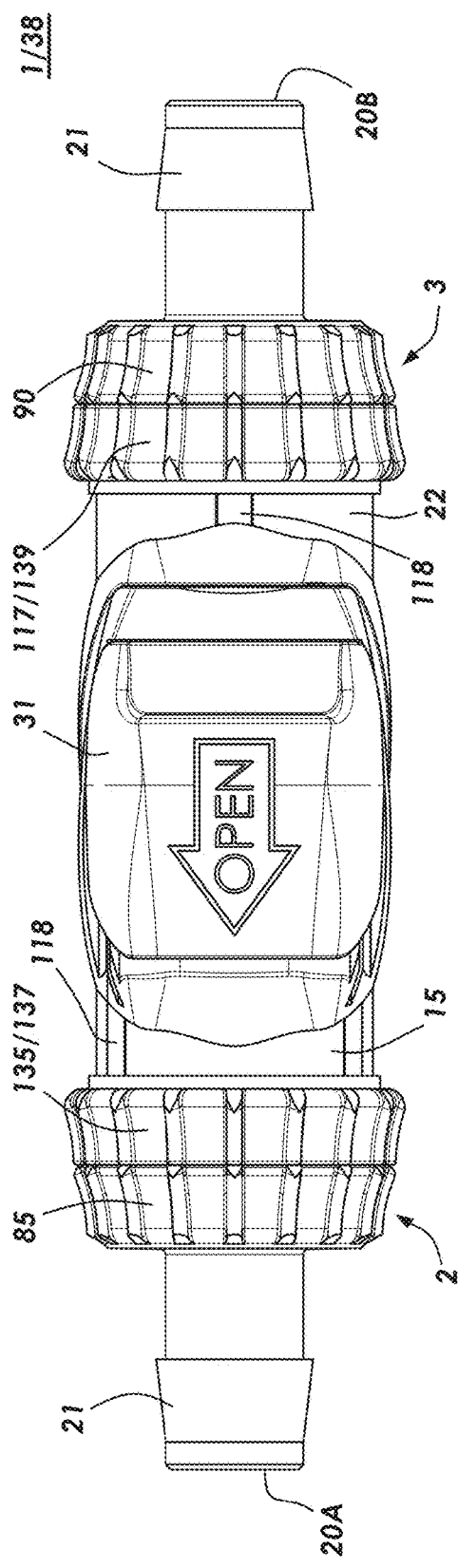

FIG. 9B is a top view of the particular embodiment of the connector system shown in FIG. 9A.

Figure 9C:
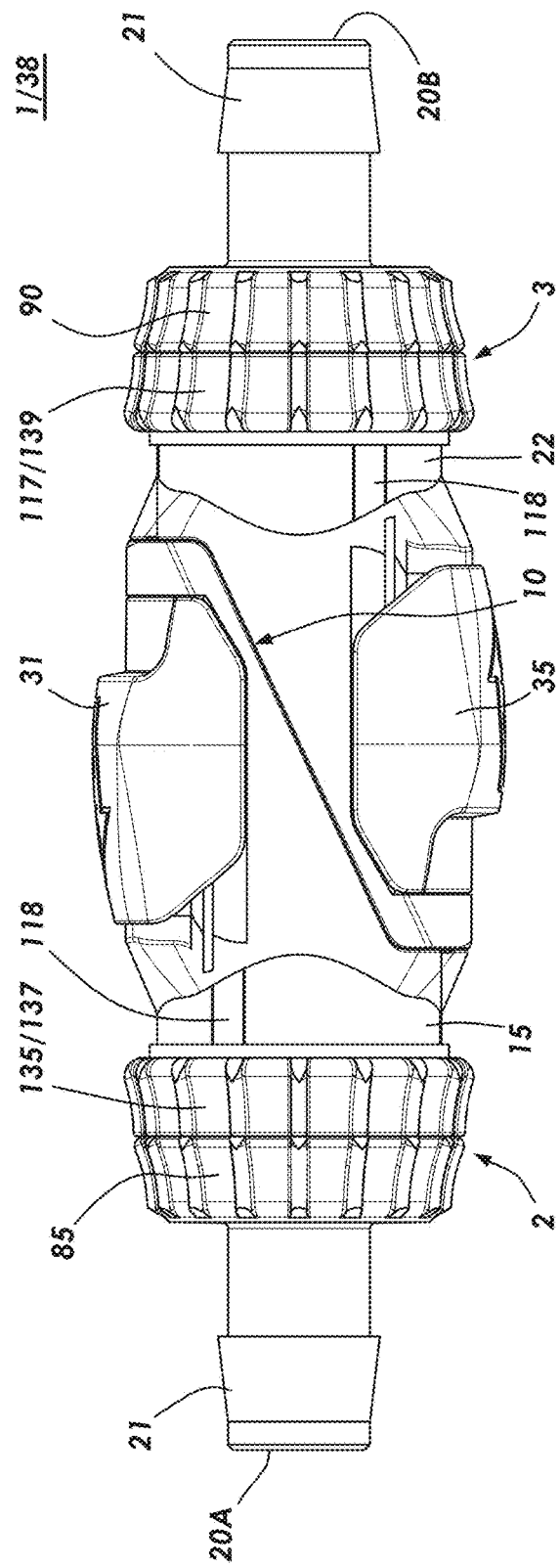

FIG. 9C is a side view of the particular embodiment of the connector system shown in FIG. 9A.

Figure 9D:
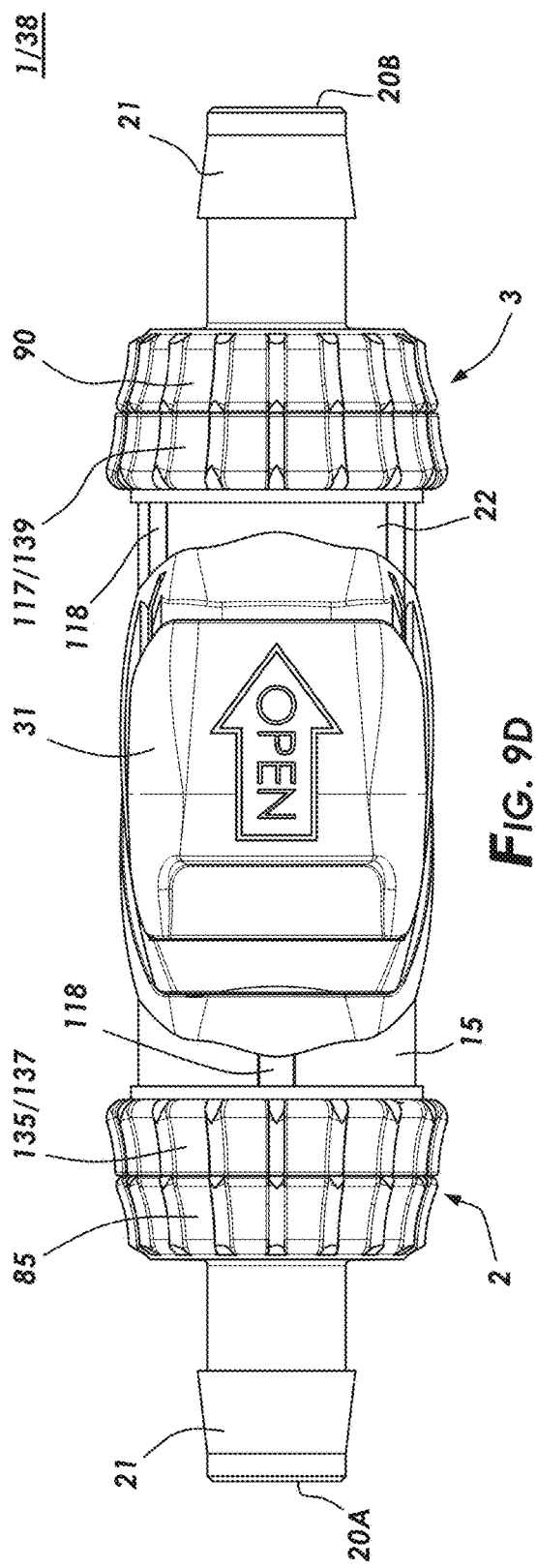

FIG. 9D is a bottom view of the particular embodiment of the connector system shown in FIG. 9A.

Figure 9E:
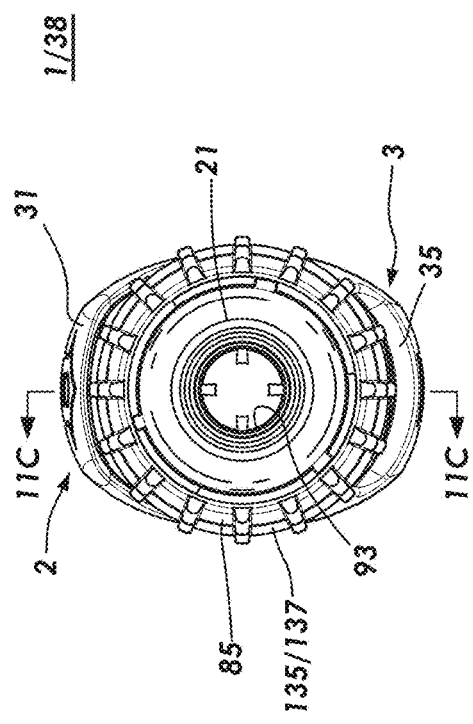

FIG. 9E is an end view of the particular embodiment of the connector system shown in FIG. 9A.

Figure 10A:
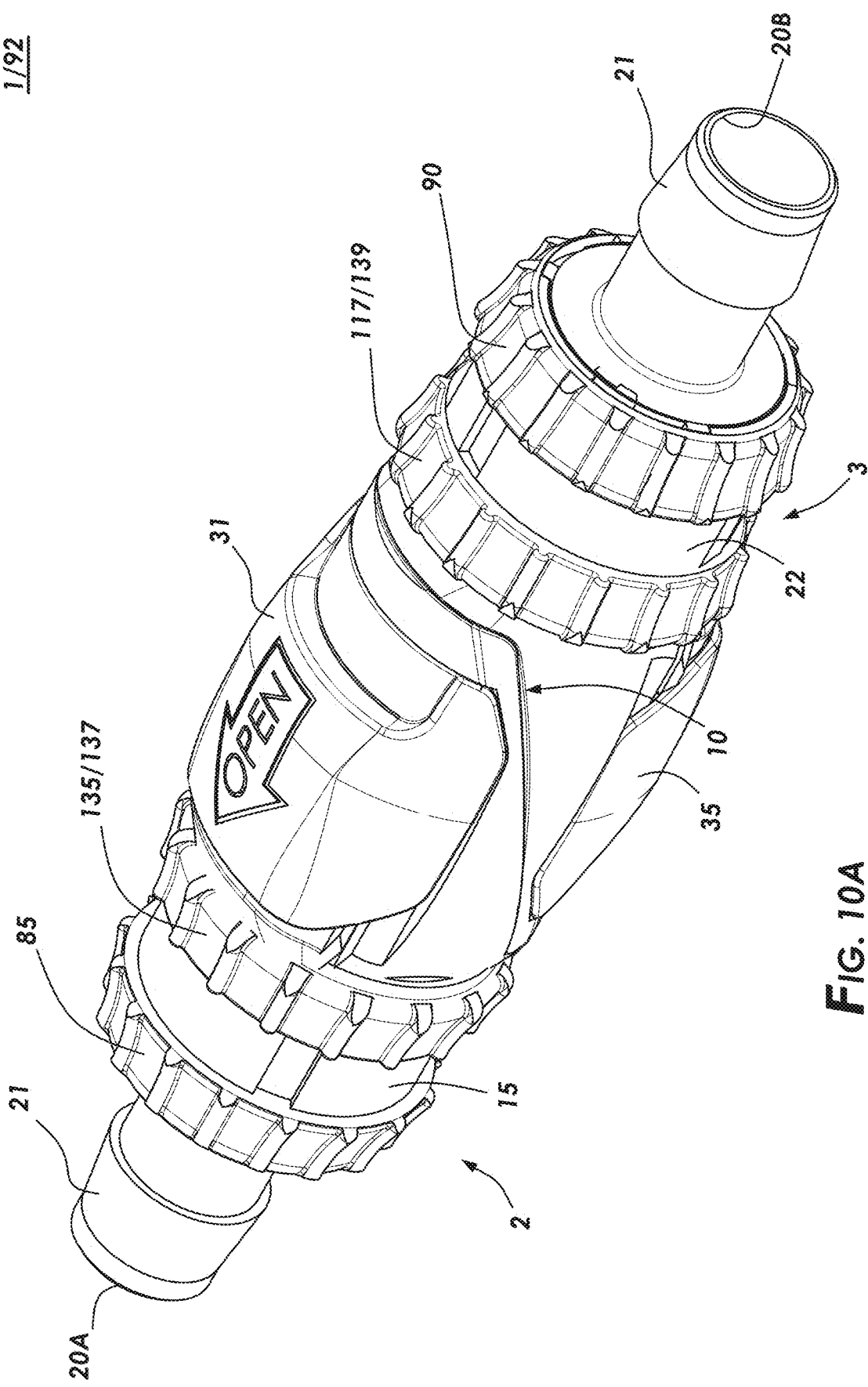

FIG. 10A is a perspective view of the particular embodiment of the connector system shown in FIGS. 9A through 9E, but whereby the first and second passageways are uninterrupted to provide an open fluid flow path condition in which fluid can flow through the connector system.

Figure 10B:
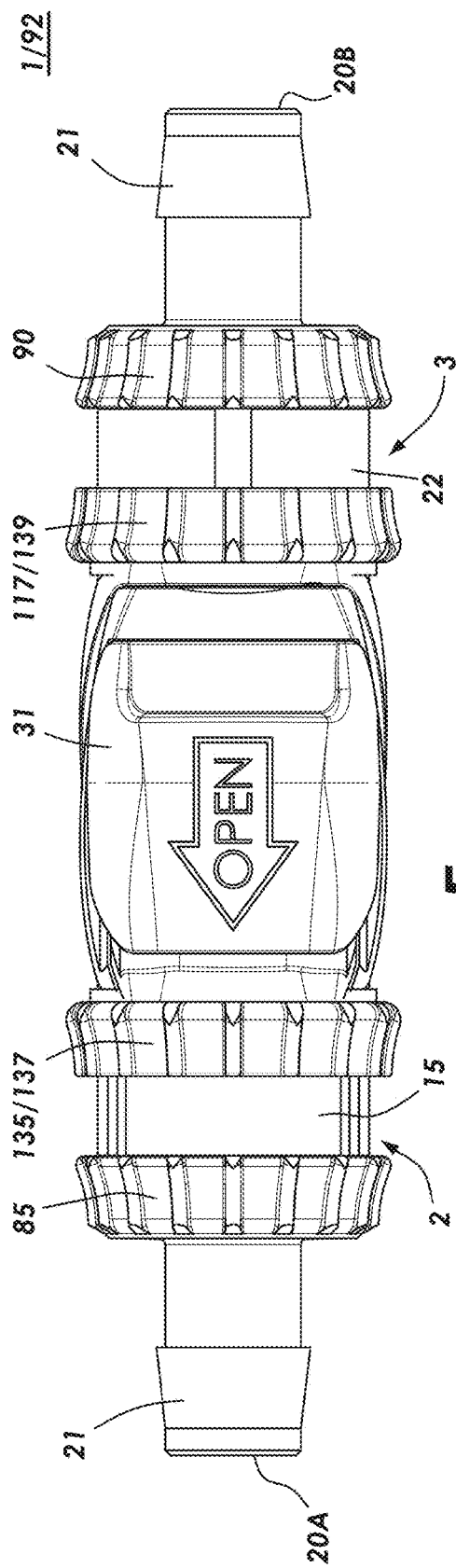

FIG. 10B is a top view of the particular embodiment of the connector system shown in FIG. 10A.

Figure 10C:
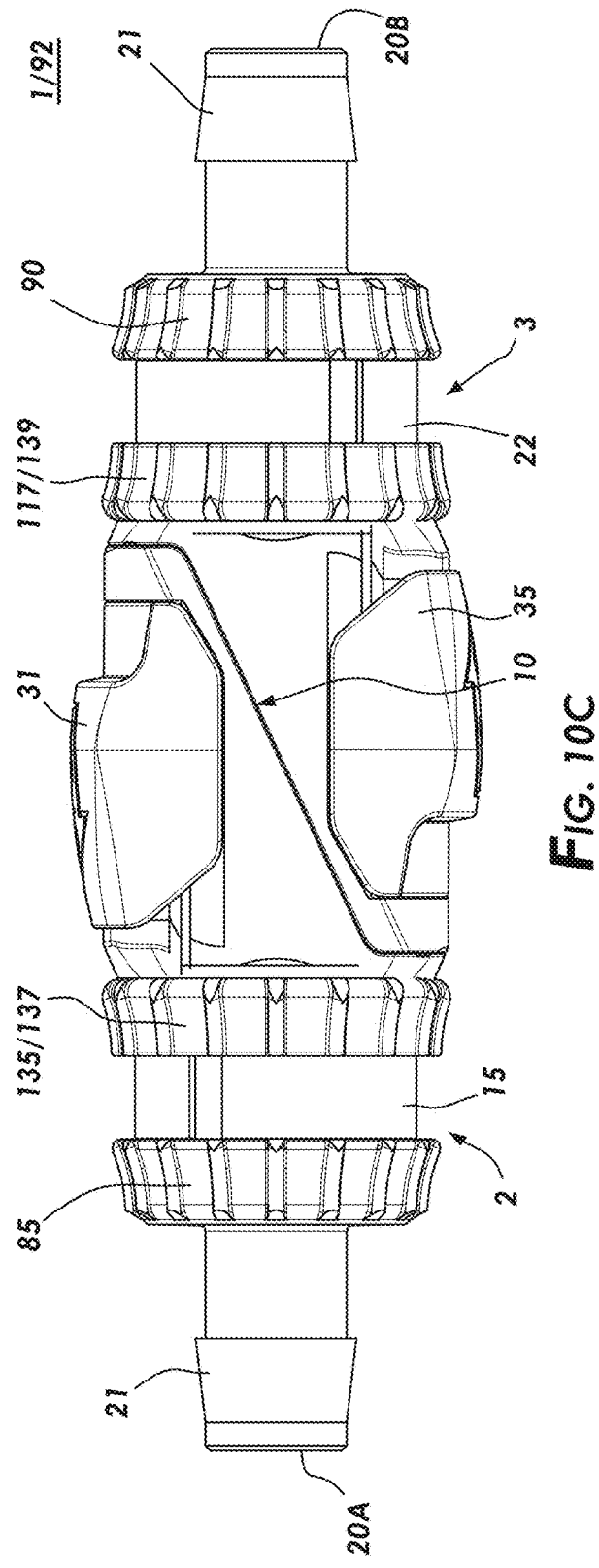

FIG. 10C is a side view of the particular embodiment of the connector system shown in FIG. 10A.

Figure 10D:
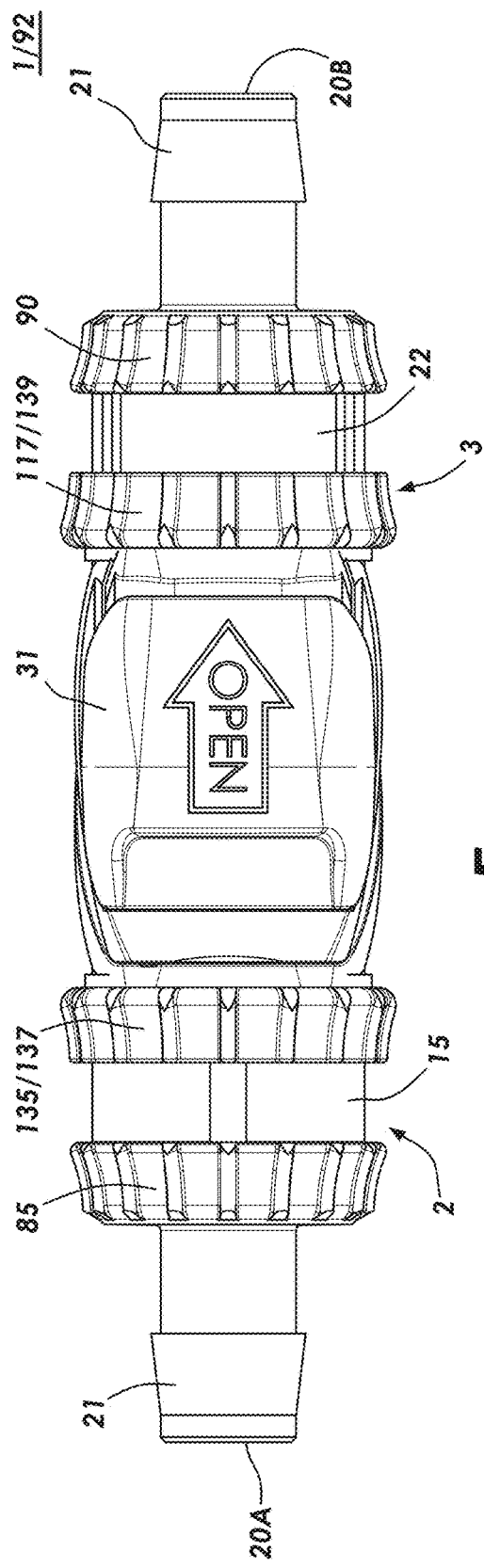

FIG. 10D is a bottom view of the particular embodiment of the connector system shown in FIG. 10A.

Figure 10E:
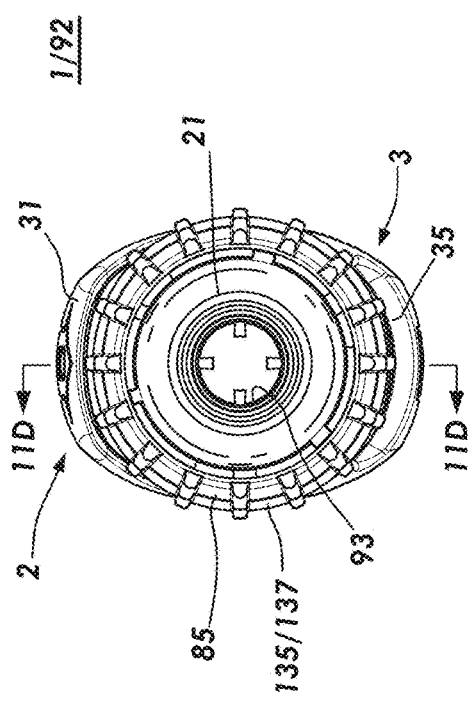

FIG. 10E is an end view of the particular embodiment of the connector system shown in FIG. 10A.

Figure 1A:
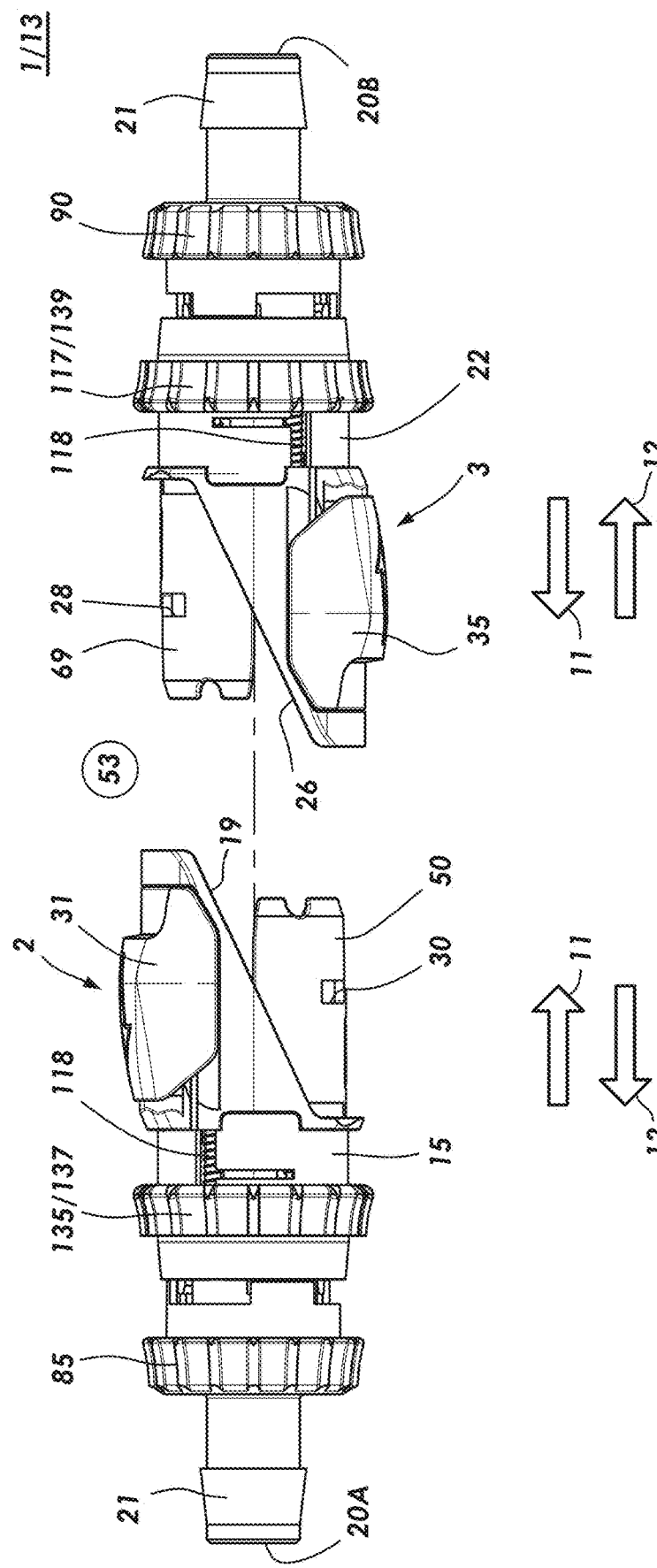
FIG. 1A is a side view of a particular embodiment of the connector system.
Figure 2A:
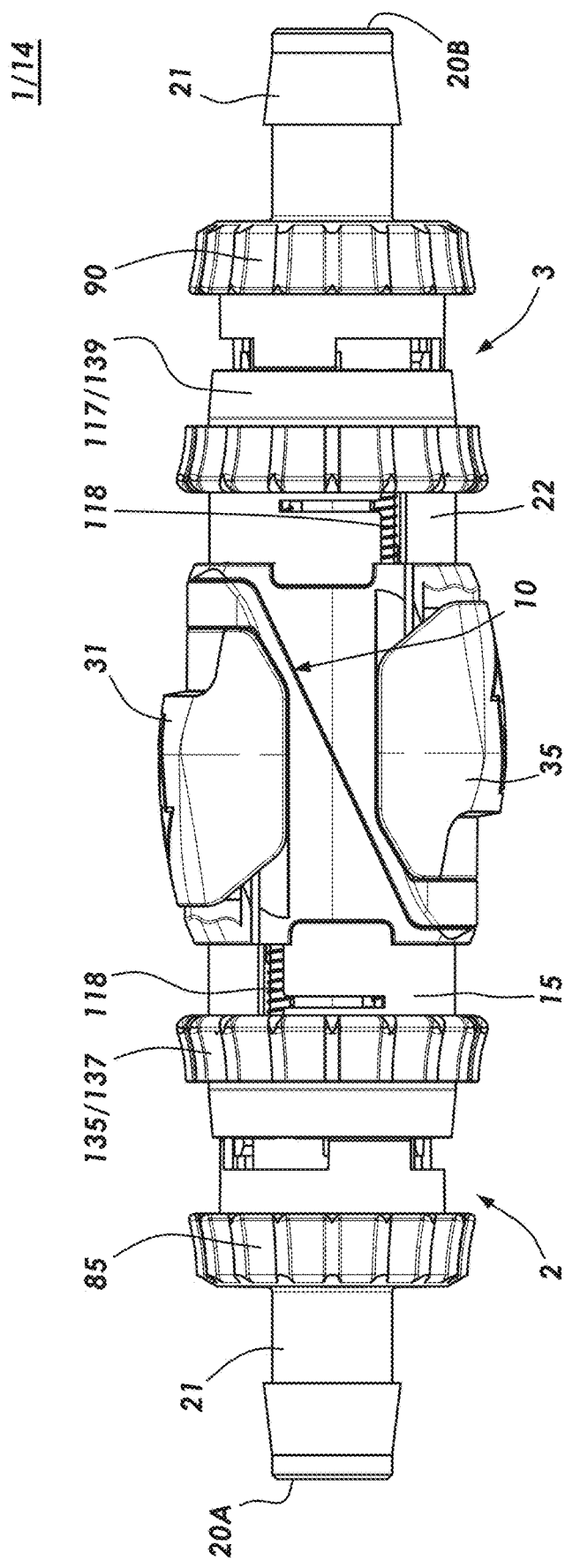
FIG. 2A is a side view of a particular embodiment of the connector system.
Figure 3A:
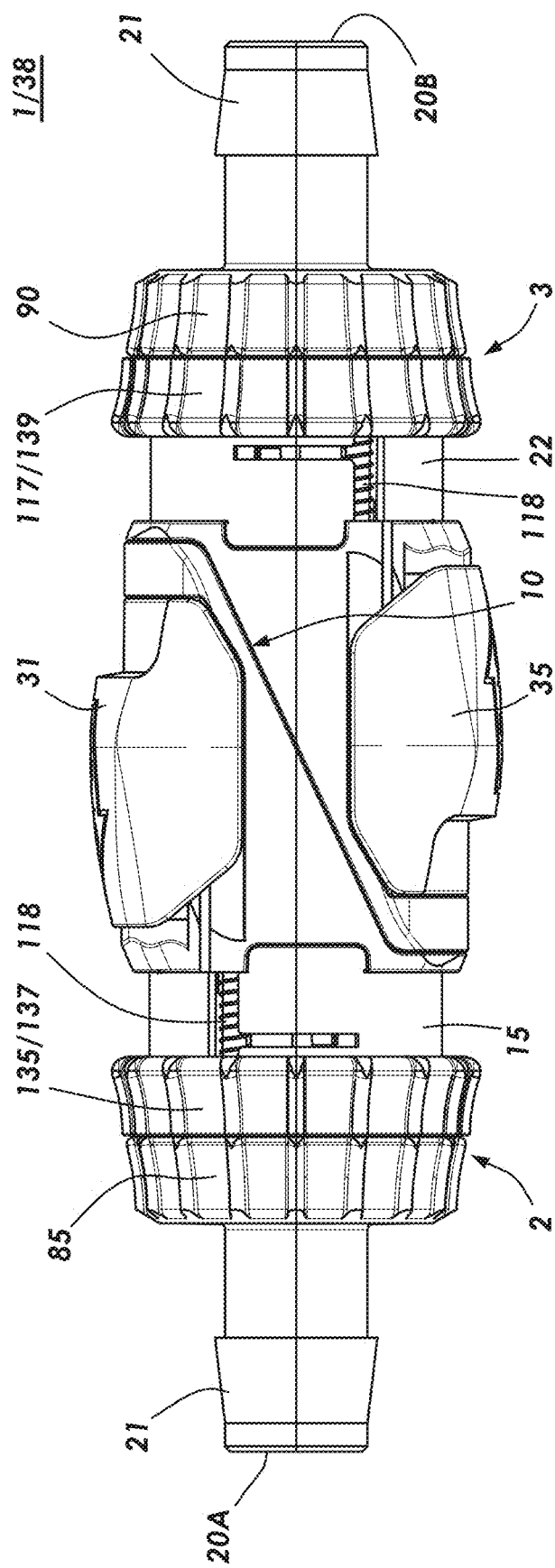
FIG. 3A is a side view of a particular embodiment of the connector system.
Figure 4A:
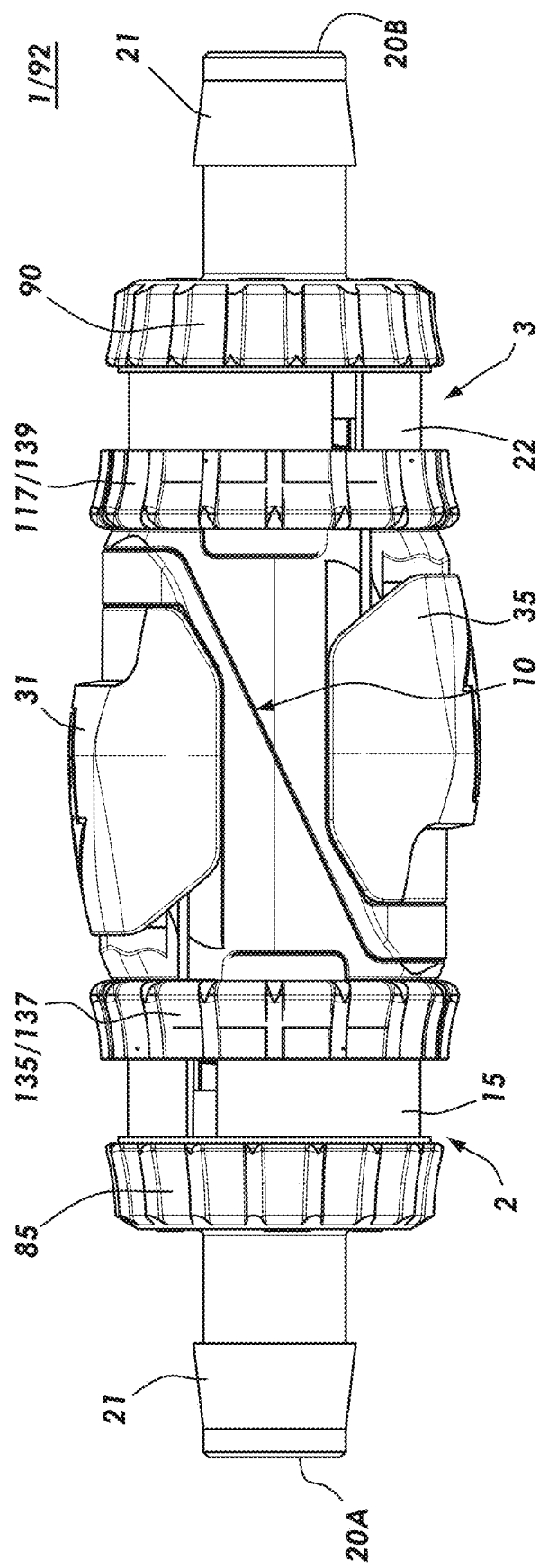
FIG. 4A is a side view of a particular embodiment of the connector system.
Figure 5A:
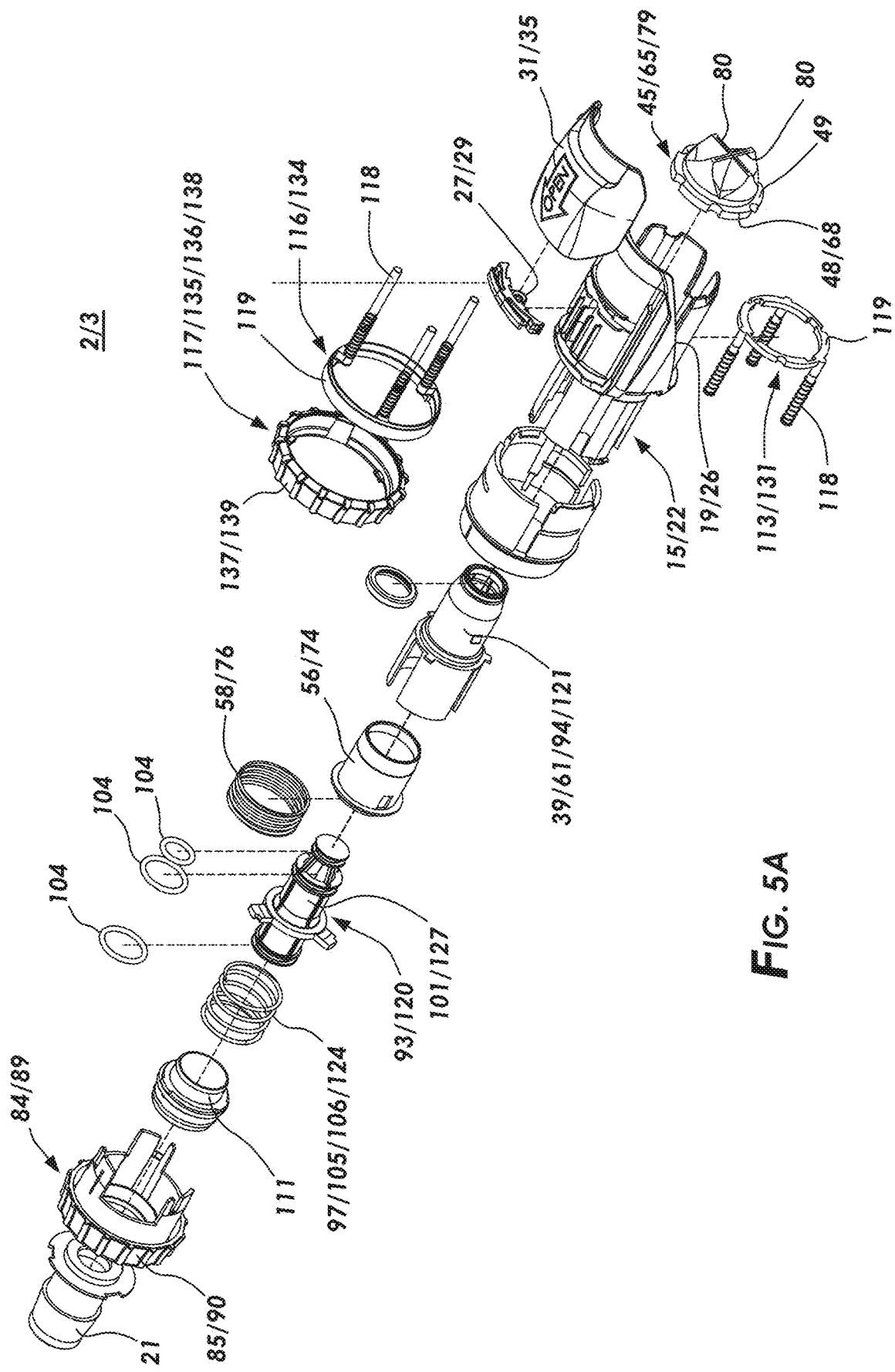
FIG. 5A is an exploded perspective view of a particular embodiment of one of the two substantially identical couplers of the connector system shown in FIGS. 1A through 4C.
Figure 5B:
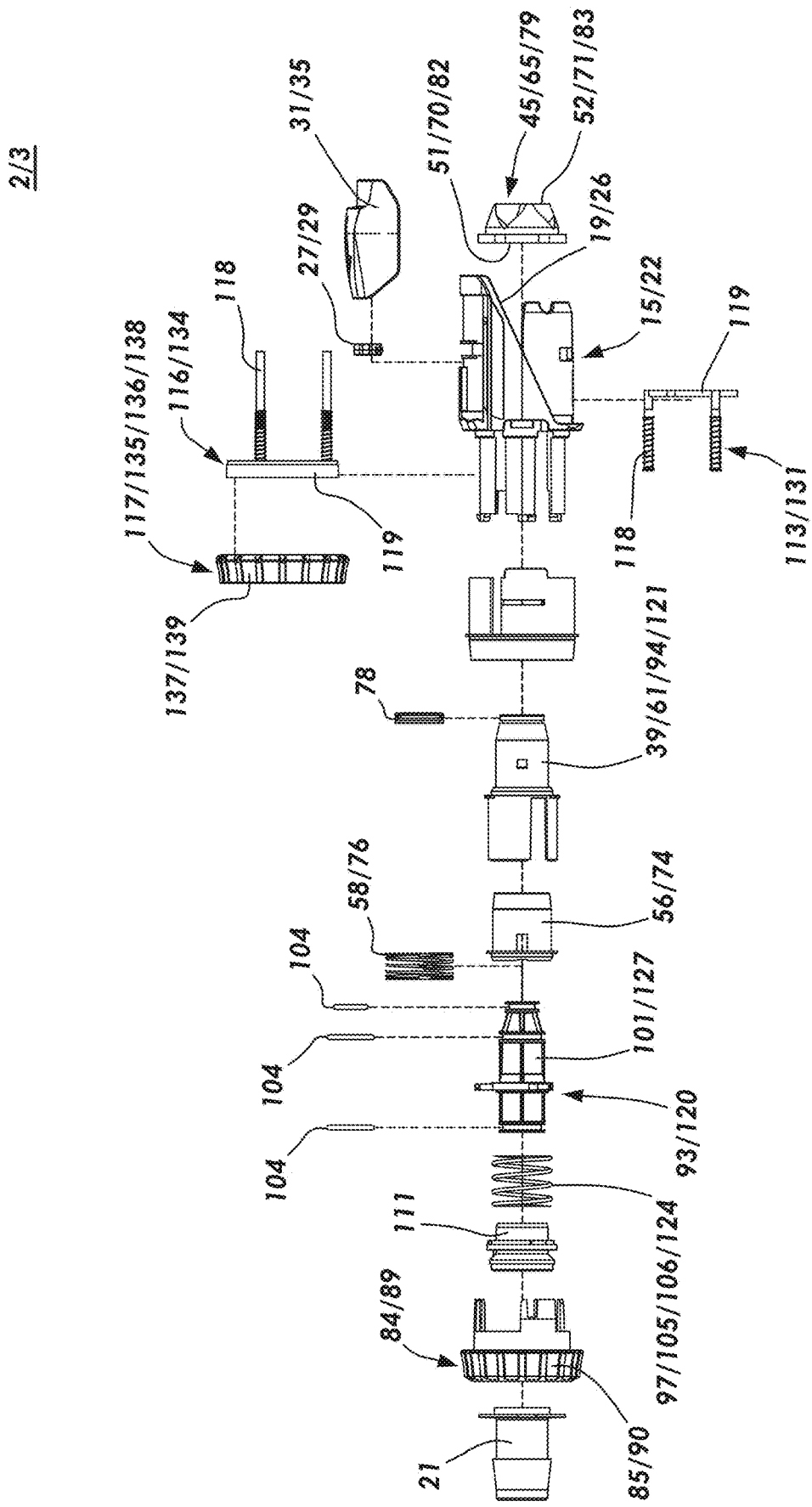
FIG. 5B is an exploded side view of the particular embodiment of the coupler shown in FIG. 5A.
Figure 6A:
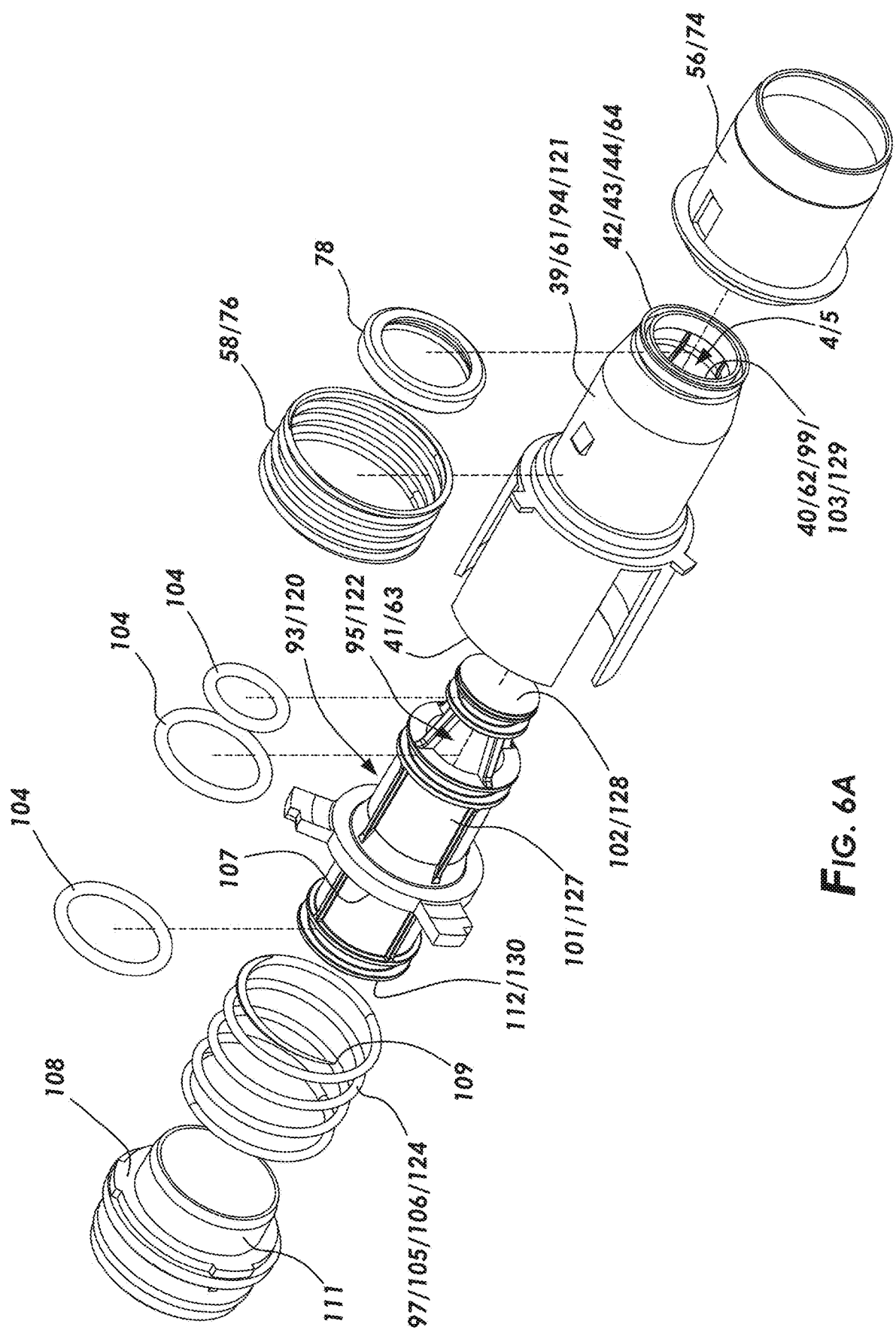
FIG. 6A is an exploded perspective view of a particular embodiment of a conduit, a valve, and a sleeve of one of the two substantially identical couplers of the connector system shown in FIGS. 1A through 4C.
Figure 6B:
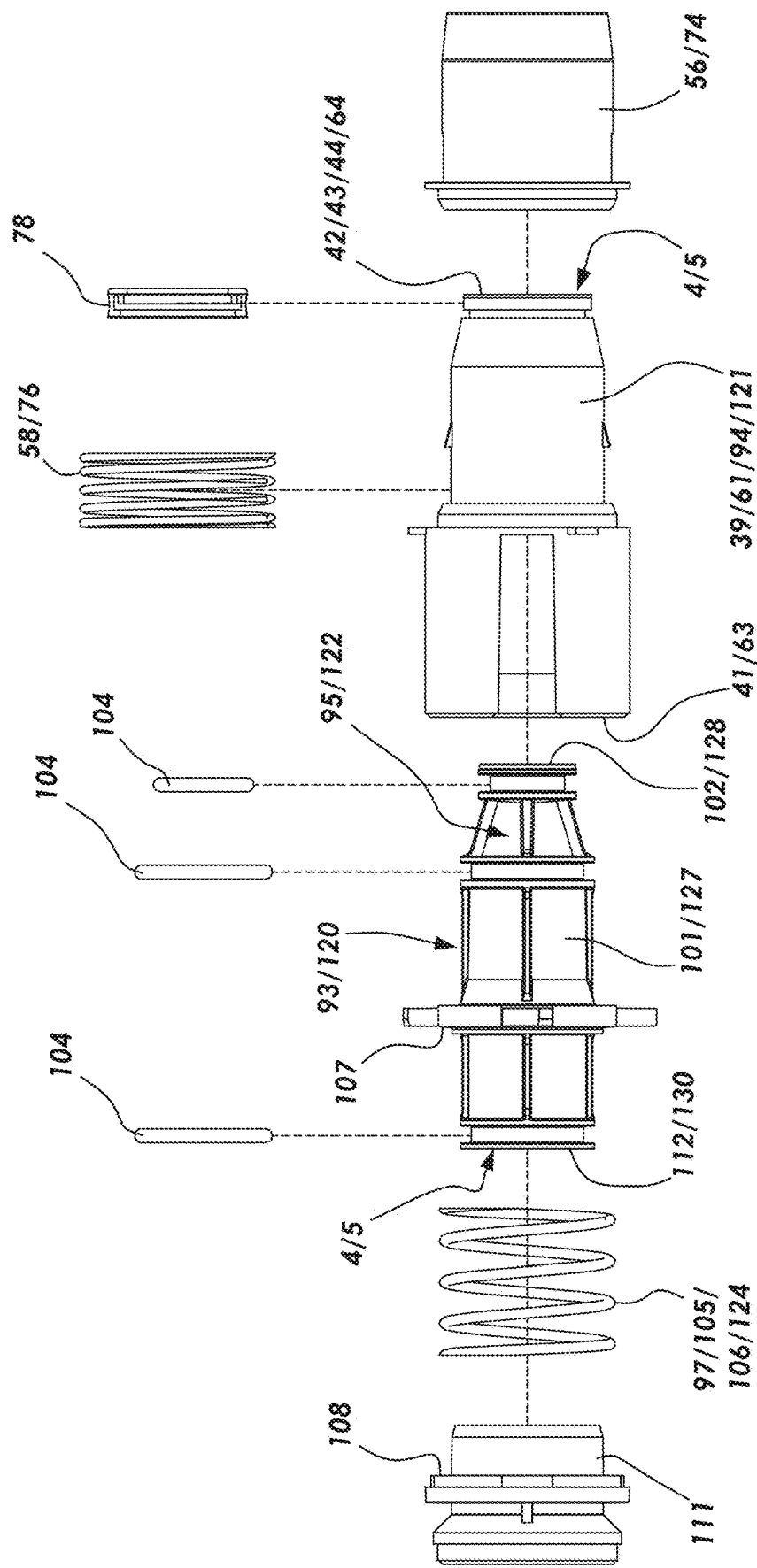
FIG. 6B is an exploded side view of the particular embodiment of the conduit, the valve, and the sleeve shown in FIG. 6A.
Figure 7A:
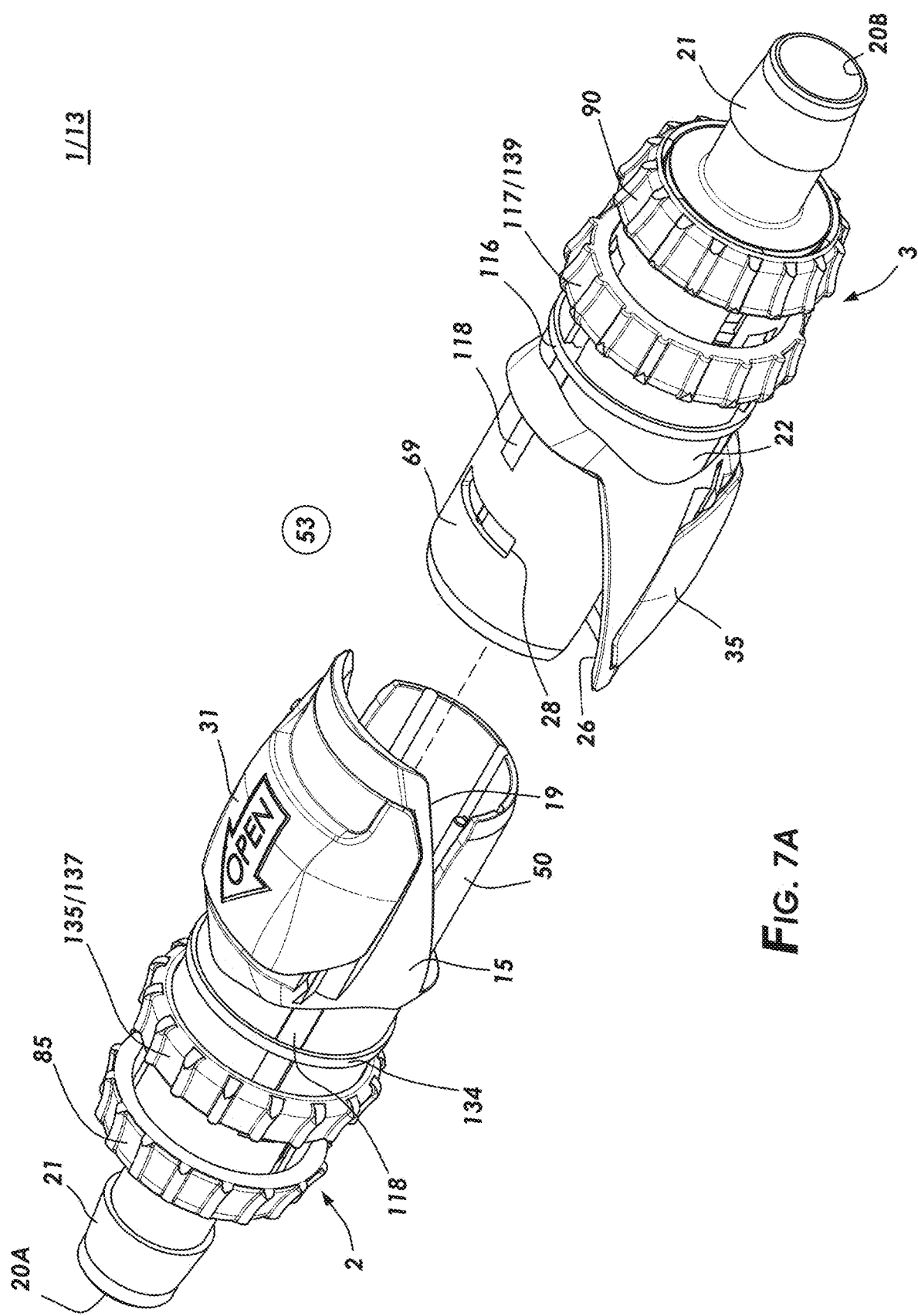
FIG. 7A is a perspective view of a particular embodiment of the connector system, whereby first and second couplers dispose in adjacent axial relation but are not releasably connected, thus the first and second couplers are in a coupler disconnected condition.
Figure 7B:
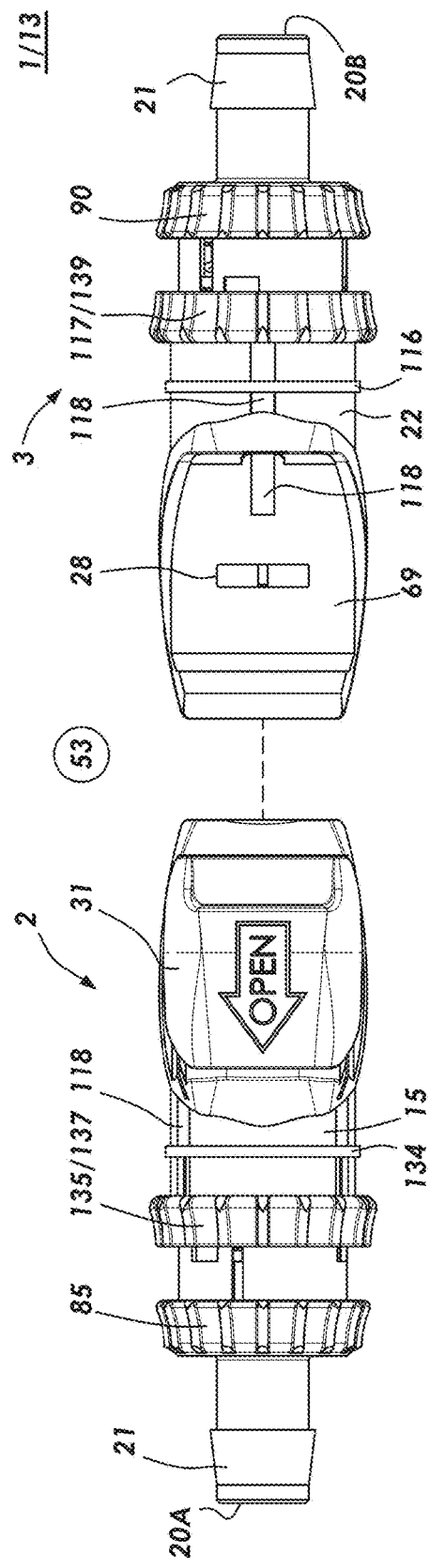
FIG. 7B is a top view of the particular embodiment of the connector system shown in FIG. 7A.
Figure 7C:
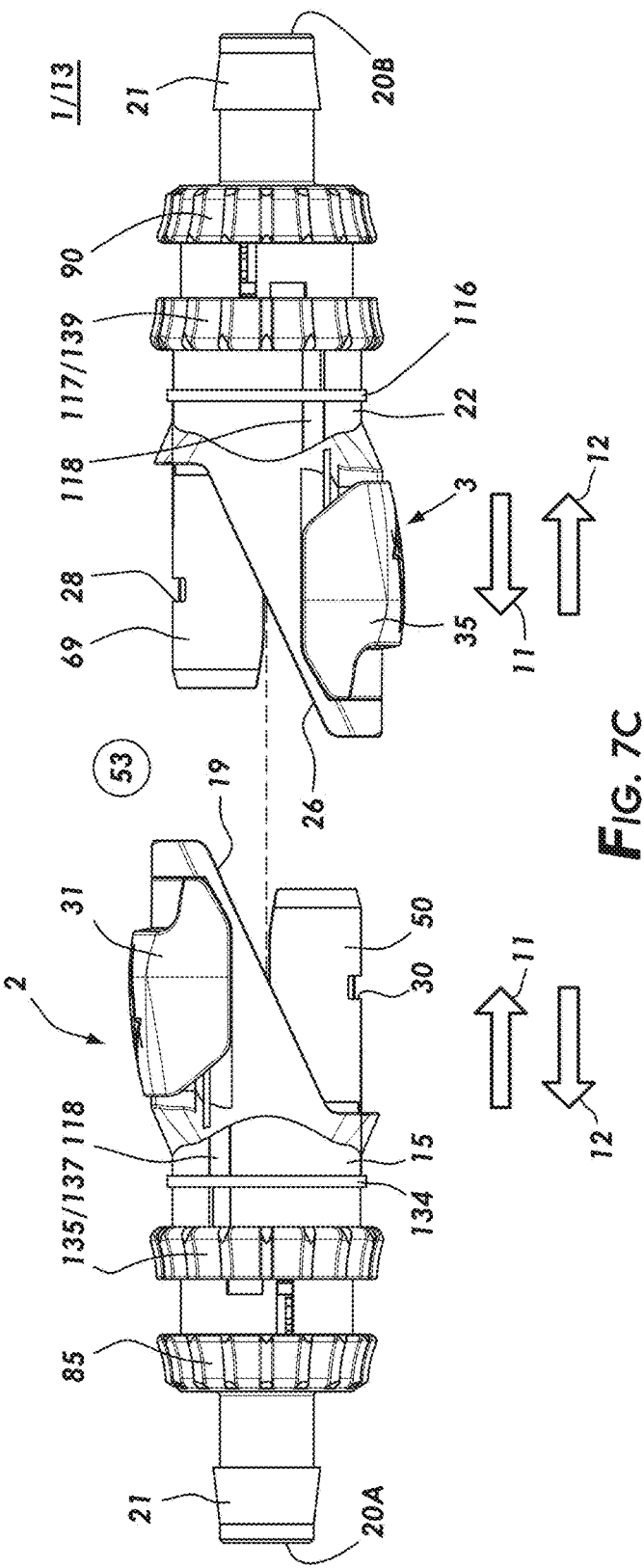
FIG. 7C is a side view of the particular embodiment of the connector system shown in FIG. 7A.
Figure 7D:
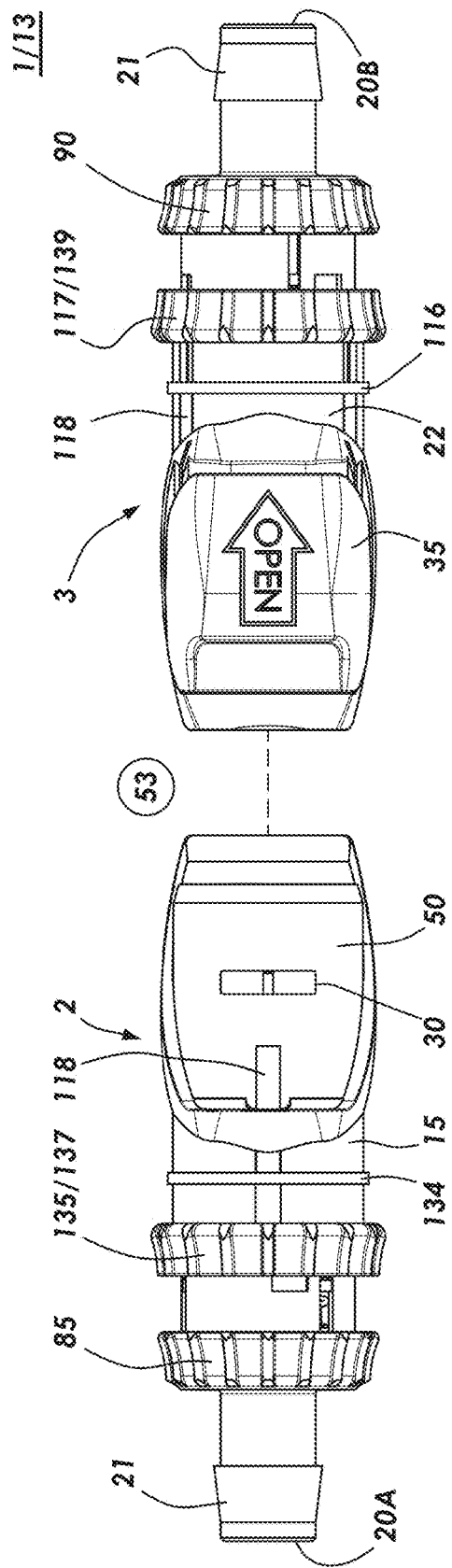
FIG. 7D is a bottom view of the particular embodiment of the connector system shown in FIG. 7A.
Figure 7E:
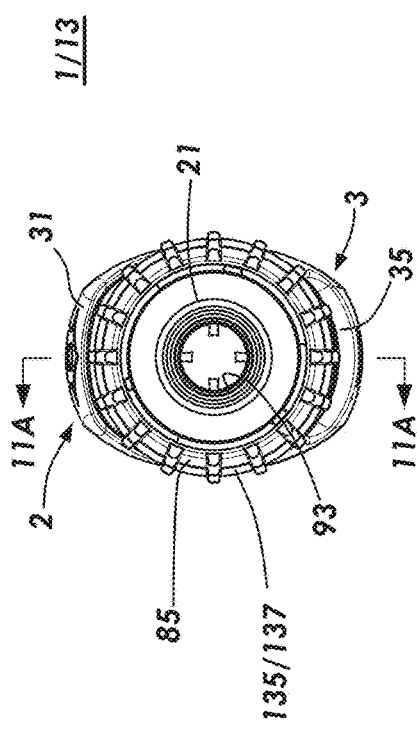
FIG. 7E is an end view of the particular embodiment of the connector system shown in FIG. 7A.
Figure 11A:
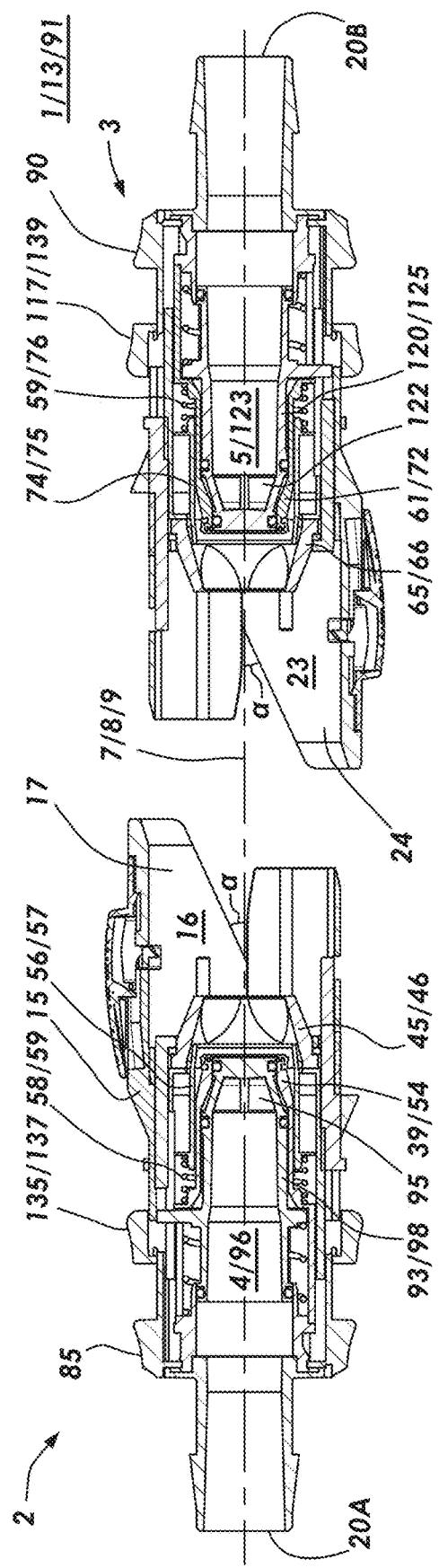

FIG. 11A is a cross-sectional view of the connector system shown in FIG. 7E.

Figure 11B:
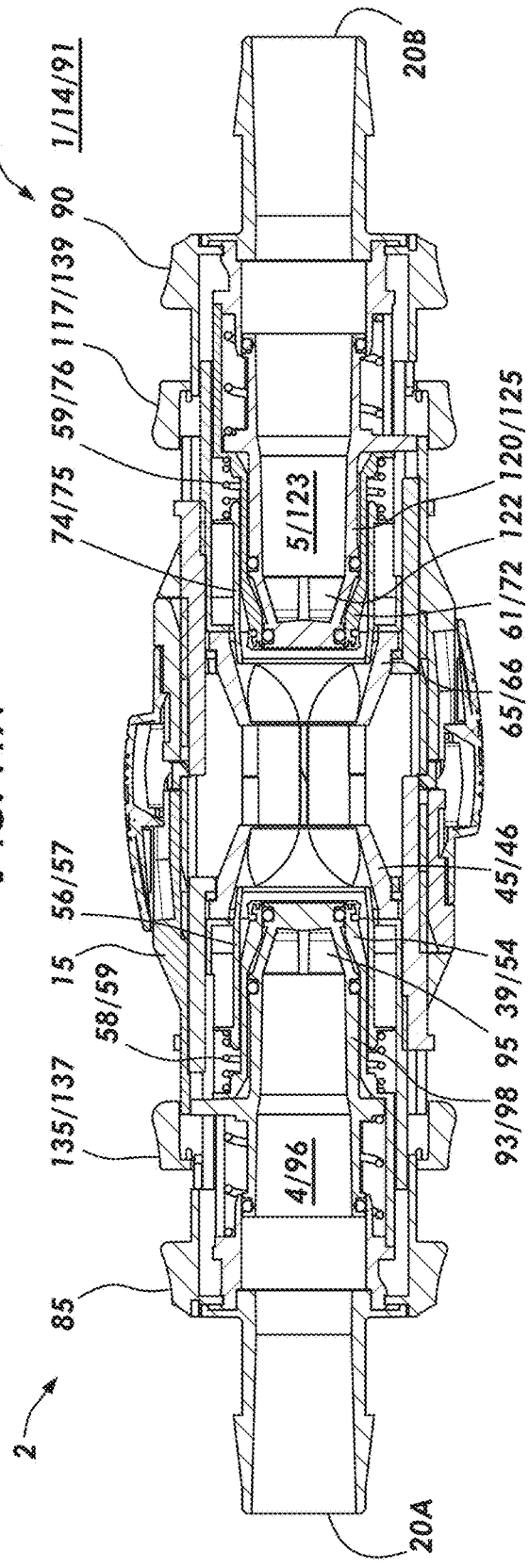

FIG. 11B is a cross-sectional view of the connector system shown in FIG. 8E.

Figure 11C:
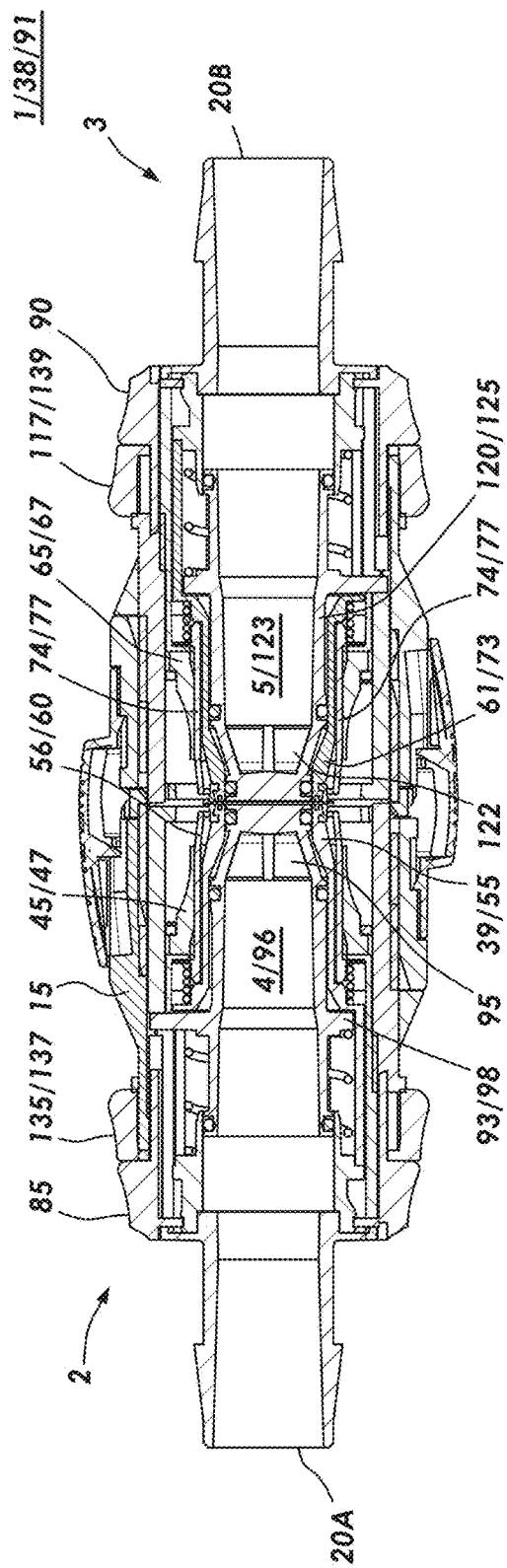

FIG. 11C is a cross-sectional view of the connector system shown in FIG. 9E.

Figure 11D:
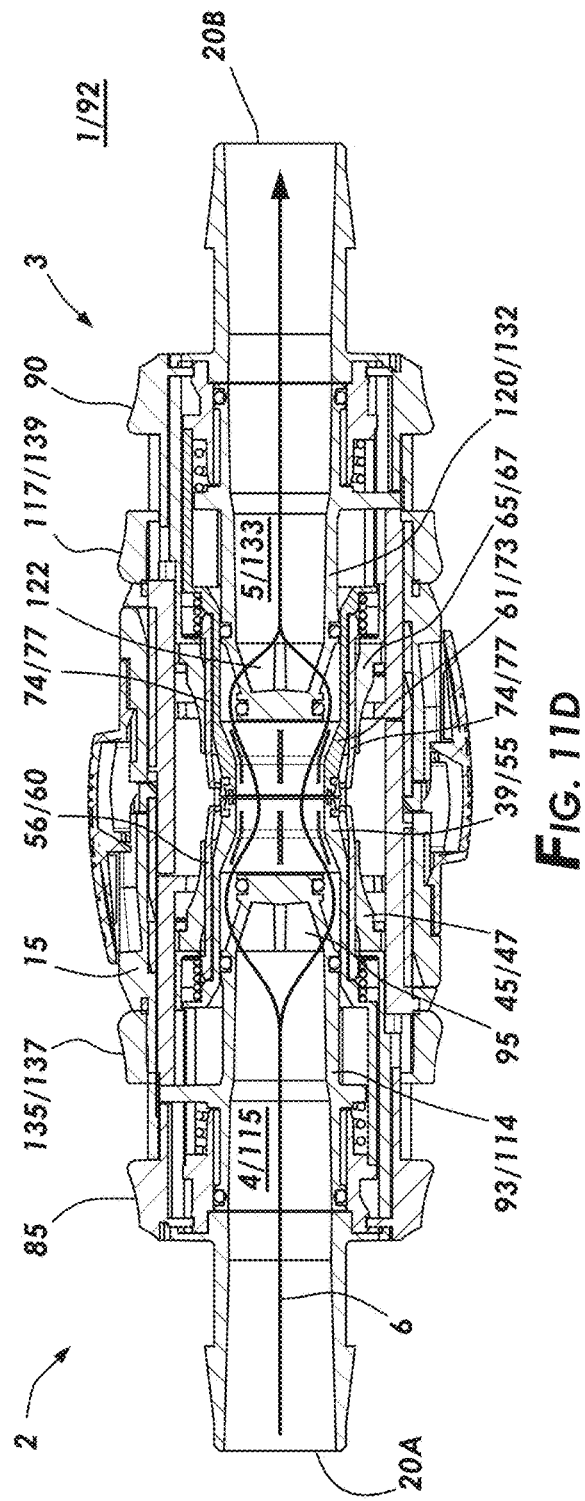

FIG. 11D is a cross-sectional view of the connector system shown in FIG. 10E.

FIG. 12A is an exploded perspective view of a particular embodiment of one of the two substantially identical couplers of the connector system shown in FIGS. 7A through 11D.

FIG. 12B is an exploded side view of the particular embodiment of the coupler shown in FIG. 12A.

Figure 13A:
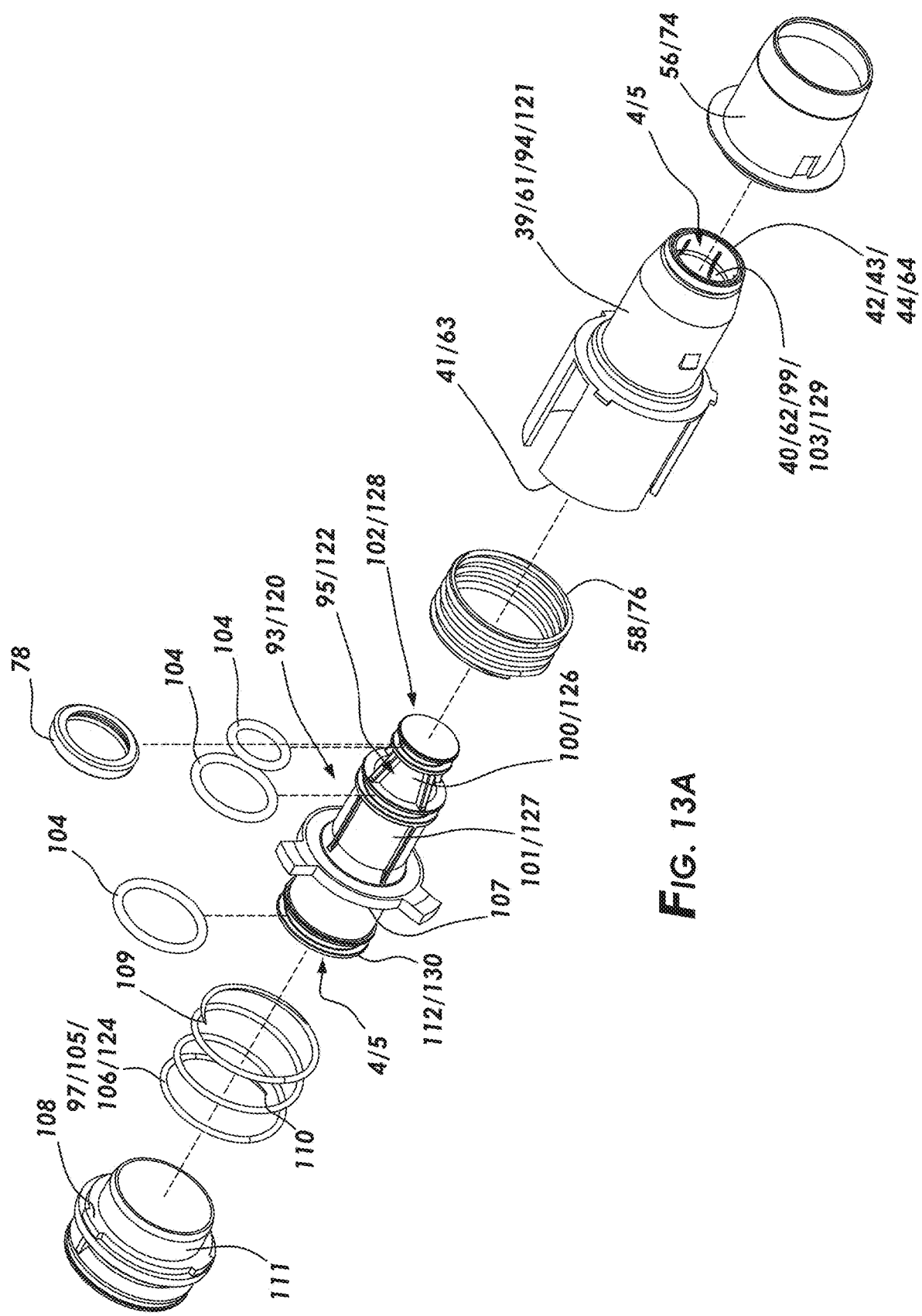

FIG. 13A is an exploded perspective view of a particular embodiment of a conduit, a valve, and a sleeve of one of the two substantially identical couplers of the connector system shown in FIGS. 7A through 11D.

Figure 13B:
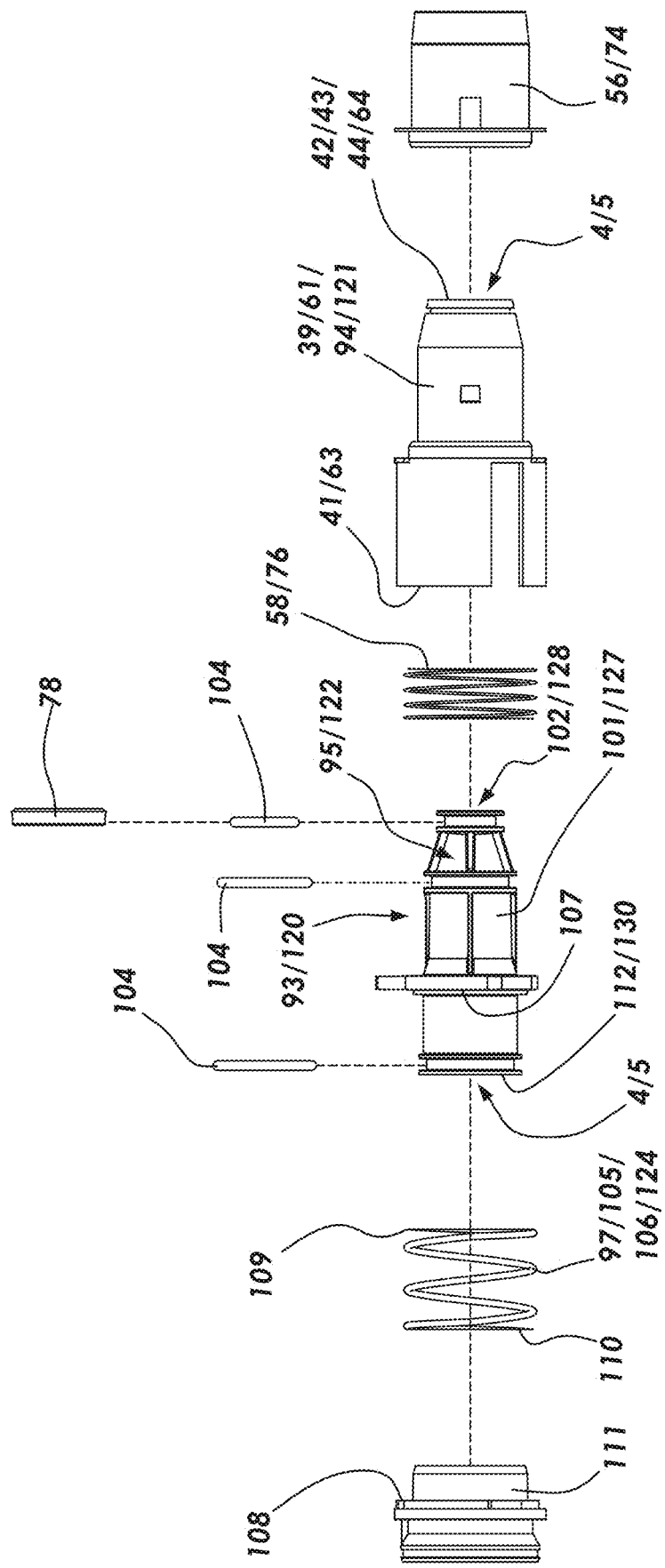

FIG. 13B is an exploded side view of the particular embodiment of the conduit, the valve, and the sleeve shown in FIG. 13A.

Figure 14:
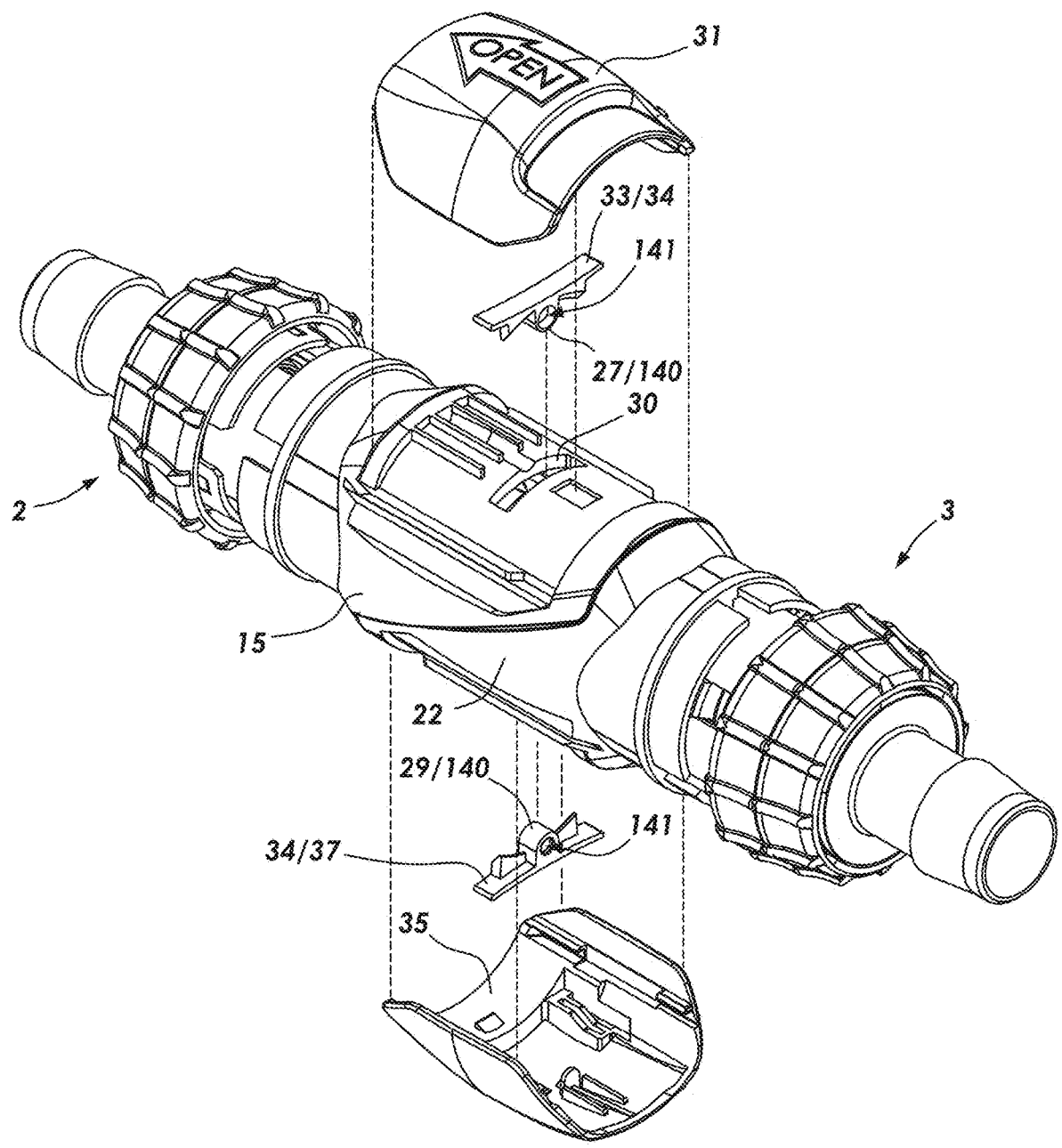

FIG. 14 is an exploded perspective view of a particular embodiment of the connector system showing release elements and their corresponding catches and catch-receiving elements.

III. DETAILED DESCRIPTION OF THE PREFERRED EMBODIMENTS

A connector system (1) for releasably connecting together tubes, such as medical tubing employed in a biomedical environment, is disclosed herein. Advantageously, the connector system (1) can be relatively easily and securely connected, and yet relatively easily intentionally disconnected. Additionally, the connector system (1) can be connected and disconnected repeatedly. Moreover, as to particular embodiments, the connector system (1) can be reusable as opposed to single-use. Also, the connector system (1) can be configured such that the aseptic or sterile environment therein can be preserved, which understandably benefits a repeatably connectable/disconnectable device and/or a reusable device. Furthermore, the connector system (1) can comprise two discrete couplers (2)(3) which connect together to provide the connector system (1), whereby significantly, the couplers (2)(3) can have substantially identical or identical structures; thus, the couplers (2)(3) can be genderless, as opposed to a connector system (1) comprising male and female couplers. In addition, as a result of the substantially identical or identical structures of the couplers (2)(3), the connector system (1) can accommodate bi-directional flow.

The connector system (1) of the present invention includes a first coupler (2) having a first coupler passageway (4) disposed therein and a second coupler (3) having a second coupler passageway (5) disposed therein, whereby, as stated above, the first and second couplers (2)(3) can have substantially identical structures and/or components. Upon releasable axial (or longitudinal) coupling of the first and second couplers (2)(3) (or, stated another way, upon connection of the first and second couplers (2)(3)), the first and second coupler passageways (4)(5) can dispose in fluidic communication to provide a fluid flow path (6) between the first and second couplers (2)(3) and through the connector system (1).

For the purposes of the present invention, an axial or longitudinal direction can be considered parallel to a connector system longitudinal axis (7) and/or a first coupler longitudinal axis (8) and/or a second coupler longitudinal axis (9).

For the purposes of the present invention, two directional references may be used which relate to the junction (10) between the first and second couplers (2)(3) when connected together to provide the connector system (1): an inward direction (11) means toward the junction (10), and an outward direction (12) means away from the junction (10).

Coupler Connected Condition

Now referring primarily to FIGS. 1A through 1C, 7A through 7E, and 11A which illustrate a coupler disconnected condition (13), and FIGS. 2A through 2C, 8A through 8E, and 11B, which illustrate a coupler connected condition (14), the first coupler (2) can include a first coupler housing (15) which houses the first coupler passageway (4). The first coupler housing (15), which can be an annular first coupler housing (15), can have a first coupler housing interior space (16) defined by a first coupler housing internal surface (17) which extends between first coupler housing first and second ends (18)(19), whereby the first coupler passageway (4) can be disposed within the first coupler housing interior space (16). The first coupler housing first end (18) can include a fluid inlet/outlet (20A) in fluidic communication with the first coupler passageway (4), whereby the fluid inlet/outlet (20A) can couple to tubing, such as via a barb (21) coupled to or integrated with the first coupler housing first end (18). Accordingly, the tubing can engage with the barb (21), for example via frictional engagement about the barb (21), to securely couple the tubing to the first coupler housing (15) (and correspondingly to the first coupler (2)) and the first coupler passageway (4) disposed therein.

As the first and second couplers (2)(3) can have substantially identical structures, the second coupler (3) can include a second coupler housing (22) which houses the second coupler passageway (5). The second coupler housing (22), which can be an annular second coupler housing (22), can have a second coupler housing interior space (23) defined by a second coupler housing internal surface (24) which extends between second coupler housing first and second ends (25)(26), whereby the second coupler passageway (5) can be disposed within the second coupler housing interior space (23). The second coupler housing first end (25) can include a fluid outlet/inlet (20B) in fluidic communication with the second coupler passageway (5), whereby the fluid outlet/inlet (20B) can couple to tubing, such as via a barb (21) coupled to or integrated with the second coupler housing first end (25). Accordingly, the tubing can engage with the barb (21), for example via frictional engagement about the barb (21), to securely couple the tubing to the second coupler housing (22) (and correspondingly to the second coupler (3)) and the second coupler passageway (5) disposed therein.

The first coupler housing (15) can be releasably connected to the second coupler housing (22) via axial movement in the inward direction (11) to achieve the coupler connected condition (14) in which the first and second couplers (2)(3) can be connected to one another to provide the connector system (1). Specifically, the first and second coupler housing second ends (19)(26) can be configured to connect to one another to connect the first coupler housing (15) (and correspondingly the first coupler (2)) to the second coupler housing (22) (and correspondingly the second coupler (3)). As to particular embodiments, in contrast to housing ends which may terminate in a plane that is orthogonal to the corresponding coupler's longitudinal axis, the present first and second coupler housing second ends (19)(26) may include at least a portion that terminates in a plane which can be in angled relation to the respective first or second coupler longitudinal axis (8)(9). As but one illustrative and nonlimiting example as shown in the Figures, the angle ($\alpha$) between the plane of the first and second coupler housing second ends (19)(26) and their respective first or second coupler longitudinal axis (8)(9) can be about 25°.

As to particular embodiments, the angle ($\alpha$) between the plane of the first and second coupler housing second ends (19)(26) and their respective first or second coupler longitudinal axis (8)(9) can be less than about 90°. As to particular embodiments, the angle ($\alpha$) between the plane of the first and second coupler housing second ends (19)(26) and their respective first or second coupler longitudinal axis (8)(9) can be less than about 80°. As to particular embodiments, the angle ($\alpha$) between the plane of the first and second coupler housing second ends (19)(26) and their respective first or second coupler longitudinal axis (8)(9) can be less than about 70°. As to particular embodiments, the angle ($\alpha$) between the plane of the first and second coupler housing second ends (19)(26) and their respective first or second coupler longitudinal axis (8)(9) can be less than about 60°. As to particular embodiments, the angle ($\alpha$) between the plane of the first and second coupler housing second ends (19)(26) and their respective first or second coupler longitudinal axis (8)(9) can be less than about 50°. As to particular embodiments, the angle ($\alpha$) between the plane of the first and second coupler housing second ends (19)(26) and their respective first or second coupler longitudinal axis (8)(9) can be less than about 40°. As to particular embodiments, the angle ($\alpha$) between the plane of the first and second coupler housing second ends (19)(26) and their respective first or second coupler longitudinal axis (8)(9) can be less than about 30°.

As to particular embodiments, the angle ($\alpha$) between the plane of the first and second coupler housing second ends (19)(26) and their respective first or second coupler longitudinal axis (8)(9) can be between about 20° and about 80°. As to particular embodiments, the angle ($\alpha$) between the plane of the first and second coupler housing second ends (19)(26) and their respective first or second coupler longitudinal axis (8)(9) can be between about 20° and about 70°. As to particular embodiments, the angle ($\alpha$) between the plane of the first and second coupler housing second ends (19)(26) and their respective first or second coupler longitudinal axis (8)(9) can be between about 20° and about 60°. As to particular embodiments, the angle ($\alpha$) between the plane of the first and second coupler housing second ends (19)(26) and their respective first or second coupler longitudinal axis (8)(9) can be between about 20° and about 50°. As to particular embodiments, the angle ($\alpha$) between the plane of the first and second coupler housing second ends (19)(26) and their respective first or second coupler longitudinal axis (8)(9) can be between about 20° and about 40°. As to particular embodiments, the angle ($\alpha$) between the plane of the first and second coupler housing second ends (19)(26) and their respective first or second coupler longitudinal axis (8)(9) can be between about 20° and about 30°.

Consequently, upon achievement of the coupler connected condition (14), the junction (10) between the first and second coupler housing second ends (19)(26) can be in angled relation to the connector system longitudinal axis (7), which may be a space-saving configuration that may also allow the first and second couplers (2)(3) to nest with one another.

For releasable axial connection of the first and second coupler housings (15)(22), the first coupler (2) can include a first coupler catch (27) movably coupled to the first coupler housing (15); correspondingly, a second coupler catch-receiving element (28) can be coupled to the second coupler housing (22) (such as via coupling to the second coupler elastically deformable valve seat (69)). Upon connection of the first and second coupler housings (15)(22), the first coupler catch (27) can releasably engage with the second coupler catch-receiving element (28) to fix an axial position of the first coupler housing (15) in relation to the second coupler housing (22), thereby achieving the coupler connected condition (14).

For the purposes of the present invention, the term "catch" means a restraint which, upon engagement with a catch-receiving element (28)(30), can function to partially or completely restrain travel of an associated component, such as the first or second coupler housing (15)(22).

For the purposes of the present invention, the term "catch-receiving element" means a restraint which, upon engagement with a catch (27)(29), can function to partially or completely restrain travel of an associated component, such as the first or second coupler housing (15)(22).

As but one illustrative example, the first coupler catch (27) can be configured a protrusion, and the second coupler catch-receiving element (28) can be configured as a recess which can receive the protrusion for locking engagement therewith to fix an axial position of the first coupler housing (15) in relation to the second coupler housing (22), thereby achieving the coupler connected condition (14).

As the first and second couplers (2)(3) can have substantially identical structures, for releasable axial connection of the first and second coupler housings (15)(22), the second coupler (3) can include a second coupler catch (29) movably coupled to the second coupler housing (22); correspondingly, a first coupler catch-receiving element (30) can be coupled to the first coupler housing (15) (such as via coupling to the first coupler elastically deformable valve seat (50)). Upon connection of the first and second coupler housings (15)(22), the second coupler catch (29) can releasably engage with the first coupler catch-receiving element (30) to fix an axial position of the second coupler housing (22) in relation to the first coupler housing (15), thereby achieving the coupler connected condition (14).

As but one illustrative example, the second coupler catch (29) can be configured a protrusion, and the first coupler catch-receiving element (30) can be configured as a recess which can receive the protrusion for locking engagement therewith to fix an axial position of the second coupler housing (22) in relation to the first coupler housing (15), thereby achieving the coupler connected condition (14).

As to particular embodiments, the connector system (1) can be configured to provide a connection indicium upon successful releasable axial coupling of the first and second coupler housings (15)(22) to achieve the coupler connected condition (14), whereby the connection indicium can be a visible indicium, an audible indicium, a tactile indicium, or the like, or combinations thereof. As but one illustrative example, the connection indicium can be an audible click which indicates successful releasable axial coupling of the first and second coupler housings (15)(22) to achieve the coupler connected condition (14). As to particular embodiments, the audible click can be generated by the catch (27)(29) engaging with the catch-receiving element (28)(30). Following, as the connector system (1) comprises two couplers (2)(3) having substantially identical structures, the connector system (1) can include two catches (27)(29) which engage with two respective catch-receiving elements (28)(30), correspondingly generating two audible clicks.

Now referring primarily to FIG. 14, to disconnect the first and second coupler housings (15)(22), the first coupler (2) can include a first coupler release element (31) movably coupled to the first coupler housing (15), whereby travel of the first coupler release element (31), such as axial travel along or over a first coupler housing outer surface (32), can disengage the first coupler catch (27) from the second coupler catch-receiving element (28) to disconnect the first and second coupler housings (15)(22).

As to particular embodiments, the first coupler release element (31) can be configured as a cam and the first coupler catch (27) can function as a follower, whereby the first coupler release element (31) can transform input motion into reciprocating motion of the first coupler catch (27).

For the purposes of the present invention, the term "cam" means a movable element in a mechanical linkage, whereby the cam can have an irregular periphery and may be useful in transforming motion, for example transforming motion in a first direction into motion in a second direction.

For the purposes of the present invention, the term "follower" means a movable element in a mechanical linkage, whereby movement of the follower results from movement of the cam.

The first coupler release element (31) can be biased by a first coupler release element-biasing member (33) which biases the first coupler release element (31) to correspondingly bias the first coupler catch (27) toward releasable engagement with the second coupler catch-receiving element (28) to fix an axial position of the first coupler housing (15) in relation to the second coupler housing (22), thereby achieving the coupler connected condition (14).

Again referring primarily to FIG. 14, as but one illustrative example, the first coupler release element-biasing member (33) can be configured as a resilient member (34), such as a leaf spring, whereby when the resilient member (34) disposes in a non-flexed condition, which can be the default biased condition, the first coupler release element (31) biases the first coupler catch (27) toward releasable engagement with the second coupler catch-receiving element (28) to fix an axial position of the first coupler housing (15) in relation to the second coupler housing (22), thereby achieving the coupler connected condition (14). Upon forcible urging, such as by travel of the first coupler release element (31), the resilient member (34) can be flexed, allowing the first coupler catch (27) to disengage from the second coupler catch-receiving element (28) to disconnect the first and second coupler housings (15)(22).

As to particular embodiments, the first coupler release element (31) can be the same as or similar to the release element disclosed in U.S. Pat. No. 10,173,046 which is hereby incorporated by reference in its entirety herein.

As to particular embodiments, the first coupler release element (31) can be the same as or similar to the catch release disclosed in United States Patent Application Publication No. 2023/0003324 which is hereby incorporated by reference in its entirety herein.

As the first and second couplers (2)(3) can have substantially identical structures, again referring primarily to FIG. 14, to disconnect the first and second coupler housings (15)(22), the second coupler (3) can include a second coupler release element (35) movably coupled to the second coupler housing (22), whereby travel of the second coupler release element (35), such as axial travel along or over a second coupler housing outer surface (36), can disengage the second coupler catch (29) from the first coupler catch-receiving element (30) to disconnect the first and second coupler housings (15)(22).

As to particular embodiments, the second coupler release element (35) can be configured as a cam and the second coupler catch (29) can function as a follower, whereby the second coupler release element (35) can transform input motion into reciprocating motion of the second coupler catch (29).

The second coupler release element (35) can be biased by a second coupler release element-biasing member (37) which biases the second coupler release element (35) to correspondingly bias the second coupler catch (29) toward releasable engagement with the first coupler catch-receiving element (30) to fix an axial position of the second coupler housing (22) in relation to the first coupler housing (15), thereby achieving the coupler connected condition (14).

Again referring primarily to FIG. 14, as but one illustrative example, the second coupler release element-biasing member (37) can be configured as a resilient member (34), such as a leaf spring, whereby when the resilient member (34) disposes in a non-flexed condition, which can be the default biased condition, the second coupler release element (35) biases the second coupler catch (29) toward releasable engagement with the first coupler catch-receiving element (30) to fix an axial position of the second coupler housing (22) in relation to the first coupler housing (15), thereby achieving the coupler connected condition (14). Upon forcible urging, such as by travel of the second coupler release element (35), the resilient member (34) can be flexed, allowing the second coupler catch (29) to disengage from the first coupler catch-receiving element (30) to disconnect the first and second coupler housings (15)(22).

As to particular embodiments, the second coupler release element (35) can be the same as or similar to the release element disclosed in U.S. Pat. No. 10,173,046 which is hereby incorporated by reference in its entirety herein.

As to particular embodiments, the second coupler release element (35) can be the same as or similar to the catch release disclosed in United States Patent Application Publication No. 2023/0003324 which is hereby incorporated by reference in its entirety herein.

Passageway Connected Condition

Now referring primarily to FIGS. 2A through 2C, 8A through 8E, and 11B which illustrate the coupler connected condition (14), and FIGS. 3A through 3C, 9A through 9E, and 11C which illustrate a passageway connected condition (38), the first coupler (2) can include a first coupler conduit (39) disposed within the first coupler housing interior space (16), whereby the first coupler conduit (39) can include an annular first coupler conduit inner surface (40) which defines at least a portion of the first coupler passageway (4) through which fluid can flow. Importantly, the first coupler passageway (4) can be an aseptic or sterile environment, or an environment which is devoid of contaminants, such as microorganisms, bodily fluids, bodily excrements, bodily tissues, etc. The first coupler conduit (39) can extend between first coupler conduit first and second ends (41)(42), whereby the first coupler conduit second end (42) can provide a first coupler conduit engagement end (43) which can sealably engage with an axially adjacent second coupler conduit engagement end (44) to fluidicly connect the first and second coupler passageways (4)(5), thus providing a passageway connected condition (38) and a fluid flow path (6) through the connector system (1).

Now referring primarily to FIGS. 5A, 5B, 12A, and 12B, the first coupler (2) can further include a first coupler elastically deformable valve (45) configured to (i) dispose in a default first coupler elastically deformable valve closed configuration (46) and (ii) be deformable to achieve a first coupler elastically deformable valve open configuration (47). Due to its elasticity, the first coupler elastically deformable valve (45) can return to its default shape after deformation, which can contribute to the repeated usability of the present connector system (1).

The first coupler elastically deformable valve (45) can be disposed within the first coupler housing interior space (16) in axial alignment with the first coupler conduit (39) and in particular, in axial alignment with the first coupler conduit engagement end (43), in spaced apart relation. Specifically, the first coupler elastically deformable valve (45) can be coupled to the first coupler housing (15), such as proximate the first coupler housing second end (19) or to the first coupler housing second end (19), such as via a first coupler elastically deformable valve perimeter (48). As to particular embodiments, the first coupler elastically deformable valve (45) can include a flange (49) proximate its perimeter or the first coupler elastically deformable valve (45) can be bounded by a flanged perimeter, whereby the flange (49) can facilitate the coupling of the first coupler elastically deformable valve (45) to the first coupler housing (15). As to particular embodiments, the first coupler elastically deformable valve (45) can be seated against the first coupler housing (15), such as against the first coupler housing second end (19), by a first coupler elastically deformable valve seat (50). As to particular embodiments, the first coupler elastically deformable valve (45) can be sandwiched between the first coupler housing (15), such as the first coupler housing second end (19), and the first coupler elastically deformable valve seat (50) to fixedly couple the first coupler elastically deformable valve (45) to the first coupler housing (15).

The first coupler elastically deformable valve (45) can include a first coupler elastically deformable valve inner face (51) oriented toward the first coupler housing interior space (16) and the first coupler housing first end (18), and an opposing first coupler elastically deformable valve outer face (52) oriented toward the external environment (53), whereby when in the first coupler elastically deformable valve closed configuration (46), the first coupler elastically deformable valve (45) can function to seal the portion of the first coupler housing interior space (16) in which the first coupler conduit (39) resides from the external environment (53) to preserve the aseptic environment therein, and especially the aseptic environment within the first coupler passageway (4).

Following achievement of the coupler connected condition (14), the first coupler conduit (39) can be axially movable (i) within the first coupler housing interior space (16) and (ii) relative to the first coupler housing (15). In particular, the first coupler conduit (39) can be axially movable between a first coupler conduit retracted position (54) and a first coupler conduit extended position (55). In the first coupler conduit retracted position (54), the first coupler conduit (39) can dispose within the aseptic environment within the first coupler housing interior space (16) bounded by the first coupler elastically deformable valve (45) in the first coupler elastically deformable valve closed configuration (46), and correspondingly isolated from contaminants within the external environment (53).

In more detail, following achievement of the coupler connected condition (14), upon the application of an axial force to the first coupler conduit (39) in an inward direction (11) toward the first coupler elastically deformable valve (45), the first coupler conduit engagement end (43) can engage with and deform (or change the shape of) the first coupler elastically deformable valve (45) and pass therethrough, thus disposing (i) the first coupler elastically deformable valve (45) in the first coupler elastically deformable valve open configuration (47) and (ii) the first coupler conduit (39) in the first coupler conduit extended position (55) in which the first coupler conduit engagement end (43) extends through the first coupler elastically deformable valve (45) and can sealably engage with an axially adjacent second coupler conduit engagement end (44) to fluidicly connect the first and second coupler passageways (4)(5), thus providing the passageway connected condition (38) and a fluid flow path (6) through the connector system (1).

As to particular embodiments, a movable first coupler sleeve (56) can (i) radially surround the first coupler conduit (39), and (ii) axially extend beyond the first coupler conduit engagement end (43) when the first coupler sleeve (56) is biased to dispose in its default first coupler sleeve extended position (57) by a first coupler sleeve biasing member (58), such as a spring, in a non-compressed condition (59), to further preserve the aseptic environment surrounding the first coupler conduit (39), and especially to preserve the aseptic environment within the first coupler passageway (4). Upon the application of an axial force to the first coupler conduit (39) in the inward direction (11), the first coupler housing (15) can engage with and forcibly urge the first coupler sleeve (56) in the outward direction (12) toward a first coupler sleeve retracted position (60), correspondingly compressing the first coupler sleeve biasing member (58). When in the first coupler sleeve retracted position (60), the first coupler sleeve (56) can no longer extend beyond the first coupler conduit engagement end (43), thus allowing the first coupler conduit engagement end (43) to extend beyond the first coupler sleeve (56) and sealably engage with an axially adjacent second coupler conduit engagement end (44) to fluidicly connect the first and second coupler passageways (4)(5), thus providing the passageway connected condition (38) and a fluid flow path (6) through the connector system (1).

As the first and second couplers (2)(3) can have substantially identical structures, again referring primarily to FIGS. 2A through 2C, 8A through 8E, and 11B which illustrate the coupler connected condition (14), and FIGS. 3A through 3C, 9A through 9E, and 11C which illustrate the passageway connected condition (38), the second coupler (3) can include a second coupler conduit (61) disposed within the second coupler housing interior space (23), whereby the second coupler conduit (61) can include an annular second coupler conduit inner surface (62) which defines at least a portion of the second coupler passageway (5) through which fluid can flow. Importantly, the second coupler passageway (5) can be an aseptic or sterile environment, or an environment which is devoid of contaminants, such as microorganisms, bodily fluids, bodily excrements, bodily tissues, etc. The second coupler conduit (61) can extend between second coupler conduit first and second ends (63)(64), whereby the second coupler conduit second end (64) can provide a second coupler conduit engagement end (44) which can sealably engage with an axially adjacent first coupler conduit engagement end (43) to fluidicly connect the first and second coupler passageways (4)(5), thus providing a passageway connected condition (38) and a fluid flow path (6) through the connector system (1).

Now referring primarily to FIGS. 5A, 5B, 12A, and 12B, the second coupler (3) can further include a second coupler elastically deformable valve (65) configured to (i) dispose in a default second coupler elastically deformable valve closed configuration (66) and (ii) be deformable to achieve a second coupler elastically deformable valve open configuration (67). Due to its elasticity, the second coupler elastically deformable valve (65) can return to its default shape after deformation, which can contribute to the repeated usability of the present connector system (1).

The second coupler elastically deformable valve (65) can be disposed within the second coupler housing interior space (23) in axial alignment with the second coupler conduit (61) and in particular, in axial alignment with the second coupler conduit engagement end (44), in spaced apart relation. Specifically, the second coupler elastically deformable valve (65) can be coupled to the second coupler housing (22), such as proximate the second coupler housing second end (26) or to the second coupler housing second end (26), such as via a second coupler elastically deformable valve perimeter (68). As to particular embodiments, the second coupler elastically deformable valve (65) can include a flange (49) proximate its perimeter or the second coupler elastically deformable valve (65) can be bounded by a flanged perimeter, whereby the flange (49) can facilitate the coupling of the second coupler elastically deformable valve (65) to the second coupler housing (22). As to particular embodiments, the second coupler elastically deformable valve (65) can be seated against the second coupler housing (22), such as against the second coupler housing second end (26), by a second coupler elastically deformable valve seat (69). As to particular embodiments, the second coupler elastically deformable valve (65) can be sandwiched between the second coupler housing (22), such as the second coupler housing second end (26), and the second coupler elastically deformable valve seat (69) to fixedly couple the second coupler elastically deformable valve (65) to the second coupler housing (22).

The second coupler elastically deformable valve (65) can include a second coupler elastically deformable valve inner face (70) oriented toward the second coupler housing interior space (23) and the second coupler housing first end (25), and an opposing second coupler elastically deformable valve outer face (71) oriented toward the external environment (53), whereby when in the second coupler elastically deformable valve closed configuration (66), the second coupler elastically deformable valve (65) can function to seal the portion of the second coupler housing interior space (23) in which the second coupler conduit (61) resides from the external environment (53) to preserve the aseptic environment therein, and especially the aseptic environment within the second coupler passageway (5).

Following achievement of the coupler connected condition (14), the second coupler conduit (61) can be axially movable (i) within the second coupler housing interior space (23) and (ii) relative to the second coupler housing (22). In particular, the second coupler conduit (61) can be axially movable between a second coupler conduit retracted position (72) and a second coupler conduit extended position (73). In the second coupler conduit retracted position (72), the second coupler conduit (61) can dispose within the aseptic environment within the second coupler housing interior space (23) bounded by the second coupler elastically deformable valve (65) in the second coupler elastically deformable valve closed configuration (66), and correspondingly isolated from contaminants within the external environment (53).

In more detail, following achievement of the coupler connected condition (14), upon the application of an axial force to the second coupler conduit (61) in an inward direction (11) toward the second coupler elastically deformable valve (65), the second coupler conduit engagement end (44) can engage with and deform (or change the shape of) the second coupler elastically deformable valve (65) and pass therethrough, thus disposing (i) the second coupler elastically deformable valve (65) in the second coupler elastically deformable valve open configuration (67) and (ii) the second coupler conduit (61) in the second coupler conduit extended position (73) in which the second coupler conduit engagement end (44) extends through the second coupler elastically deformable valve (65) and can sealably engage with an axially adjacent first coupler conduit engagement end (43) to fluidicly connect the first and second coupler passageways (4)(5), thus providing the passageway connected condition (38) and a fluid flow path (6) through the connector system (1).

As to particular embodiments, a movable second coupler sleeve (74) can (i) radially surround the second coupler conduit (61), and (ii) axially extend beyond the second coupler conduit engagement end (44) when the second coupler sleeve (74) is biased to dispose in its default second coupler sleeve extended position (75) by a second coupler sleeve biasing member (76), such as a spring, in a non-compressed condition (59), to further preserve the aseptic environment surrounding the second coupler conduit (61), and especially to preserve the aseptic environment within the second coupler passageway (5). Upon the application of an axial force to the second coupler conduit (61) in the inward direction (11), the second coupler housing (22) can engage with and forcibly urge the second coupler sleeve (74) in the outward direction (12) toward a second coupler sleeve retracted position (77), correspondingly compressing the second coupler sleeve biasing member (76). When in the second coupler sleeve retracted position (77), the second coupler sleeve (74) can no longer extend beyond the second coupler conduit engagement end (44), thus allowing the second coupler conduit engagement end (44) to extend beyond the second coupler sleeve (74) and sealably engage with an axially adjacent first coupler conduit engagement end (43) to fluidicly connect the first and second coupler passageways (4)(5), thus providing the passageway connected condition (38) and a fluid flow path (6) through the connector system (1).

As to particular embodiments, each of the first and second coupler conduit engagement ends (43)(44) can include a fluid-tight seal (78), such as an annular seal, which can facilitate the sealable engagement therebetween.

As detailed above, the first and second coupler elastically deformable valves (45)(65) can be configured (i) to seal an environment, such as from contaminants, and (ii) for axial opening via the application of an axial force; therefore, any valve suitable for such a purpose may be useful with the present connector system (1).

As to particular embodiments, the first and second coupler elastically deformable valves (45)(65) can be formed from an elastomeric material, such as silicone, rubber, or the like. As but one illustrative example, the first and second coupler elastically deformable valves (45)(65) can be formed from medical-grade silicone.

As to particular embodiments, the first and second coupler elastically deformable valves (45)(65) can each be a one-piece component which can be self-contained, meaning the sealing function can be an integral part of the one-piece elastomeric component as opposed to a valve which has to engage with a valve seat to form a seal.

As but one illustrative example, the first and second coupler elastically deformable valves (45)(65) can each be configured as a duckbill valve.

As to particular embodiments, the first and second coupler elastically deformable valves (45)(65) can each be configured as a cross-slit valve (79), which may have a larger flow capacity relative to a duckbill valve. As but one illustrative example, a cross-slit valve (79) may have a cylindrical shape with a valve functional region which includes a first slit (80) and a second slit (81) arranged in the form of a cross. Following, the cross-slit valve (79) may have four flaps (such as a four-flapped valve) or four cuspids (such as a quad-cusped valve) which extend from a center point. Of course, a cross-slit valve (79) useful with the present invention need not be limited to two slits and/or four flaps, and can have any number of slits and/or flaps, depending upon the embodiment.

In the elastically deformable valve closed configuration (46)(66), the flaps or cuspids can be adjacent one another to form a fluid-tight seal therebetween. Upon the application of an axial force, the cross-slit valve (79) can deform such that the flaps or cuspids are urged apart, for example by a conduit engagement end (43)(44) which subsequently passes therethrough to dispose the conduit (39)(61) in the conduit extended position (55)(73). As to particular embodiments, the cross-slit valve (79) can be domed-shaped, whereby the cross-slit valve inner face (82) can be concave and the cross-slit valve outer face (83) can be convex.

Once (i) the first coupler elastically deformable valve (45) is disposed in the first coupler elastically deformable valve open configuration (47) as a result of axial movement of the first coupler conduit (39) in the inward direction (11) to dispose the first coupler conduit (39) in the first coupler conduit extended position (55), and (ii) the second coupler elastically deformable valve (65) is disposed in the second coupler elastically deformable valve open configuration (67) as a result of axial movement of the second coupler conduit (61) in the inward direction (11) to dispose the second coupler conduit (61) in the second coupler conduit extended position (73), the first coupler conduit engagement end (43) can sealably engage with the axially adjacent second coupler conduit engagement end (44) to fluidicly connect the first and second coupler passageways (4)(5), thus providing the passageway connected condition (38) and a fluid flow path (6) through the connector system (1), the axial position of the first coupler conduit (39) (and correspondingly the first coupler passageway (4)) and the second coupler conduit (61) (and correspondingly the second coupler passageway (5)) can be fixed, thereby locking the first and second coupler passageways (4)(5) together.

For this purpose, the first coupler (2) can include a first coupler first lock assembly (84) which can lock the first coupler conduit (39) in the first coupler conduit extended position (55) and accordingly, can lock the first coupler conduit engagement end (43) in axially adjacent relation to the second coupler conduit engagement end (44). As to particular embodiments, the first coupler first lock assembly (84) can include a rotatable first coupler first locking ring (85) having a catch-receiving element, such as a slot, that can receive a corresponding catch, such as a tooth, coupled to the first coupler housing (15). Upon simultaneous axial movement of the first coupler conduit (39) and the first coupler first locking ring (85) relative to the first coupler housing (15) in the inward direction (11) to achieve the passageway connected condition (38), the tooth can be received within the slot. Following, the first coupler first locking ring (85) can be rotated in a first direction to rotate the slot relative to the tooth, whereby upon rotation, the tooth can engage with a stop proximate the slot. This engagement can preclude the first coupler conduit (39) and the first coupler first locking ring (85) from axial movement relative to the first coupler housing (15) in the outward direction (12), thus precluding the first coupler conduit (39) from returning to the first coupler conduit retracted position (54). For unlocking, the first coupler first locking ring (85) can be rotated in a second direction which can be opposite the first direction to rotate the slot relative to the tooth to disengage the tooth from the stop proximate the slot.

As the first and second couplers (2)(3) can have substantially identical structures, the second coupler (3) can include a second coupler first lock assembly (89) which can lock the second coupler conduit (61) in the second coupler conduit extended position (73) and accordingly, can lock the second coupler conduit engagement end (44) in axially adjacent relation to the first coupler conduit engagement end (43). As to particular embodiments, the second coupler first lock assembly (89) can include a rotatable second coupler first locking ring (90) having a catch-receiving element, such as a slot, that can receive a corresponding catch, such as a tooth, coupled to the second coupler housing (22). Upon simultaneous axial movement of the second coupler conduit (61) and the second coupler first locking ring (90) relative to the second coupler housing (22) in the inward direction (11) to achieve the passageway connected condition (38), the tooth can be received within the slot. Following, the second coupler first locking ring (90) can be rotated in a first direction to rotate the slot relative to the tooth, whereby upon rotation, the tooth can engage with a stop proximate the slot. This engagement can preclude the second coupler conduit (61) and the second coupler first locking ring (90) from axial movement relative to the second coupler housing (22) in the outward direction (12), thus precluding the second coupler conduit (61) from returning to the second coupler conduit retracted position (72). For unlocking, the second coupler first locking ring (90) can be rotated in a second direction which can be opposite the first direction to rotate the slot relative to the tooth to disengage the tooth from the stop proximate the slot.

Open Fluid Flow Path Condition

When in the passageway connected condition (38) in which the first coupler conduit engagement end (43) sealably engages with an axially adjacent second coupler conduit engagement end (44) to fluidicly connect the first and second coupler passageways (4)(5), fluid may be intentionally precluded from flowing through the first and second coupler passageways (4)(5), and thus through the connector system (1) via the fluid flow path (6), consequently resulting in a closed fluid flow path condition (91) (as shown in FIGS. 1A through 3C, 7A through 9E, 11A, 11B, and 11C).

Now referring primarily to FIGS. 3A through 3C, 9A through 9E, and 11C which illustrate the passageway connected condition (38) and the closed fluid flow path condition (91), and FIGS. 4A through 4E, 5D, 10A through 10E, and 11D which illustrate an open fluid flow path condition (92), the first coupler (2) can include a movable (such as axially movable) first coupler valve (93) operable to interrupt fluid flow through the first coupler conduit (39) and correspondingly, through the first coupler passageway (4). As to particular embodiments, the first coupler valve (93) can be movable within a first coupler valve seat (94) to sealably occlude a first coupler port (95) in fluidic communication with the first coupler passageway (4), thereby providing a first coupler passageway closed condition (96) in which fluid flow through the first coupler port (95) and accordingly, through the first coupler passageway (4), can be interrupted.

The first coupler valve (93) can be biased by a first coupler valve-biasing member (97) which biases the first coupler valve (93) toward a default first coupler valve closed position (98) in which the first coupler port (95) can be sealably occluded by engagement with a sealing surface (99) to provide the first coupler passageway closed condition (96).

As an illustrative example, the first coupler valve (93) can include an annular first coupler valve inner surface (100) which defines at least a portion of the first coupler passageway (4) through which fluid can flow; with this configuration, the first coupler conduit (39) and the first coupler valve (93) can together provide the first coupler passageway (4).

Additionally, the first coupler valve (93) can include the first coupler port (95) in fluidic communication with the first coupler passageway (4). As to particular embodiments, the first coupler port (95) can be radially disposed within the first coupler valve (93) to communicate between first coupler valve inner and outer surfaces (100)(101). As to particular embodiments, the first coupler port (95) can be configured as a plurality of first coupler ports (95) radially disposed within the first coupler valve (93) in circumferentially spaced-apart relation. As to particular embodiments, the first coupler port(s) (95) can be disposed proximate a first coupler valve second end (102).

The first coupler valve seat (94) can telescopingly dispose about the first coupler valve (93) which can longitudinally travel within the first coupler valve seat (94), such as via sliding. As to particular embodiments, the first coupler valve (93) and the first coupler valve seat (94) can be coaxial or disposed in concentric relation.

With this configuration, a first coupler valve seat inner surface (103) can provide the sealing surface (99) which can dispose adjacent the first coupler valve outer surface (101) and sealably engage with the first coupler port (95), such as by overlaying the first coupler port (95), to provide the first coupler valve closed position (98) and the first coupler passageway closed condition (96) in which fluid flow through the first coupler port (95) and accordingly, through the first coupler passageway (4), is interrupted. A fluid-tight seal can exist between the first coupler valve seat inner surface (103) and the first coupler valve outer surface (101) proximate the first coupler port (95). As to particular embodiments, one or more o-rings (104) can be coupled to the first coupler valve outer surface (101), whereby when overlaid by the first coupler valve seat inner surface (103), the o-ring(s) (104) can function to provide the fluid-tight seal between the first coupler valve seat inner surface (103) and the first coupler valve outer surface (101) proximate the first coupler port (95).

As stated above, the first coupler valve (93) can be biased by a first coupler valve-biasing member (97) which biases the first coupler valve (93) toward the default first coupler valve closed position (98) to provide the first coupler passageway closed condition (96). As but one illustrative example, the first coupler valve-biasing member (97) can be configured as a resiliently compressible member (105), such as a spring (106) (for example, a coil spring or a helical spring); however, the first coupler valve-biasing member (97) need not be limited to this particular configuration.

As to particular embodiments having the first coupler valve-biasing member (97) configured as a coil spring or a helical spring (106), the spring (106) can be disposed about a portion of the first coupler valve (93) (or about a portion of the first coupler valve outer surface (101)) to entirely surround that portion of the first coupler valve (93) such that the spring (106) and the first coupler valve (93) can be coaxial or disposed in concentric relation.

In contrast to conventional "quick release" couplers, as the present first coupler valve-biasing member (97) is disposed about the first coupler valve (93), the present first coupler valve-biasing member (97) is correspondingly disposed external to or outside of the first coupler passageway (4) and accordingly, external to or outside of the fluid flow path (6) when the passageway connected condition (38) is achieved. As a result, fluid flowing through the connector system (1) via the fluid flow path (6) does not contact the valve-biasing member (97), which may be advantageous for a plurality of reasons, including elimination of potential substrate for biofilm growth within the fluid flow path (6) and/or elimination of a physical impediment to fluid flow within the fluid flow path (6).

The spring (106) can bare against opposing spring bearing surfaces (107)(108); for example, a spring first end (109) can bear against a spring first bearing surface (107) outwardly extending from the first coupler valve outer surface (101), and an opposing spring second end (110) can bear against a spring second bearing surface (108) provided by, for example, a support member (111) axially aligned with the first coupler valve (93) proximate the first coupler valve first end (112).

When in a non-compressed condition (59), which can be the default biased condition, the spring (106) can bias the first coupler valve (93) toward the first coupler valve closed position (98) in which the first coupler port (95) can be sealably occluded by the sealing surface (99) of the first coupler valve seat (94) to provide the first coupler passageway closed condition (96).

The first coupler valve (93) can be urged by a first coupler first driver (113) which can be movably coupled to the first coupler housing (15), whereby the first coupler first driver (113) can engage with and apply an axial force to the first coupler valve (93) in the outward direction (12) to correspondingly drive the first coupler valve (93) to travel in the outward direction (12) and compress the first coupler valve-biasing member (97). Following, the first coupler valve (93) can axially travel within the first coupler valve seat (94) away from the first coupler port (95) toward a first coupler valve open position (114) in which the first coupler port (95) can be disengaged from the sealing surface (99) of the first coupler valve seat (94), thus providing a first coupler passageway open condition (115) which permits fluid to flow through the first coupler port (95) and accordingly, through the first coupler passageway (4). As the first coupler valve (93) can include the spring first bearing surface (107), movement of the first coupler valve (93) in the outward direction (12) correspondingly compresses the first coupler valve-biasing member (97) toward its compressed condition.

As to particular embodiments, the first coupler first driver (113) can be a component of the first coupler (2). As to particular embodiments, to ensure that the first coupler valve (93) disposes in the default first coupler valve closed position (98) and correspondingly, the first coupler passageway (4) disposes in the default first coupler passageway closed condition (96) when the first and second couplers (2)(3) are disconnected, movement of the first coupler first driver (113) can be actuated by a second coupler second driver (116)

which can be a component of the second coupler (3) and movably coupled to the second coupler housing (22). Following, the first coupler first driver (113) can only be actuated when the first and second couplers (2)(3) are connected.

As to particular embodiments, the second coupler second driver (116) can be actuated by a second coupler second driver actuator (117) which can be a component of the second coupler (3). The second coupler second driver actuator (117) can forcibly urge the second coupler second driver (116) to travel in the inward direction (11). The second coupler second driver (116) can engage with and apply an axial force to the first coupler first driver (113) in the outward direction (12); correspondingly, the first coupler first driver (113) can forcibly urge the first coupler valve (93) to axially travel within the first coupler valve seat (94) away from the first coupler port (95) toward the first coupler valve open position (114) which disposes the first coupler passageway (4) in the first coupler passageway open condition (115), allowing the fluid flow path (6) to have an open fluid flow path condition (92) which permits fluid to flow through the connector system (1).

As to particular embodiments, the first coupler first driver (113) can include at least one arm (118) which can be driven in the outward direction (12) by actuation of the second coupler second driver (116) to engage with and drive the first coupler valve (93) to travel in the outward direction (12) to dispose the first coupler passageway (4) in the first coupler passageway open condition (115). As to particular embodiments, the first coupler first driver (113) can include a plurality of arms (118) disposed in circumferentially spaced-apart relation, whereby the arms (118) can be connected together by an annular element (119).

As to particular embodiments, the second coupler second driver (116) can include at least one arm (118) which can be driven in the inward direction (11) by actuation of the second coupler second driver actuator (117) to engage with and drive the first coupler first driver (113) to travel in the outward direction (12) to dispose the first coupler passageway (4) in the first coupler passageway open condition (115). As to particular embodiments, the second coupler second driver (116) can include a plurality of arms (118) disposed in circumferentially spaced-apart relation, whereby the arms (118) can be connected together by an annular element (119).

As the first and second couplers (2)(3) can have substantially identical structures, again referring primarily to FIGS. 3A through 3C, 9A through 9E, and 11C which illustrate the passageway connected condition (38) and the closed fluid flow path condition (91), and FIGS. 4A through 4C, 10A through 10E, and 11D which illustrate an open fluid flow path condition (92), the second coupler (3) can include a movable (such as axially movable) second coupler valve (120) operable to interrupt fluid flow through the second coupler conduit (61) and correspondingly, through the second coupler passageway (5). As to particular embodiments, the second coupler valve (120) can be movable within a second coupler valve seat (121) to sealably occlude a second coupler port (122) in fluidic communication with the second coupler passageway (5), thereby providing a second coupler passageway closed condition (123) in which fluid flow through the second coupler port (122) and accordingly, through the second coupler passageway (5), can be interrupted.

The second coupler valve (120) can be biased by a second coupler valve-biasing member (124) which biases the second coupler valve (120) toward a default second coupler valve closed position (125) in which the second coupler port (122) can be sealably occluded by engagement with a sealing surface (99) to provide the second coupler passageway closed condition (123).

As a first illustrative example, the second coupler valve (120) can include an annular second coupler valve inner surface (126) which defines at least a portion of the second coupler passageway (5) through which fluid can flow; with this configuration, the second coupler conduit (61) and the second coupler valve (120) can together provide the second coupler passageway (5).

Additionally, the second coupler valve (120) can include the second coupler port (122) in fluidic communication with the second coupler passageway (5). As to particular embodiments, the second coupler port (122) can be radially disposed within the second coupler valve (120) to communicate between second coupler valve inner and outer surfaces (127)(127). As to particular embodiments, the second coupler port (122) can be configured as a plurality of second coupler ports (122) radially disposed within the second coupler valve (120) in circumferentially spaced-apart relation. As to particular embodiments, the second coupler port(s) (122) can be disposed proximate a second coupler valve second end (128).

The second coupler valve seat (121) can telescopingly dispose about the second coupler valve (120) which can longitudinally travel within the second coupler valve seat (121), such as via sliding. As to particular embodiments, the second coupler valve (120) and the second coupler valve seat (121) can be coaxial or disposed in concentric relation.

With this configuration, a second coupler valve seat inner surface (129) can provide the sealing surface (99) which can dispose adjacent the second coupler valve outer surface (127) and sealably engage with the second coupler port (122), such as by overlaying the second coupler port (122), to provide the second coupler valve closed position (125) and the second coupler passageway closed condition (123) in which fluid flow through the second coupler port (122) and accordingly, through the second coupler passageway (5), is interrupted. A fluid-tight seal can exist between the second coupler valve seat inner surface (129) and the second coupler valve outer surface (127) proximate the second coupler port (122). As to particular embodiments, one or more o-rings (104) can be coupled to the second coupler valve outer surface (127), whereby when overlaid by the second coupler valve seat inner surface (129), the o-ring(s) (104) can function to provide the fluid-tight seal between the second coupler valve seat inner surface (129) and the second coupler valve outer surface (127) proximate the second coupler port (122).

As stated above, the second coupler valve (120) can be biased by a second coupler valve-biasing member (124) which biases the second coupler valve (120) toward the default second coupler valve closed position (125) to provide the second coupler passageway closed condition (123). As but one illustrative example, the second coupler valve-biasing member (124) can be configured as a resiliently compressible member (105), such as a spring (for example, a coil spring or a helical spring); however, the second coupler valve-biasing member (124) need not be limited to this particular configuration.

As to particular embodiments having the second coupler valve-biasing member (124) configured as a coil spring or a helical spring (106), the spring (106) can be disposed about a portion of the second coupler valve (120) (or about a portion of the second coupler valve outer surface (127)) to entirely surround that portion of the second coupler valve (120) such that the spring (106) and the second coupler valve (120) can be coaxial or disposed in concentric relation.

In contrast to conventional "quick release" couplers, as the present second coupler valve-biasing member (124) is disposed about the second coupler valve (120), the present second coupler valve-biasing member (124) is correspondingly disposed external to or outside of the second coupler passageway (5) and accordingly, external to or outside of the fluid flow path (6) when the passageway connected condition (38) is achieved. As a result, fluid flowing through the connector system (1) via the fluid flow path (6) does not contact the valve-biasing member (124), which may be advantageous for a plurality of reasons, including elimination of potential substrate for biofilm growth within the fluid flow path (6) and/or elimination of a physical impediment to fluid flow within the fluid flow path (6).

The spring (106) can bare against opposing spring bearing surfaces (107)(108); for example, a spring first end (109) can bear against a spring first bearing surface (107) outwardly extending from the second coupler valve outer surface (127), and an opposing spring second end (110) can bear against a spring second bearing surface (108) provided by, for example, a support member (111) axially aligned with the second coupler valve (120) proximate the second coupler valve first end (130).

When in a non-compressed condition (59), which can be the default biased condition, the spring (106) can bias the second coupler valve (120) toward the second coupler valve closed position (125) in which the second coupler port (122) can be sealably occluded by the sealing surface (99) of the second coupler valve seat (121) to provide the second coupler passageway closed condition (123).

The second coupler valve (120) can be urged by a second coupler first driver (131) which can be movably coupled to the second coupler housing (22), whereby the second coupler first driver (131) can engage with and apply an axial force to the second coupler valve (120) in the outward direction (12) to correspondingly drive the second coupler valve (120) to travel in the outward direction (12) and compress the second coupler valve-biasing member (124). Following, the second coupler valve (120) can axially travel within the second coupler valve seat (121) away from the second coupler port (122) toward a second coupler valve open position (132) in which the second coupler port (122) can be disengaged from the sealing surface (99) of the second coupler valve seat (121), thus providing a second coupler passageway open condition (133) which permits fluid to flow through the second coupler port (122) and accordingly, through the second coupler passageway (5). As the second coupler valve (120) can include the spring first bearing surface (107), movement of the second coupler valve (120) in the outward direction (12) correspondingly compresses the second coupler valve-biasing member (124) toward its compressed condition.

As to particular embodiments, the second coupler first driver (131) can be a component of the second coupler (3). As to particular embodiments, to ensure that the second coupler valve (120) disposes in the default second coupler valve closed position (125) and correspondingly, the second coupler passageway (5) disposes in the default second coupler passageway closed condition (123) when the first and second couplers (2)(3) are disconnected, movement of the second coupler first driver (131) can be actuated by a first coupler second driver (134) which can be a component of the first coupler (2) and movably coupled to the first coupler housing (15). Following, the second coupler first driver (131) can only be actuated when the first and second couplers (2)(3) are connected.

As to particular embodiments, the first coupler second driver (134) can be actuated by a first coupler second driver actuator (135) which can be a component of the first coupler (2). The first coupler second driver actuator (135) can forcibly urge the first coupler second driver (134) to travel in the inward direction (11). The first coupler second driver (134) can engage with and apply an axial force to the second coupler first driver (131) in the outward direction (12); correspondingly, the second coupler first driver (131) can forcibly urge the second coupler valve (120) to axially travel within the second coupler valve seat (121) away from the second coupler port (122) toward the second coupler valve open position (132) which disposes the second coupler passageway (5) in the second coupler passageway open condition (133), allowing the fluid flow path (6) to have an open fluid flow path condition (92) which permits fluid to flow through the connector system (1).

As to particular embodiments, the second coupler first driver (131) can include at least one arm (118) which can be driven in the outward direction (12) by actuation of the first coupler second driver (134) to engage with and drive the second coupler valve (120) to travel in the outward direction (12) to dispose the second coupler passageway (5) in the second coupler passageway open condition (133). As to particular embodiments, the second coupler first driver (131) can include a plurality of arms (118) disposed in circumferentially spaced-apart relation, whereby the arms (118) can be connected together by an annular element (119).

As to particular embodiments, the first coupler second driver (134) can include at least one arm (118) which can be driven in the inward direction (11) by actuation of the first coupler second driver actuator (135) to engage with and drive the second coupler first driver (131) to travel in the outward direction (12) to dispose the second coupler passageway (5) in the second coupler passageway open condition (133). As to particular embodiments, the second coupler second driver (116) can include a plurality of arms (118) disposed in circumferentially spaced-apart relation, whereby the arms (118) can be connected together by an annular element (119).

Once in the open fluid flow path condition (92), the first coupler valve open position (114) (and correspondingly the first coupler passageway open condition (115)) and the second coupler valve open position (132) (and correspondingly the second coupler passageway open condition (133)) can be fixed, thereby locking the open fluid flow path condition (92).

For this purpose, the first coupler (2) can include a first coupler second lock assembly (136) which can lock the first coupler valve (93) in the first coupler valve open position (114), whereby the first coupler second lock assembly (136) can be structurally the same as or similar to the first coupler first lock assembly (84) detailed above, thus including a rotatable first coupler second locking ring (137).

As the first and second couplers (2)(3) can have substantially identical structures, the second coupler (3) can include a second coupler second lock assembly (138) which can lock the second coupler valve (120) in the second coupler valve open position (132), whereby the second coupler second lock assembly (138) can be structurally the same as or similar to the second coupler first lock assembly (89) detailed above, thus including a rotatable second coupler second locking ring (139).

As to particular embodiments, the first and second coupler second locking rings (137)(139) can provide the respective first and second coupler second driver actuators (135)(117) or, said another way, the first and second coupler second driver actuators (135)(117) can provide the respective first and second coupler second locking rings (137)(139), meaning that one component can provide both functions.

As to particular embodiments, the first coupler (2) may include an additional locking mechanism to maintain the coupler connected condition (14) during the open fluid flow path condition (92); for example, an arm (118) of the first coupler first driver (113) can lockingly engage with the first coupler catch (27) when received within the first coupler catch-receiving element (30) to fix the axial position of the first coupler housing (15) in relation to the second coupler housing (22). As but one illustrative example, the first coupler catch (27) can be configured as an annular protrusion (140) having an axial opening (141) therethrough, whereby the arm (118) can axially pass through the opening (141) to lock the annular protrusion (140) within the first coupler catch-receiving element (30).

As the first and second couplers (2)(3) can have substantially identical structures, as to particular embodiments, the second coupler (3) may include an additional locking mechanism to maintain the coupler connected condition (14) during the open fluid flow path condition (92); for example, an arm (118) of the second coupler first driver (131) can lockingly engage with the second coupler catch (29) when received within the second coupler catch-receiving element (28) to fix the axial position of the second coupler housing (22) in relation to the first coupler housing (15). As but one illustrative example, the second coupler catch (29) can be configured as an annular protrusion (140) having an axial opening (141) therethrough, whereby the arm (118) can axially pass through the opening (141) to lock the annular protrusion (140) within the second coupler catch-receiving element (28).

A method of making a particular embodiment of a connector system (1) for releasably connecting tubes can include providing and assembling the component parts detailed above and in the claims.

Components of the connector system (1) can be formed from one or more of any of a numerous and wide variety of materials capable of providing a functional connector system (1). By way of non-limiting example, the material can include or consist of: rubber, rubber-like material, plastic, plastic-like material, acrylic, polyamide, polyester, polypropylene, polyethylene, polyvinyl chloride-based materials, silicone-based materials, or the like, or combinations thereof. Additional non-limiting examples can include polymeric materials or resins, for example thermoplastics, such as acrylic, nylon, polybenzimidazole, polyethylene, polypropylene, polystyrene, polyvinyl chloride, polytetrafluoroethylene, polysulfone, or the like, or combinations thereof; thermosets, such as polyester fiberglass, polyurethanes, rubber, polyoxybenzylmethylenglycolanhydride, urea-formaldehyde foam, melamine resin, epoxy resin, polyimides, cynate esters, polycyanurates, polyester resin, or the like, or combinations thereof; elastomers, such as natural polyisoprene, synthetic polyisoprene, polybutadiene, chloropene rubber, butyl rubber, styrene-butadiene rubber, nitrile rubber, ethylene propylene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, thermal plastic elastomer (TPE), or the like, or combinations thereof.

As to particular embodiments, one or more components of the connector system (1) can be formed from an antibacterial material.

As to particular embodiments, one or more components of the connector system (1) can be formed entirely from a non-metallic material.

Additionally, components of the connector system (1) can be produced from any of a wide variety of processes depending upon the application, such as press molding, injection molding, fabrication, machining, printing, additive printing, or the like, or combinations thereof, as one piece or assembled from a plurality of pieces into a component of the connector system (1).

As to particular embodiments, one or more components of the connector system (1) can be disposable or repeatedly usable or reusable, depending upon the application.

A method of using a particular embodiment of the present connector system (1) for releasably connecting tubes can include obtaining the first and second couplers (2)(3), as detailed above, and releasably connecting the first and second couplers (2)(3), such as by forcible urging in the axially inward direction (11), to achieve the coupler connected condition (14). The method can further include forcibly urging the first coupler conduit (39) in the axially inward direction (11) through the first coupler elastically deformable valve (45), and forcibly urging the second coupler conduit (61) in the axially inward direction (11) through the second coupler elastically deformable valve (45) to allow the first and second coupler conduit engagement ends (43)(44) to sealably engage. The method can further include forcibly urging the first coupler valve (93) in the axially outward direction (12) toward the first coupler valve open position (114) which provides the first coupler passageway open condition (115) that permits fluid to flow through the first coupler passageway (4), and forcibly urging the second coupler valve (120) in the axially outward direction (12) toward the second coupler valve open position (132) which provides the second coupler passageway open condition (133) that permits fluid to flow through the second coupler passageway (5); the first and second coupler passageway open conditions (115)(133) provide the open fluid flow path condition (92) which permits fluid to flow through the connector system (1).

The method can further include disconnecting the first and second couplers (2)(3).

The method can further include repeatedly connecting and disconnecting the first and second couplers (2)(3).

The method can further include repeatedly using or reusing the first and second couplers (2)(3).

As to particular embodiments, a method of using a particular embodiment of the present connector system (1) for releasably connecting tubes can include a minimal number of steps, which may be in contrast to other connectable/disconnectable devices. As a first example, there can be less than five steps for connection of the connector system (1). As a second example, there can be no more than four steps for connection of the connector system (1). As a third example, there can be four steps for connection of the connector system (1), as follows: (a) forcibly urging one or both of the first and second couplers (2)(3) in the axially inward direction (11) to achieve the coupler connected condition (14) while substantially simultaneously forcibly urging the first and second coupler conduits (39)(61) in the axially inward direction (11) through the corresponding first and second coupler elastically deformable valves (45)(65) to sealably engage the first and second coupler conduit engagement ends (43)(44) and fluidicly connect the first and second coupler passageways (4)(5) to provide the passageway connected condition (38); (b) locking the first and second coupler passageways (4)(5) together via a first lock assembly (84)(89); (c) forcibly urging the first and second coupler valves (93)(120) in the axially outward direction (12) toward first and second coupler valve open positions (114)(132) to provide the first and second coupler passageway open conditions (115)(133) to provide an open fluid flow path condition (92) which permits fluid to flow through the connector system (1); and (d) locking the open fluid flow path condition (92) via the second lock assembly (136)(138). As to particular embodiments, there can be only four steps for connection of the connector system (1).

Correspondingly, the present connector system (1) can be disconnected (i) in less than five steps, (ii) in no more than four steps, (iii) in four steps, or (iv) in only four steps, such as by reversing the above connection steps.

As can be easily understood from the foregoing, the basic concepts of the present invention may be embodied in a variety of ways. The invention involves numerous and varied embodiments of a connector system and methods for making and using such a connector system, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "connector" should be understood to encompass disclosure of the act of "connecting"—whether explicitly discussed or not—and, conversely, were there effectively disclosure of the act of "connecting", such a disclosure should be understood to encompass disclosure of a "connector" and even a "means for connecting". Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Further, for the purposes of the present invention, the term "coupled" or derivatives thereof can mean indirectly coupled, coupled, directly coupled, connected, directly connected, or integrated with, depending upon the embodiment.

Thus, the applicant(s) should be understood to claim at least: i) each of the connector systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application, if any, provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A connector system for releasably connecting tubes, said connector system comprising:
   a first coupler comprising:
      a first coupler conduit comprising a first coupler passageway;
      a first coupler elastically deformable valve in axial alignment with said first coupler conduit, said first coupler elastically deformable valve deformable between a default first coupler elastically deformable valve closed configuration and a first coupler elastically deformable valve open configuration;
      wherein in said default first coupler elastically deformable valve closed configuration, said first coupler elastically deformable valve seals said first coupler passageway from an external environment;
      wherein said first coupler elastically deformable valve is deformable by a first coupler conduit engagement end configured to pass through said first coupler elastically deformable valve to dispose said first coupler elastically deformable valve in said first coupler elastically deformable valve open configuration; and
   a second coupler identical to said first coupler;
      wherein a second coupler elastically deformable valve of said second coupler is deformable by an engagement end of a second coupler conduit of said second coupler configured to pass through said second coupler elastically deformable valve to dispose said second coupler elastically deformable valve in a second coupler elastically deformable valve open configuration; and
   wherein said first coupler conduit engagement end extending through said first coupler elastically deformable valve sealably engages with an axially adjacent said engagement end of said second coupler conduit extending through said second coupler elastically deformable valve to fluidically connect said first coupler passageway with a second coupler passageway to provide a passageway connected condition.

2. The connector system of claim 1, wherein an aseptic or sterile environment within said first coupler passageway and said second coupler passageway is preserved.

3. The connector system of claim 1, further comprising:
   a first coupler housing having a first coupler housing interior space in which said first coupler conduit is disposed; and
   a second coupler housing having a second coupler housing interior space in which said second coupler conduit is disposed.

4. The connector system of claim 3, wherein:
   said first coupler housing comprises a first coupler housing first end opposite a first coupler housing second end; and
   said second coupler housing comprises a second coupler housing first end opposite a second coupler housing second end.

5. The connector system of claim 4, wherein:
   said first coupler housing second end comprises at least a portion that terminates in a plane which is in angled relation to a first coupler longitudinal axis; and
   said second coupler housing second end comprises at least a portion that terminates in a plane which is in angled relation to a second coupler longitudinal axis.

6. The connector system of claim 1, wherein:
   said first coupler conduit is axially movable between a default first coupler conduit retracted position and a first coupler conduit extended position;
   wherein in said default first coupler conduit retracted position, said first coupler conduit disposes within an aseptic environment within a first coupler housing interior space bounded by said first coupler elastically deformable valve in said default first coupler elastically deformable valve closed configuration;
   wherein in said default first coupler conduit retracted position, said first coupler conduit is correspondingly isolated from contaminants within the external environment;
   said second coupler conduit is axially movable between a default second coupler conduit retracted position and a second coupler conduit extended position;
   wherein in said default second coupler conduit retracted position, said second coupler conduit disposes within an aseptic environment within a second coupler housing interior space bounded by said second coupler elastically deformable valve in a second coupler elastically deformable valve closed configuration; and
   wherein in said default second coupler conduit retracted position, said second coupler conduit is correspondingly isolated from said contaminants within the external environment.

7. The connector system of claim 1, further comprising:
   a movable first coupler sleeve radially surrounding said first coupler conduit and axially extending beyond said first coupler conduit engagement end when said movable first coupler sleeve is biased to dispose in a default first coupler sleeve extended position; and
   a movable second coupler sleeve radially surrounding said second coupler conduit and axially extending beyond said engagement end of said second coupler conduit when said second coupler sleeve is biased to dispose in a default second coupler sleeve extended position.

8. The connector system of claim 7, wherein:
   in a first coupler sleeve retracted position, said first coupler conduit engagement end axially extends beyond said movable first coupler sleeve; and
   in a second coupler sleeve retracted position, said engagement end of said second coupler conduit axially extends beyond said movable second coupler sleeve.

9. The connector system of claim 1, wherein each of said first coupler elastically deformable valve and said second coupler elastically deformable valve is configured for axial opening via an application of an axial force.

10. The connector system of claim 1, wherein each of said first coupler elastically deformable valve and said second coupler elastically deformable valve is a self-contained, one-piece component.

11. The connector system of claim 1, wherein each of said first coupler elastically deformable valve and said second coupler elastically deformable valve is configured as a duckbill valve.

12. The connector system of claim 1, wherein each of said first coupler elastically deformable valve and said second coupler elastically deformable valve is configured as a cross-slit valve.

13. The connector system of claim 1, further comprising:
a first coupler first lock assembly configured to lock said first coupler conduit engagement end and said engagement end of said second coupler conduit which are sealably engaged and which fluidically connect said first coupler passageway and said second coupler passageway to provide said passageway connected condition; and
a second coupler first lock assembly configured to lock said engagement end of said second coupler conduit and said first coupler conduit engagement end which are sealably engaged and which fluidically connect said second coupler passageway and said first coupler passageway to provide said passageway connected condition.

14. The connector system of claim 13, wherein:
said first coupler first lock assembly comprises a rotatable first coupler first locking ring configured to lock upon rotation in a first direction and unlock upon rotation in a second direction; and
said second coupler first lock assembly comprises a rotatable second coupler first locking ring configured to lock upon said rotation in said first direction and unlock upon said rotation in said second direction.

15. The connector system of claim 1, further comprising:
a first coupler valve operable to interrupt a flow of a fluid through said first coupler passageway when in a default first coupler valve closed position;
a second coupler valve operable to interrupt a flow of a fluid through said second coupler passageway when in a default second coupler valve closed position;
wherein said default first coupler valve closed position and said default second coupler valve closed position provide a closed fluid flow path condition;
a first coupler valve-biasing member which biases said first coupler valve toward said default first coupler valve closed position; and
a second coupler valve-biasing member which biases said second coupler valve toward said default second coupler valve closed position;
wherein each of said first coupler valve-biasing member and said second coupler valve-biasing member is disposed external to or outside of a flow path of said fluid when said passageway connected condition is achieved; and
wherein said fluid flowing through said flow path of said fluid does not contact said first coupler valve-biasing member and said second coupler valve-biasing member.

16. The connector system of claim 15, further comprising:
a first coupler driver operable to forcibly urge said first coupler valve toward a first coupler valve open position which provides a first coupler passageway open condition that permits said flow of said fluid through said first coupler passageway; and
a second coupler driver operable to forcibly urge said second coupler valve toward a second coupler valve open position which provides a second coupler passageway open condition that permits said flow of said fluid through said second coupler passageway;
wherein said first coupler passageway open condition and said second coupler passageway open condition provide an open fluid flow path condition which permits said fluid to flow through said connector system.

17. The connector system of claim 16, further comprising:
a first coupler second lock assembly configured to lock said first coupler valve in said first coupler valve open position; and
a second coupler second lock assembly configured to lock said second coupler valve in said second coupler valve open position.

18. The connector system of claim 17, wherein:
said first coupler second lock assembly comprises a rotatable first coupler second locking ring configured to lock upon rotation in a first direction and unlock upon rotation in a second direction; and
said second coupler second lock assembly comprises a rotatable second coupler second locking ring configured to lock upon said rotation in said first direction and unlock upon said rotation in said second direction.

19. The connector system of claim 15, further comprising:
a first coupler first driver operable to forcibly urge said first coupler valve toward a first coupler valve open position which provides a first coupler passageway open condition that permits said flow of said fluid through said first coupler passageway; and
a second coupler first driver operable to forcibly urge said second coupler valve toward a second coupler valve open position which provides a second coupler passageway open condition that permits said flow of said fluid through said second coupler passageway;
wherein said first coupler passageway open condition and said second coupler passageway open condition provide an open fluid flow path condition which permits said fluid to flow through said connector system.

20. The connector system of claim 19, wherein:
said first coupler first driver is a component of said first coupler; and
said second coupler first driver is a component of said second coupler;
wherein said first coupler first driver is configured to be actuated by a second coupler second driver which is a component of said second coupler; and
wherein said second coupler first driver is configured to be actuated by a first coupler second driver which is a component of said first coupler.

* * * * *